Figure 1:
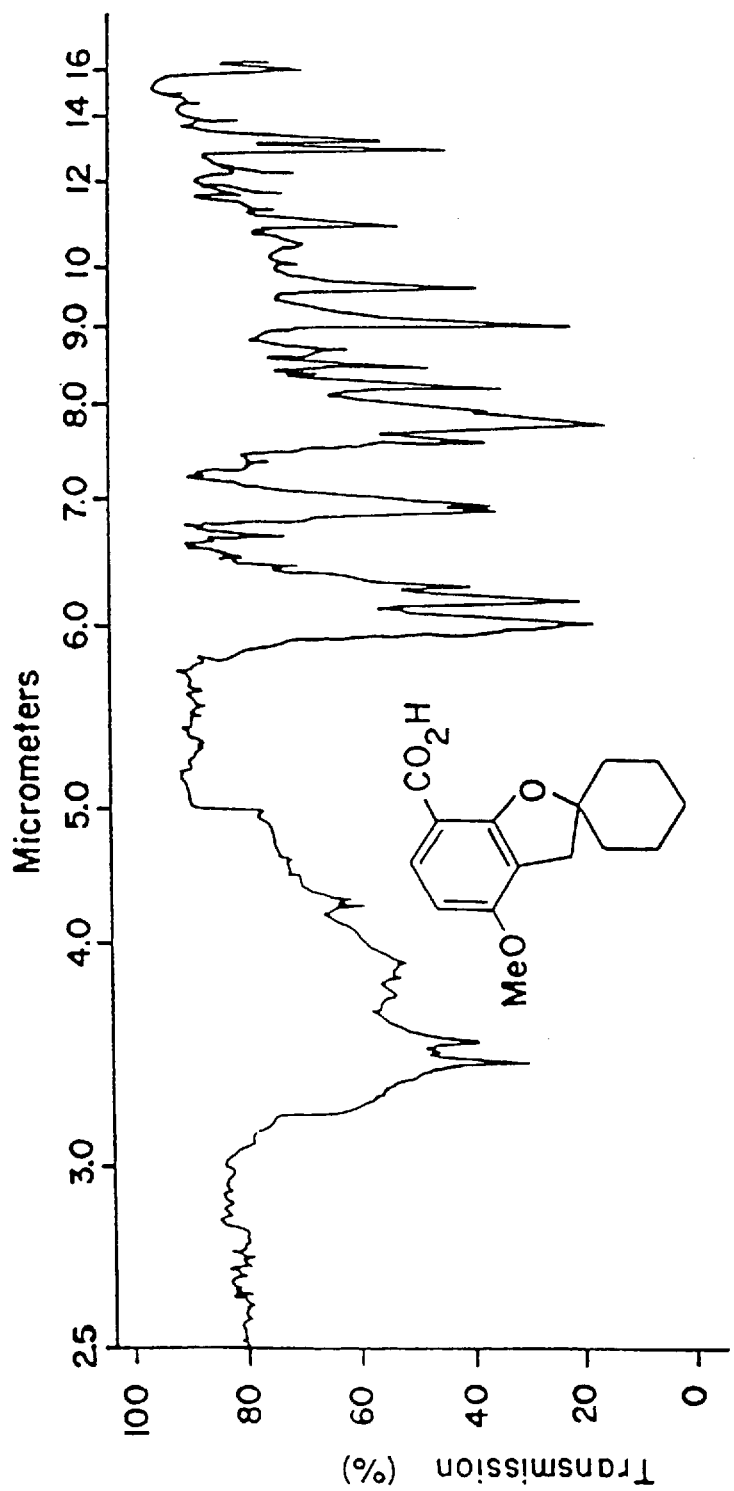

United States Patent [19]
Sindelar et al.

[11] Patent Number: 5,808,109
[45] Date of Patent: Sep. 15, 1998

[54] COMPOUNDS THAT INHIBIT COMPLEMENT AND/OR SUPPRESS IMMUNE ACTIVITY

[75] Inventors: Robert D. Sindelar, Oxford, Miss.; Barton J. Bradbury, West Chester, Ohio; Teodoro S. Kaufman, Rosario, Argentina; Stephen H. Ip, Framingham; Henry C. Marsh, Jr., Watertown, both of Mass.; Chew Lee, Kluang, Malaysia

[73] Assignees: T Cell Sciences, Inc., Needham, Mass.; The University of Mississippi, University, Miss.

[*] Notice: The term of this patent shall not extend beyond the expiration date of Pat. No. 5,366,986.

[21] Appl. No.: 484,094

[22] Filed: Jun. 7, 1995

Related U.S. Application Data

[63] Continuation of Ser. No. 87,676, Jan. 21, 1994, Pat. No. 5,506,247, which is a continuation-in-part of Ser. No. 623,849, Dec. 6, 1990, Pat. No. 5,366,986, which is a continuation-in-part of Ser. No. 182,275, Apr. 15, 1988, Pat. No. 5,173,499.

[51] Int. Cl.$^6$ .................................................. C07D 307/94
[52] U.S. Cl. ............................................................ 549/345
[58] Field of Search ............................................ 549/345

[56] References Cited

U.S. PATENT DOCUMENTS

| | | | |
|---|---|---|---|
| 3,128,286 | 4/1964 | Walker et al. | 260/346.2 |
| 3,518,283 | 6/1970 | Brossi et al. | 260/346.2 |
| 4,035,509 | 7/1977 | Nelson et al. | 424/317 |
| 4,229,466 | 10/1980 | Miyazaki et al. | 424/279 |
| 4,263,317 | 4/1981 | Martin et al. | 424/278 |
| 4,268,516 | 5/1981 | Lombardino et al. | 424/273 P |
| 4,301,292 | 11/1981 | Martin et al. | 548/239 |
| 4,404,221 | 9/1983 | Giamkowski et al. | 424/285 |
| 4,426,380 | 1/1984 | Wenk et al. | 424/244 |
| 4,451,461 | 5/1984 | Wenk et al. | 424/248.55 |
| 4,517,311 | 5/1985 | Giamkowski et al. | 549/345 |
| 4,558,043 | 12/1985 | Wenk et al. | 514/210 |
| 4,647,677 | 3/1987 | Tamura et al. | 549/462 |
| 4,740,519 | 4/1988 | Shroot et al. | 514/443 |
| 4,857,516 | 8/1989 | Terao et al. | 514/100 |
| 4,863,958 | 9/1989 | Belanger et al. | 514/469 |
| 5,173,499 | 12/1992 | Sindelar et al. | 514/462 |
| 5,366,986 | 11/1994 | Sindelar et al. | 514/374 |
| 5,401,767 | 3/1995 | Sindelar et al. | 514/462 |

FOREIGN PATENT DOCUMENTS

| | | |
|---|---|---|
| 28 21403 | 1/1979 | Germany . |
| 3031788 | 3/1981 | Germany . |

OTHER PUBLICATIONS

Bradbury and Sindelar, 1986, "Regioselective metalation in the synthesis of partial derivatives of the complement inhibitor K–76," Abstract No. 14, p. 24, 13th Annual MALTO Medicinal Chemistry/Pharmacognosy Meeting–In–Miniature, May 21–23, New Orleans, Louisiana.

Hong et al., 1979, "An anti–complementary agent, K–76 monocarboxylic acid: Its site and mechanism of inhibition of the complement activatoin cascade," J. Immunol., 122:2418.

Hong et al., 1981, "Inhibitory effect of K–76 monocarboxylic acid, an anticomplementary agent, on the C3b inactivator system," J. Immunol., 127:104.

Hong et al., 1981, "Simple methods for preparing EAC1, 4b, 2a, 3b, and EAC4b, 3b with human or guinea pig complement components using an anticomplementary agent, K–76 monocarboxylic acid," J. Immunol., 127:109.

Bumpers and Baum, 1983, "The effect of a novel C5 inhibitor (K–76 CONNa) on tumor cell chemotaxis," J. Lab. Clin. Med., 102:421.

Konno and Tsunifugi, 1983, "Induction of zymosan air pouch inflammation in rats and its characterization with reference to the effects of anticomplementary and anti–inflammatory agents," Dr. J. Pharmacol., 80:269.

Miyazaki et al., 1983, "Complement inhibitor, K–76 COOH," Farumashia (Japan) 19:912.

Ramm et al., 1983, "Size distribution and stablity of the trans–membrane channels formed by complement complex C5b–9," Mol. Immunol., 20:155.

Hudig et al., 1984, "Inhibition of human lymphocyte natural cytotoxicity and antibody–dependent cell–mediated cytotoxicity by K–76 COONa, a reagent that blocks complement activity," J. Immunol., 133:408.

Miyazaki et al., 1984, "Effects of K–76 monocarboxylic acid, an anticomplementary agent, in various in vivo immunological reactions and on experimental glomerulonaphritis," Complement 1:134.

Rudelman et al., 1984, "The mechanism of cell–mediated cytotoxicity, II. K–76 COONa, which inhibits the activity of Factor I and CS, inhibits early events in cytotoxic T–lymphocyte–mediated cytolysis and in T–lymphocyte activation," Cell Immunol., 88:16.

Kanno and Tsurufugi, 1985, "Inhibitory effect of a novel anti–complementary agent, K–76 COONa, on the release of histamine induced by zymosan and compound 48/80," Jpn. J. Pharmacol., 38:116.

Redelman et al., 1986, "The induction of human T–cell growth factor receptor precedes the reduction of RNA and occurs in the presence of inhibitors of RNA synthesis," Cytometry 7:453.

(List continued on next page.)

*Primary Examiner*—Amelia Owens
*Attorney, Agent, or Firm*—Pennie & Edmonds LLP

[57] ABSTRACT

The present invention is directed to compounds which suppress immune responses and/or selectively inhibit complement. These compounds contain an aromatic ring and are substituted dihydrobenzofurans, spirobenzofuran-2(3H)-cycloalkanes, and their open chain intermediates. The compounds of the present invention, and the pharmaceutically acceptable salts thereof, interrupt the proteolytic processing of C5 to bioactive components, exhibit immunosuppressive activities, and have therapeutic utility in the amelioration of disease and disorders mediated by complement and/or immune activity.

3 Claims, 8 Drawing Sheets

OTHER PUBLICATIONS

Iida et al., 1987, "Effect of the anticomplementary agent, K–76 monocarboxylic acid on experimental immune complex glomerulonephritis in rats," Clin. Exp. Immunol., 67:130.

Miyazaki et al., 1980, "A complement inhibitor produced by *Stachybotrys complementi*, nov. sp. K–76, a new species of fungi imperfecti," Microbiol. Immunol., 24(11):1091.

Kaise et al., 1979, "Structure of K–76, a complement inhibitor produced by *Stachybotrys complementi* nov. sp. K–76," J. Chem. Soc. Chem. Commun., 726.

McMurry and Erion, 1985, "Stereoselective total synthesis of the complement inhibitor K–76," J. Am. Chem. Soc., 107:2712.

Corey and Das, 1982, "Total synthesis of the complement inhibitor K–76 in racemic form. Structural assignment to K–76 monocarboxylic acid," J. Am. Chem. Soc., 104:5551.

Spanevello et al., 1982, "Regioselective synthesis of the spiro–benzofuran unit, present in several natural products, by an intramolecular Michael cyclization," Syn. Commun. 16(7):749.

Sullivan et al., 1981, "Antimicrobial constituents of the sponge *Siphonodictyon coralliphagum*, " Tetrahedron 37:979.

Dave et al., 1984, "A piscicidal chromanol and a chromenol from the brown alga *Dictyopteris undulata*, " Heterocycles 22(10):2301.

Gerwick and Fenical, 1981, "Ichthyotoxic and cytotoxic metabolites of the tropical brown alga *Stypopodium zonale* (Lamouroux) papenfuss," J. Org. Chem., 46:22.

Brandt et al., 1972, "Structure and synthesis of crombenin, a natural spirocoumaranone," J. Chem. Soc. Chem. Commun., 392.

Antua et al., 1986, "Synthesis of Grisan," Tetrahedron 42(20):5637.

Kazlauskas et al., 1978, "New quinones from a dicytoceratid sponge," Aus. J. Chem., 31:2685.

Jackson and Short, 1937, "Anisoxide. Part I," J. Chem. Soc., 513.

Grove et al., 1952, "Griseofulvin. Part IV," J. Chem. Soc., 3977.

Oxford et al., 1935, "CXXXIX. Studies in the biochemistry of microorganisms. XLIV. Fulvic acid, a new crystalline yellow pigment, a metabolic product of *P. griseofulvum* dierckx, *P. Flexuosum* dale and *P. Brefeldianum* dodge," Biochem J., 29:1102.

Weinberg, 1981, "Principles of medicinal chemistry," 2d. Ed. Foye, W.O., ed., Lea and Febiger, Philadelphia, PA. p. 813.

Closse et al., 1981, "2,3–dihydrobenzofuran–2–one: A new class of highly potent antiinflammatory agents," J. Med. Chem., 24:1465.

Hammond et al., 1989, "2,3–dihydro–5–benzofuranols as antioxidant–based inhibitors of leukotriene biosynthesis," J. Med. Chem., 32:1006.

Kruse et al., 1981, "Synthesis of spiro[isobenzofuran–1(3H), 4'–piperidines] as potential central nervous system agents. 6. Synthesis, C–13 NMR, and biological evaluation of cis–and trans–4–amino–3'–arylspiro–[cyclohexane–1,1'(3'H)–isobenzofuran] derivatives," J. Med. Chem. 24:617.

Narasimhan and Mali, 1983, "Synthesis of heterocyclic compounds involving aromatic lithiation reactions in the key step," Synthesis, 957.

Townsend and Bloom, 1981, "Studies of methoxymethyl–directed metalation," Tet. Lett. 22:3923.

Ronald, 1975, "Methoxymethyl ethers, an activating group for rapid and regioselective metalation," Tet. Lett. 46:3973.

Lielbriedis and Gudriniece, 1968, "Diketone–based heterocyclic compounds," Latv. PSR Zinat. Akad. Vestis, Kim. Ser. 2:192.

Becker et al., 1983, "Chemotactic factors of inflammation," Trends Pharmacol. Sci., 4:223.

Becker, 1967, "The relationship of the structure of phosphonate esters to their ability to inhibit chymotrypsin, trypsin, acetlycholinesterase and C'ia," Biochim. Biophys. Acta., 147:289.

Bradbury and Sindelar, 1989, "Synthesis of 4,7–disubstituted spirobenzofuran–2(3H)–cyclohexanes," J. Heterocyclic Chem., 26:1827.

Bult and Herman, 1983, "Inflammatory mediators released by complement–derived peptides," Agents and Actions 13(5/6):405.

Burge et al., 1978, "Inhibition of the alternative pathway of complement by gold sodium thiomalate in vitro," J. Immunol., 120(5):1625.

Cavarocchi et al., 1986, "Oxygen free radical generation during cardiopulmonary bypass: correlation with complement activation," Circulation 74(suppl.III):130.

Crawford et al., 1972, "Metalation of limonene. A novel method for the synthesis of bisabolane sesquiterpenes," J. Am. Chem. Soc., 94:4298.

Djura and Sargent, 1983, "The structure of isopannarin," Aust. J. Chem., 36:1057.

Eisen, 1979, "Cell–mediated hypersensitivity and immunity," Immunology Ch. 20, Harper and Row, Hagerstown, MD, p. 558.

Eisen et al., 1974, "Complement," Immunology Ch. 18, Harper and Row, Publishers Inc., Hagerstown, MD, p. 512.

Fugi et al., 1979, "Hard acid and soft nucleophile system. New efficient method for removal of benzyl protecting group," J. Org. Chem., 44(10):1661.

Fujimoto et al., 1983, "Spontaneous release of the Leu–2 (T8) molecule from human T cells," J. Exp. Med., 159:752.

Fujita et al., 1976, "Biosynthesis of natural products. Part 1. Incorporation of ent–kaur–16–ene and ent–kaur–16–en–15–one into enmein and oridonin," J. Chem Soc., 23:2098.

Glovsky et al., 1969, "Role of fumaropimaric acid in guinea pig complement dependent and non–complement dependent biologic reactions," J. Immunol., 102(1):1.

Grieco et al., 1975, "Model studies directed toward the total synthesis of vernolepin. III. Synthesis of the α–methyhlene–δ–valerolactone AB ring model," J. Org. Chem., 40(10):1450.

Gschwend and Rodriguez, 1979, "Heteroatom–facilitated llithiations," Org. React., 26;1.

Hansch and Yoshimoto, 1974, "Structure–activity relationships in immunochemistry. 2. Inhibition of complement by benzamidines," J. Med. Chem., 17(11):1160.

Hood et al., 1984, "Antigen–bound IgM and IgG antibodies initiate complement fixation," Immunology, 2d ed.. The Benjamin/Cummings Publishing Co., Menlo Park, CA, p. 339.

Hugli, 1981, "The structural basis for anaphylatoxin and chemotactic functions of C3a, C4a, and C5a," CRC Crit. Rev. Immunol., 1:321.

Johnson et al., 1975, "Release of histamine from rat mast cells by the complement peptides C3a and C5a," Immunology 28:1067.

Jolly et al., 1986, "Reduction of myocardial infarct size by neutrophil depletion: Effect of duration of occlusion," Am. Heart J., 112(4):682.

Kaufman and Sindelar, 1989, "A short and efficient synthesis of grisan," J. Heterocyclic Chem., 26:879.

Kaufman et al., 1989, "$^{13}$C NMR chemical shifts of the carbon atoms of the methoxymethyl group of di–ortho–substituted aromatic methoxymethyl ethers," J. Heterocyclic Chem. 27:1178.

Kirklin et al., 1983, "Complement and the damaging effects of cardiopulmonary bypass," J. Thorac. Cardiovasc. Surg., 86:845.

Lythgoe et al., 1956, "Calciferol and its relatives. Part II. An alternative synthesis of trans–1, 2'–cyclohexylidene–ethylidene–2–methylenecyclohexane," J. Chem. Soc., Part IV:4060–4065.

Meuer et al., 1984, "Triggering of the T3–Ti antigen–receptor complex results in clonal T–cell proliferation through an interleukin 2–depedent autocrine pathway," Proc. Natl. Acad. Sci. USA 81:1509.

Miescher and Muller–Eberhard, 1976, Text Book of Immunopathology, 2d ed., vols. I and II, Grune and Stratton, New York.

Miller et al., 1980, "Synthesis and enzymatic and inotropic activity of some new 8–substituted and 6,8–disubstituted derivatives of adenosine cyclic 3',5'–monophosphate," J. Med. Chem., 23:242.

Mori and Komatsu, 1988, "Synthesis of the complement inhibitor (–)–K–76 and of related compounds," Liebigs Ann. Chem., pp. 107–119.

Muller–Eberhard, 1978, "Complement: Molecular mechanisms, regulation and biologic function," Molecular Basis of Biological Degradative Processes, Berlin, R.D. et al., eds. Academic Press, NY, p. 65.

Narasimhan et al., 1979, "Synthetic application of lithiation reactions; Part XIII. Synthesis of 3–phenylcoumarins and their benzo derivatives," Synthesis, p. 906.

Rall et al., 1976, "Crown ethers. Application in the synthesis of chalcones," Tetrahedron Letters No. 13, p. 1033.

Regal and Pickering, 1983, "C5a and antigen–induced tracheal contraction: Effect of a combination of an antihistamine and cyclo–oxygenase inhibitors," Int. J. Immunopharmac., 5(1):71.

Rossen et al., 1985, "Selective accumulation of the first component of complement and leukocytes in ischemic canine heart muscle," Circulation Research 57(1):119.

Rubin et al., 1985, "Soluble interleukin–2 receptors are shed by activated human lymphocytes in vitro," Feb. Proc., 44:946 (Abstract No. 3131).

Rubin et al., 1985, "Soluble interleukin 2 receptors are released from activated human lymphoid cells in vitro," J. Immunol., 135(5):3172.

Sandberg, 1981, "Complement," in Cellular Functions in Immunity and Inflammation, Oppenheim, J.J. et al., eds., Elsevier/North Holland, New York, p. 373.

Schafer et al., 1986, "Deposition of the terminal C5b–9 complement complex in infarcted areas of human myocardium," J. Immunol., 137(6):1945.

Simpson and Lucchesi, 1987, "Free radicals and myocardial ischemia and reperfusion injury," J. Lab. Clin. Med., 110(1):13.

Tack et al., 1979, "Fifth component of human complement: Purification from plasma and polypeptide chain structure," Biochemistry 18(8):1490.

Takada et al., 1978, "Inhibition of the classical and alternative pathways by amino acids and their derivatives," Immunology 34:509.

Tsudo et al.,1984, "Expression of tac antigen on activated normal human B cells," J. Exp. Med., 160:612.

Vogt et al., 1979, "Interference of propamidine with binding of the fifth component of complement to surface–fixed C3b, and with C5 activation," Immunology 36:139.

Waldmann et al., 1984, "Expression of interleukin 2 receptors on activated human B cells," J. Exp. Med., 160:1450.

Webster et al., 1980, "Biological effects of the human complement fragments C5a and C5a (desarg) on neutrophil function," Immunopharmacol., 2:201.

Wheeler and Lerner, 1956, "Structure and Properties of cyclic compounds. III. Dissociation constants of simple $\alpha,\beta$–unsaturated cyclic acids," J. Am. Chem. Soc., 78:63.

WHO Scientific Group, 1977, "Chemotherapy of solid tumours," WHO Tech. Rep. Ser., 606:3.

Wissler, 1972, "Chemistry and Biology of the anaphylatoxin related serum peptide system," Eur. J. Immunol., 2:73.

Bradbury and Sindelar, 1987, "Synthesis and evaluation of partial derivatives of the complement inhibitor K–76," 14th Annual Malto Medicinal Chemistry–Pharmacognosy Meeting, May 17–19, Abstract Only.

Bradbury and Sindelar, 1987, "Synthesis of 4,7–disubstituted spirobenzofuran–2–(3H)–cyclohexanes," National American Chemical Society 194th Meeting, Sep. 4, New Orleans, Louisianna, Abstract Only.

Sindelar et al., 1990, "Potential complement inhibitors blocking release of C5a based on a natural product model," American Chemical Society Division of Medicinal Chemistry, 200th ACS National Meeting, Aug. 26–31, Washington, D.C, Abstract No. 178.

Sindelar et al., 1989, "Synthesis and evaluation of B/C/D–ring analogues of the anti–complement natural product K–76," American Chemical Society National 198th Meeting Sep. 10, Miami, Florida, Abstract No. 35.

Sindelar et al., 1988, "Synthesis of A/C/D–ring analogues of the anticomplement natural product K–76," American Chemical Society 196th National Meeting, Sep. 29, Los Angeles, Calfornia, Abstract Only.

Sindelar et al., 1988, "Synthesis and evaluation of B/C/D–ring analogues of the natural product complement inhibitor K–76," American Association of Pharmaceutical Scientists, AAPS Meeting Nov. 2, Orlando, Florida, Abstract Only.

Morrison et al., 1990, "Formation of 2,2–Spiro–Substituted 2,3–dihydrobenzo furans" Chemical Abstracts, vol. 112, No. 5, Abstract No. 35591b.

Bradbury et al., 1989, Synthesis of 4,7–Disubstituted Spiro benzo furan–2(H)–Cyclohexanes, Journal of Heterocyclic Chemistry, vol. 26, No. 6, p. 1827.

Teodoro S. Kaufman, Ranjan P. Srivastava, Robert D. Sindelar, Susanne M. Scesney and Henry C. Marsh, Jr., "Design, Synthesis and Evaluation of A/C/D–Ring Analogs of the Fungal Metabolite K–76 as Potential Complement Inhibitors", Journal of Medicinal Chemistry, vol. 38:9 pp. 1437–1445 (1995).

Teodoro S. Kaufman, Ranjan P. Srivastava, Robert D. Sindelar, Susanne M. Scesney and Henry C. Marsh, Jr., "The Design, Synthesis and Evaluation of A,C,D–Ring Analogs of the Fungal Metabolite K–76 as Complement Inhibitors: A Potential Probe for the Absolute Stereochemistry at Position 2", Bioorganic & Medicinal Chemistry Letters, vol. 5:5 pp. 501–506 (1995).

Ranjan P. Srivastava, Xiaoyan Zhu, Larry A. Walker and Robert D. Sindelar, "Further Structure–Activity–Relationship Studies on A/C/D–Ring Analogs of Complement Inhibitor K–76", Bioorganic & Medicinal Chemistry Letters, vol. 5:20 pp. 2429–2434 (1995).

Ranjan P. Srivastava, Xiaoyan Zhu, Larry A. Walker and Robert D. Sindelar, "Design, Synthesis and Evaluation of C/D–Ring Analogs of the Fungal Metabolite K–76 as Potential Complement Inhibitors", Bioorganic & Medicinal Chemistry Letters, vol. 5:15 pp. 1751–1755 (1995).

Thymidine Uptake of PHA Stimulated PBL

Thymidine Uptake of Anti-CD3 Stimulated PBL

Levels of IL-2R Released From Anti-CD3 Stimulated PBL

COMPOUNDS THAT INHIBIT COMPLEMENT AND/OR SUPPRESS IMMUNE ACTIVITY

This is a continuation of application Ser. No. 08/087,676, filed Jan. 21, 1994, now U.S. Pat. No. 5,506,247, which is a continuation-in-part of application Ser. No. 07/623,849, filed Dec. 6, 1990, now U.S. Pat. No. 5,366,986, which is a continuation-in-part of application Ser. No. 07/182,275 filed Apr. 15, 1988, now U.S. Pat. No. 5,173,499.

1. FIELD OF THE INVENTION

The present invention relates to compounds which inhibit complement and/or possess immunosuppressive activity. In particular, the compounds of the present invention, and the pharmaceutically acceptable salts thereof, selectively inhibit complement at the C5 step of complement activation. The compounds of the invention are substituted dihydrobenzofurans, spirobenzofuran-2(3H)-cycloalkanes, and their open chain intermediates that exhibit such inhibitory activates. Compounds of the invention also include 6,7-disubstituted spirobenzofuran-2(3H)-cycloalkanes and 4-substituted spirobenzofuran-2(3H)-cycloalkanes. The invention relates to the use of these compounds for therapy of immune and/or inflammatory disorders.

2. BACKGROUND OF THE INVENTION

2.1. THE COMPLEMENT SYSTEM

The complement system is a group of proteins that constitutes about 10 percent of the globulins in the normal serum of humans (Hood, L. E. et al. 1984, Immunology, 2d Edition, The Benjamin/Cummings Publishing Co., Menlo Park, Calif., p. 339). Complement (C) plays an important role in the mediation of immune and allergic reactions (Rapp, H. J. and Borsos, T., 1970, Molecular Basis of Complement Action, Appleton-Century-Crofts (Meredith), N.Y.). The activation of C components leads to the generation of a group of factors, including chemotactic peptides that mediate the inflammation associated with complement-dependent diseases. The sequential activation of the complement cascade may occur via the classical pathway involving antigen-antibody complexes, or by an alternative pathway which involves the recognition of certain cell wall polysaccharides. The activities mediated by activated complement proteins include lysis of target cells, chemotaxis, opsonization, stimulation of vascular and other smooth muscle cells, degranulation of mast cells, increased permeability of small blood vessels, directed migration of leukocytes, and activation of B lymphocytes, macrophages and neutrophils (Eisen, H. N., 1974, Immunology, Harper & Row, Publishers, Inc., Hagerstown, Md., p. 512).

During proteolytic cascade steps, biologically active peptide fragments, the anaphylatoxins C3a, C4a, and C5a (See WHO Scientific Group, WHO Tech. Rep. Ser. 1977, 606, 5 and references cited therein), are released from the third (C3), fourth (C4), and fifth (C5) native complement components (Hugli, T. E. CRC Crit. Rev. Immunol. 1981, 1, 321; Bult, H. and Herman, A. G. Agents Actions 1983, 13, 405). The C5a fragment, a cationic peptide derived from the first 74 amino acids of the amino-terminus of the C5 alpha subunit (Tack, B. F. et al. Biochemistry 1979, 18, 1490), is of particular pathological relevance. Regulation of C5a activity is by the endogenous plasma enzyme carboxypeptidase N (E.C. 3.4.12.7), which rapidly removes the carboxy-terminal arginine from C5a, producing the less potent but still active C5a des Arg. Reported effects of C3a and C5a upon specific immune responses are listed in Table I.

TABLE I

EFFECTS OF COMPLEMENT COMPONENTS
C3a AND C5a ON SPECIFIC IMMUNE RESPONSES

| Immune Response | C3a | C5a/C5a des Arg |
| --- | --- | --- |
| Specific antibody production in response to sheep red blood cells | Suppression | Enhancement |
| Polyclonal antibody production in response to Fc antibody fragment | Suppression | Enhancement |
| T cell proliferation in response to tetanous toxoid | Suppression | Enhancement |
| T cell proliferation in mixed lymphocyte reaction | No effect | Enhancement |
| T cell-mediated cytotoxicity | Suppression | Enhancement |

Among the wide variety of biological activities exhibited by C5a are contraction of smooth muscle (Wissler, J. H. Eur. J. Immunol. 1972, 2, 73), degranulation of mast cells (Johnson, A. R. et al., Immunol. 1975, 28, 1067), secretion of azurophilic granular enzymes from polymorphonuclear neutrophils (PMN) (Webster, R. O. et al., Immunopharmacol. 1980, 2, 201), and the chemotaxis of PMN (Wissler, J. H. Eur. J. Immunol. 1972, 2, 73; Becker, E. L. Trends Pharmacol. Sci. 1983, 4, 223) (Table II).

TABLE II

BIOLOGICAL EFFECTS OF C5a

I. Stimulation of neutrophil functions involved in inflammation
   A. chemotaxis
   B. chemokinesis
   C. aggregation
   D. lysosomal enzyme release
   E. generation of toxic oxygen products
II. Smooth muscle effects
   A. stomach smooth muscle contraction
   B. vasodilation
II. Promotion of histamine release
   A. mast cells
   B. basophils
IV. Immunoregulatory effects The active chemotactic factor in vivo is considered to be C5a des Arg (Becker, E. L. Trends Pharmacol. Sci. 1983, 4, 223).

The C5a or C5a des Arg fragments have been implicated in the infiltration of PMN (the chemotactic effect) in rheumatoid arthritis, certain forms of glomerulonephritis, experimental vasculitides such as the Arthus reaction, the acute pneumonitis produced by the instillation of chemotactic factors into the lungs of experimental animals with resulting release of leukotrienes C-4 and D-4 ($LTC_4$ and $LTD_4$), etc. In addition, the interactions between C5a and neutrophils have been considered to underlie tissue damage in several clinical situations. For instance, there exists a growing body of evidence for the role of oxygen-derived free radicals in mediating myocardial tissue injury during myocardial ischemia and, in particular, during the phase of myocardial reoxygenation and reperfusion. Among a number of possible sources of these radicals, the polymorphonuclear neutrophil has been the focus of primary attention. Studies have documented that neutrophil depletion or suppression of neutrophil function results in a significant salvage of myocardial tissue that is subjected to a period of regional ischemia followed by reperfusion (Simpson, P. J. and Lucchesi, B. R. J. Lab. Clin. Med. 1987, 110(1), 13–30). Neutrophil depletion in dogs resulted in significantly smaller myocardial infarcts after 90 minute occlusion with 24 hour reperfusion (Jolly, S. R. et al. Am. Heart J. 1986, 112, 682–690).

One study documented the activation of complement and generation of oxygen-derived free radicals during cardiopulmonary bypass. The administration of protamine during cardiopulmonary bypass further activated complement (Cavarocchi, N. C. et al., Circulation 1986, 74, 130–133; Kirklen, J. K. et al. J. Thorac. Cardiovasc. Surg. 1983, 86, 845–857). Also, recombinant tissue plasminogen activator (r-TPA), which in recent clinical trials has been found to be an effective thrombolytic agent in patients with acute myocardial infarction, was shown to activate complement. A striking increase in the level of C4a, C3a, and C5a was found in patients receiving r-TPA as compared to the level of these complement peptides before administration of the drug (Bennett, W. R. et al. J. Am. Coll. Cardiol. 1987, 10(3), 627–632). Schafer and co-workers were able to positively identify the deposition of terminal C5b-9 complement complex in myocardial cells located within zones of infarction in human tissue (J. Immunol. 1986, 137(6), 1945–1949). Likewise, the selective accumulation of the first component of complement and leukocytes in ischemic canine heart muscle has been found (Rosen, R. D. et al. Circ. Research, 1985, 57, 119–230). In one study, the depletion of complement was found to increase the blood flow in ischemic canine myocardium. This increased blood flow was found, in turn, to increase the supply and utilization of oxygen in complement depleted animals versus control animals (Grover, G. J. and Weiss, H. R. Basic Res. Cardio. 1987, 82(1), 57–65). Complement activation is also believed to initiate adult respiratory distress syndrome (ARDS). This syndrome, also known as adult respiratory failure, shock lung, diffuse alveolar damage, or traumatic wet lungs, is characterized clinically by the rapid onset of severe life-threatening respiratory insufficiency that is refractory to oxygen therapy. (Miescher, P. A. and Muller-Eberhard, H. J., eds., 1976, Text Book of Immunopathology, 2d Ed., Vols. I and II, Grune and Stratton, New York; Sandberg, A. L., 1981, in *Cellular Functions in Immunity and Inflammation*, oppenheim, J. J. et al., eds. Elsevier/North Holland, New York, p. 373; Conrow, R. B. et al. *J. Med. Chem* 1980, 23, 242; Regal, J. F.; and Pickering, R. H. *Int. J. Immunopharmacol.* 1983, 104, 617). Some of the clinical implications of C5a release are listed in Table III.

TABLE III

CLINICAL IMPLICATIONS OF C5a RELEASE

Rheumatoid Arthritis

Acute Gouty Arthritis
Acute Immunological Arthritis
Pulmonary Disorders

Adult Respiratory Distress Syndrome
Pulmonary Dysfunction—Hemodialysis
Chronic Progressive Pulmonary Dis-Cystic Fibrosis
Byssinosis
Asbestos-Induced Inflammation
Inflammation of Systemic Lupus Erythematosus
Inflammation of Glomerulonephritis
Purtscher's Retinopathy
Hemorrhagic Pancreatitis
Renal Cortical Necrosis
Primary Biliary Cirrhosis Inflammation
Nephropathology TABLE III-continued CLINICAL IMPLICATIONS OF C5a RELEASE Cranial Nerve Damage in Meningitis
Tumor Cell Metastasis
Extended Tissue Destruction in Myocardial Infarction
Extended Tissue Destruction in Burns

2.2. CELL-MEDIATED IMMUNE RESPONSES

A variety of immune responses independent of the complement system are known to be mediated by specifically reactive lymphocytes. These responses may give rise to autoimmune diseases, hypersensitivity, or simply allergic reactions. Some examples of these responses include delayed-type hypersensitivity, allograft rejection, graft versus host disease, drug allergies, or resistance to infection. Autoimmune disorders may include atrophic gastrititis, thyroiditis, allergic encephalomyelitis, gastric mucosa, thyrotoxicosis, autoimmune hemolytic anemia, and sympathetic ophthalmia (Eisen, H. N., 1979, Immunology, Harper and Row, Hagerstown, Md., pp. 557–595).

2.3. ORGANIC COMPOUNDS WHICH INHIBIT COMPLEMENT, AMELIORATE INFLAMMATION, AND/OR POSSESS IMMUNOSUPPRESSIVE ACTIVITY

Many chemicals have been reported to diminish complement-mediated activity. Such compounds include: amino acids (Takada, Y. et al. Immunology 1978, 34, 509); phosphonate esters (Becker, L. Biochem. Biophy. Acta 1967, 147, 289); polyanionic substances (Conrow, R. B. et al. J. Med. Chem. 1980, 23, 242); sulfonyl fluorides (Hansch, C.; Yoshimoto, M. J. Med. Chem. 1974, 17, 1160, and references cited therein); polynucleotides (DeClercq, P. F. et al. Biochem. Biophys. Res. Commun. 1975, 67, 255); pimaric acids (Glovsky, M. M. et al. J. Immunol. 1969, 102, 1); porphines (Lapidus, M. and Tomasco, J. Immunopharmacol. 1981, 3, 137); several antiinflammatories (Burge, J. J. et al. J. Immunol. 1978, 120, 1625); phenols (Muller-Eberhard, H. J. 1978, in Molecular Basis of Biological Degradative Processes, Berlin, R. D. et al., eds. Academic Press, New York, p. 65); and benzamidines (Vogt, W. et al Immunology 1979, 36, 138). Some of these agents express their activity by general inhibition of proteases and esterases. Others are not specific to any particular intermediate step in the complement pathway, but, rather, inhibit more than one step of complement activation. Examples of the latter compounds include the benzamidines, which block C1, C4 and C5 utilization (Vogt, W. et al. Immunol. 1979, 36, 138).

2.4. SPIROBENZOFURAN-2(3H)-CYCLOALKANES AND K-76

K-76 is a fungal metabolite from *Stachybotrys complementi* nov. sp. K-76. Metabolite K-76 has a drimane skeleton combined with a benzene ring attached through a spirofuran, and has been determined as 6,7-diformyl-3',4', 4a',5',6',7',8', 8a'-octahydro-4,6',7'-trihydroxy-2',5',5',8a'-tetramethylspiro [1'(2'H)-naphthalene-2(3H)-benzofuran ] (Kaise, H. et al. J. Chem. Soc. Chem. Commun. 1979, 726). The monocarboxylic acid derivative, K-76 COOH, is obtained when K-76 is selectively oxidized by silver oxide. (Corey, E. J. and Das, J. J. Amer. Chem. Soc. 1982, 104, 5551).

Both K-76 and K-76 COOH have been shown to inhibit complement mainly at the C5 step (Hong, K. et al. J.

Immunol. 1979, 122, 2418; Miyazaki, W. et al. Microbiol. Immunol. 1980, 24, 1091). In a classical hemolytic reaction system, hemolysis of sensitized sheep erythrocytes by guinea pig serum was reduced 50% by K-76 at $7.45 \times 10^{-5}$M, or K-76 COONa at $3.41 \times 10^4$M (Hong, K. et al. J. Immunol. 1979, 122, 2418; Miyazaki, W. et al. Microbiol. Immunol. 1980, 24, 1091). Similar results were observed in a hemolytic reaction system via the alternative pathway of complement activation.

Both K-76 and K-76 COOH prevented the generation of a chemotactic factor from normal human complement (Bumpers, H. and Baum, J. J. Lab. Clinc. Med. 1983, 102, 421). K-76 has been shown to reduce the amount of protein excreted in urine of rats with nephrotoxic glomerulonephritis (Iida, H., et al., Clin. Exp. Immunol. 1987, 67, 130–134), and is reported to greatly increase the survival of mice with a spontaneous systemic lupus erythematosis-like disease and to suppress Forssman shock in guinea pigs and mice (Miyazaki, W. et al. Microbiol. Immunol. 1980, 24, 1091). At high concentrations of K-76 or K-76 COOH, some inhibition of the reactions of C2, C3, C6, C7, and C9 with their respective preceding intermediaries is exhibited. However, both compounds' inhibitory action is mainly the generation in vitro of EACI, 4b,2a,3b,5b (sensitized sheep erythrocytes carrying the indicated complement components) from C5 and EACl,4b,2a,3b; the acceleration of the decay of any EACl,4b,2a,3b,5b present; and blocking generation of the chemotactic peptides (Hong, K. et al. J. Immunol. 1981, 127, 109; Ramm, L. E., et al. Mol. Immunol. 1983, 20, 155).

K-76 COOH is also reported to be an anti-hepatitic agent (West German Patent Application, Publication No. 3,031, 788, published Mar. 12, 1981, by Shinohara, M. et al.), and possesses the ability to inhibit antibody-dependent cell-mediated cytotoxicity and natural killer lytic activity (Hudig, D. et al. J. Immunol. 1984, 133, 408–413). K-76 or K-76 COOH has also been reported to inhibit the C3b inactivator system of complement (Hong, K. et al. J. Immunol. 1981, 127, 104–108). Semi-synthetic derivatives of K-76 have been patented as anti-allergy, anti-tumor, and anti-nephritic agents (Belgium Patent No. 867,095, published November 16, 1978, by Shinohara, M. et al.). The isolation of K-76, its uses in the treatment of autoimmune diseases, and the preparation of its derivatives have been described in a number of patents (See Japanese Patent Applications (Kokai), Publication Nos. 54 092680 (published July 23, 1979), 54 106458 (published Aug. 21, 1979), 57 083281 (published May 25, 1982), by Shinohara, M. et al.; Japanese Patent (Kokoku) No. 85 030289 (published Mar. 20, 1979)).

A number of additional compounds which contain the substructure of a spirobenzofuran-2(3H)-cycloalkane are known. These compounds include griseofulvin (Weinberg, E. D., 1981, in Principles of Medicinal Chemistry, 2d Ed., Foye, W. O., ed., Lea & Febiger, Philadelphia, Pa., p. 813), isopannarin (Djura, P. and Sargent, M. V. Aust. J. Chem. 1983, 36, 1057), and metabolites of *Siphonodictyon coralliphagum* (Sullivan, B., et al. Tetrahedron 1981, 37, 979).

The general synthetic methodology utilized for the synthesis of the compounds of the present invention involves regioselective aromatic lithiation reactions. Numerous oxygen-containing heterocycles have been made using regioselective aromatic lithiation reactions, but few preparations of dihydrobenzo[b]furans have been described (Narasimhan, N. S. and Mali, R. S. Synthesis 1983, 957). Three reported syntheses of K-76 itself (Corey, E. J. and Das, J. J. J. Am. Chem. Soc. 1982, 104, 5551; McMurray, J. E. et al. Am. Chem. Soc. 1985, 107, 2712 Mori, K. et al. Ann. Chem. 1988, 107–119) utilize metalation techniques in the coupling of the terpenoid portion to the aromatic moiety, but neither provide sufficient flexibility to allow for analog preparations via subsequent elaboration of the aromatic ring.

3. SUMMARY OF THE INVENTION

The present invention is directed to compounds which suppress immune responses and/or selectively inhibit complement. In a specific embodiment, such compounds interrupt the proteolytic processing of C5 to bioactive components, blocking the release of C5a. The compounds of the present invention also exhibit immunosuppressive activities, such as for example, the ability to inhibit natural killer activity, lymphocyte proliferations, and T cell activation. The compounds of the present invention have therapeutic utility in the amelioration of disease and disorders mediated by complement and/or immune activity. In specific embodiments, they may be used for the treatment of autoimmune disease or the many diseases associated with the "inappropriate" activation of the complement system. In specific embodiments, a compound of the invention has greater activity than the natural product K76.

The invention further provides improved synthetic routes for the preparation of the compounds.

In one embodiment of the present invention, compounds are provided which have selectivity in inhibition of C5a release. In particular, such compounds can have utility in limiting the extent of trauma-induced tissue destruction, in the prevention and/or treatment of adult respiratory distress syndrome and damage induced by ischemic heart conditions.

In other specific embodiments, compounds of the invention which exhibit immunosuppressive activity can be used in the prevention and/or treatment of autoimmune disease or the rejection of transplanted organs and/or tissues.

A further embodiment of this invention includes the combined therapy that can be obtained by treating patients with disorders that are routinely treated with thrombolytic agents such as tissue plasminogen activator, streptokinase or urokinase (e.g. myocardial infarction patients) with a combination of the compounds of this invention and the routinely administered thrombolytic compounds.

The present invention is also directed to pharmaceutical compositions comprising such compounds or the salts thereof.

3.1 DEFINITIONS

As used herein, the following abbreviations and terms shall have the meanings indicated:

n-BuLi=n-butyllithium
t-BuLi=tert-butyllithium
t-BuSLi=lithium tert-butylthiolate
C=complement
CHO=Chinese hamster ovary
CPM=counts per minute
$Et_2O$=diethyl ether
HMPA=hexamethylphosphoric triamide
IgG=immunoglobulin G
$^i$PrOH=isopropanol
IR=infrared
K-76 COOH=the monocarboxylic acid derivative of K-76
K-76 COONa=the sodium salt of the monocarboxylic acid derivative of K-76

LAH=lithium aluminum hydride
MOM=methoxymethyl group
NK=natural killer
NMR=nuclear magnetic resonance
PBL=peripheral blood lymphocyte(s)
PCC=pyridinium chlorochromate
PHA=phytohemagglutinin
PMN=polymorphonuclear cells
RLi=alkyllithium
THF=tetrahydrofuran
TLC=thin layer chromatography
TMEDA=N,N,N',N'-tetramethylethylenediamine
TMS=tetramethylsilane
TriMEDA=N,N,N'trimethylethylenediamine The term "bioisosteric" group, as used in the present invention, describes an alternative chemical group whose electronic configuration is substantially analogous with the group to be replaced such that the polarity and charge of the whole molecule do not change. However, variations in the size, number of atoms or electron structure of the bioisosteric group (or "bioisostere") are permitted which variations may affect its function. Bioisosteres may be acidic (e.g., capable of releasing a proton and, subsequently, bearing a negative charge), basic (e.g., capable of being protonated and, subsequently, bearing a positive charge) or neutral (e.g., not normally capable of functioning as an acidic or basic group).

Unless otherwise stated or indicated, the term "alkyl" as used herein refers to methyl, ethyl, and n-propyl, isopropyl, n-butyl, isobutyl, sec-butyl, or tert-butyl groups. The term "alkanol" denotes a compound derived from coupling an alkyl group and hydroxyl radical. Similarly, the term "alkoxy" refers to methoxy, ethoxy, n-propyloxy, isopropyloxy, n-, iso-, sec, and tert-butoxy, phenoxy, benzyloxy groups and substituted derivatives thereof. The term "lower" refers to the numerical range of 1 to 4 carbon atoms and includes linear or branched skeletons.

Unless otherwise stated or indicated, the term "halogen" as used herein includes fluorine, chlorine, bromine, and iodine.

Unless otherwise stated or indicated, a given structure, formula, or nomenclature for the substituted dihydrobenzofuran analogs of this invention shall subsume all stereoisomers thereof.

Unless otherwise stated or indicated, a reference made to a final compound of the invention which is a carboxylic acid, is also meant to include the salt form of such carboxylic acid such as alkali and alkaline-earth metal salts obtained therefrom.

4. BRIEF DESCRIPTION OF THE FIGURES

FIG. 1 illustrates the infrared spectrum of compound 11a. The spectrum is presented for the compound pelletized in potassium bromide.

Figure 2:
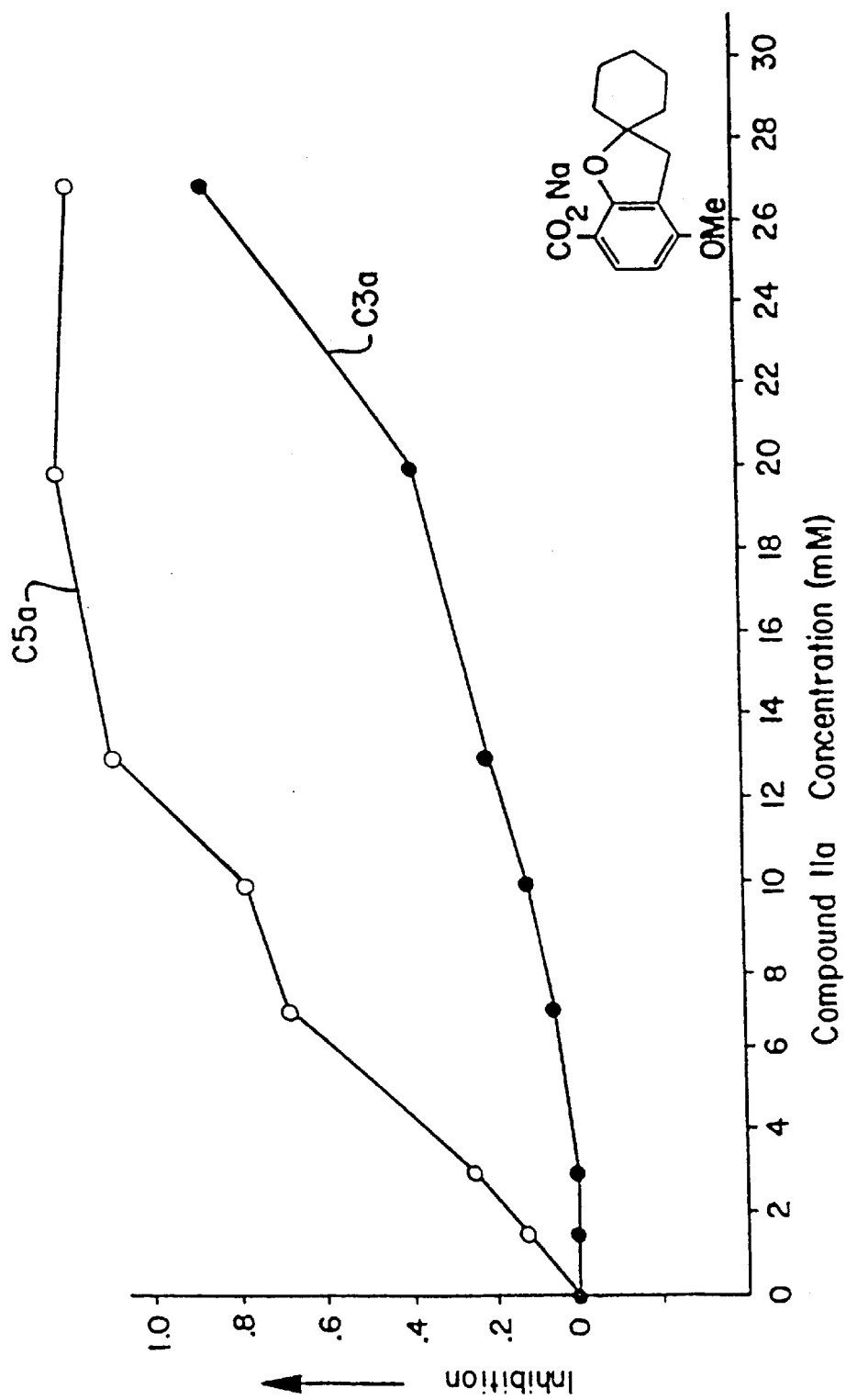

FIG. 2 demonstrates the inhibition of complement peptide C5a or C3a production by compound 11a. The inhibition (as described in Section 6.6, infra) of C5a and C3a production is shown as a function of compound 11a concentration.

Figure 3:
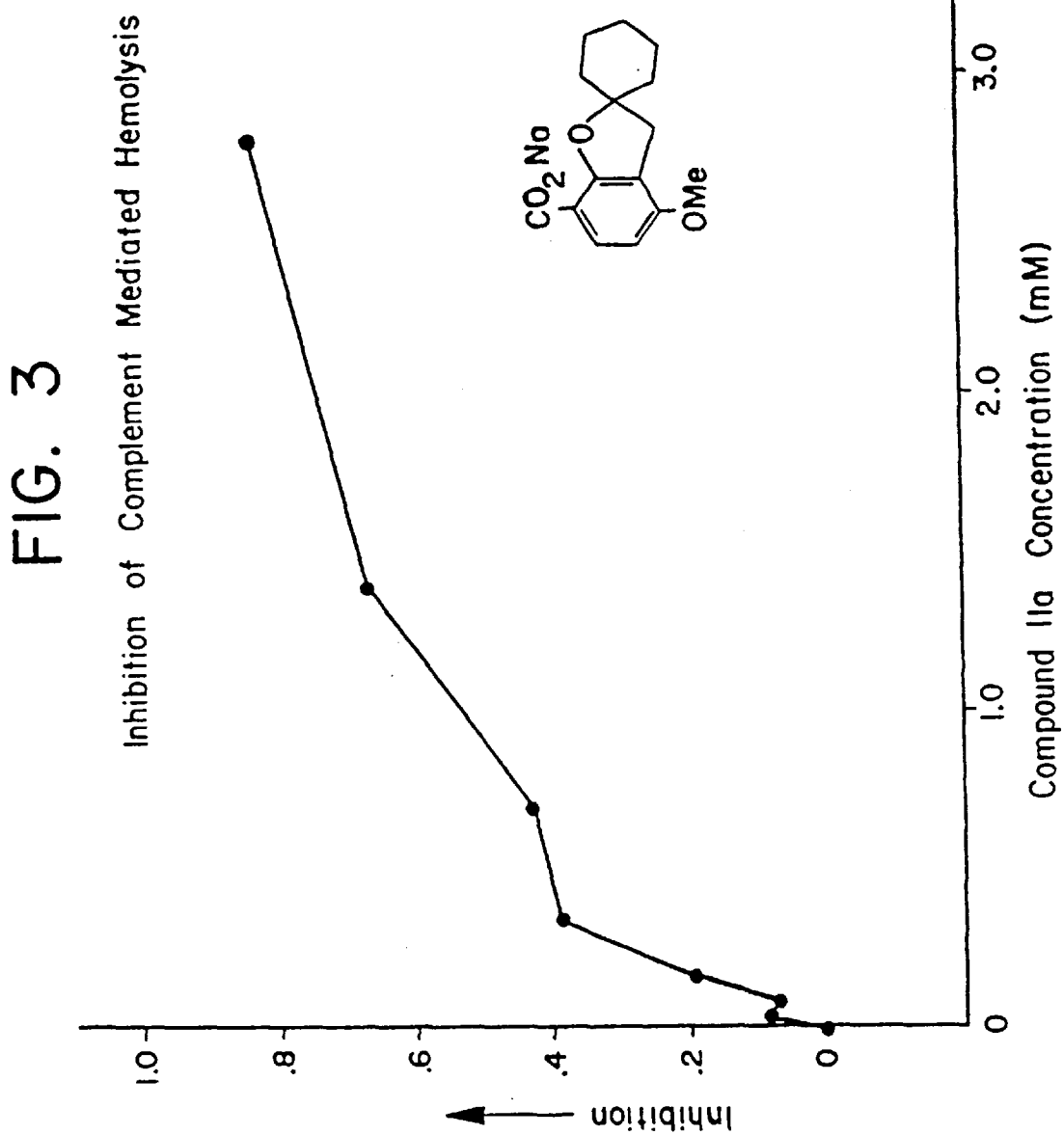

FIG. 3 demonstrates the inhibition of complement-mediated hemolysis by compound 11a. Inhibition of complement-mediated hemolysis, assayed as described in Section 6.6.2 infra, is shown as a function of compound 11a concentration.

Figure 4:
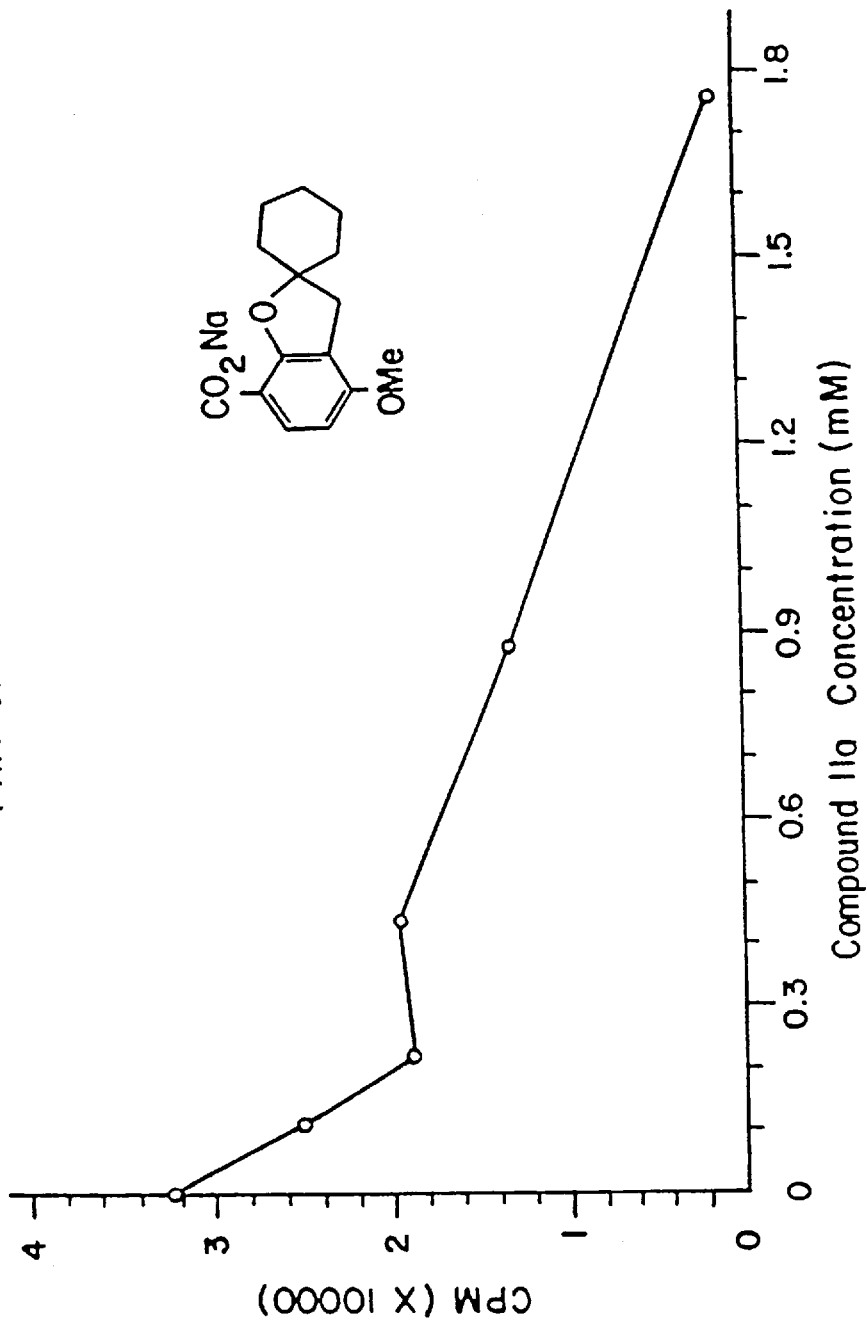

FIG. 4 demonstrates the inhibition of proliferation of peripheral blood lymphocytes (PBL) by compound 11a. $^3$H-Thymidine incorporation by PHA-stimulated PBL is shown as a function of compound 11a concentration.

Figure 5:
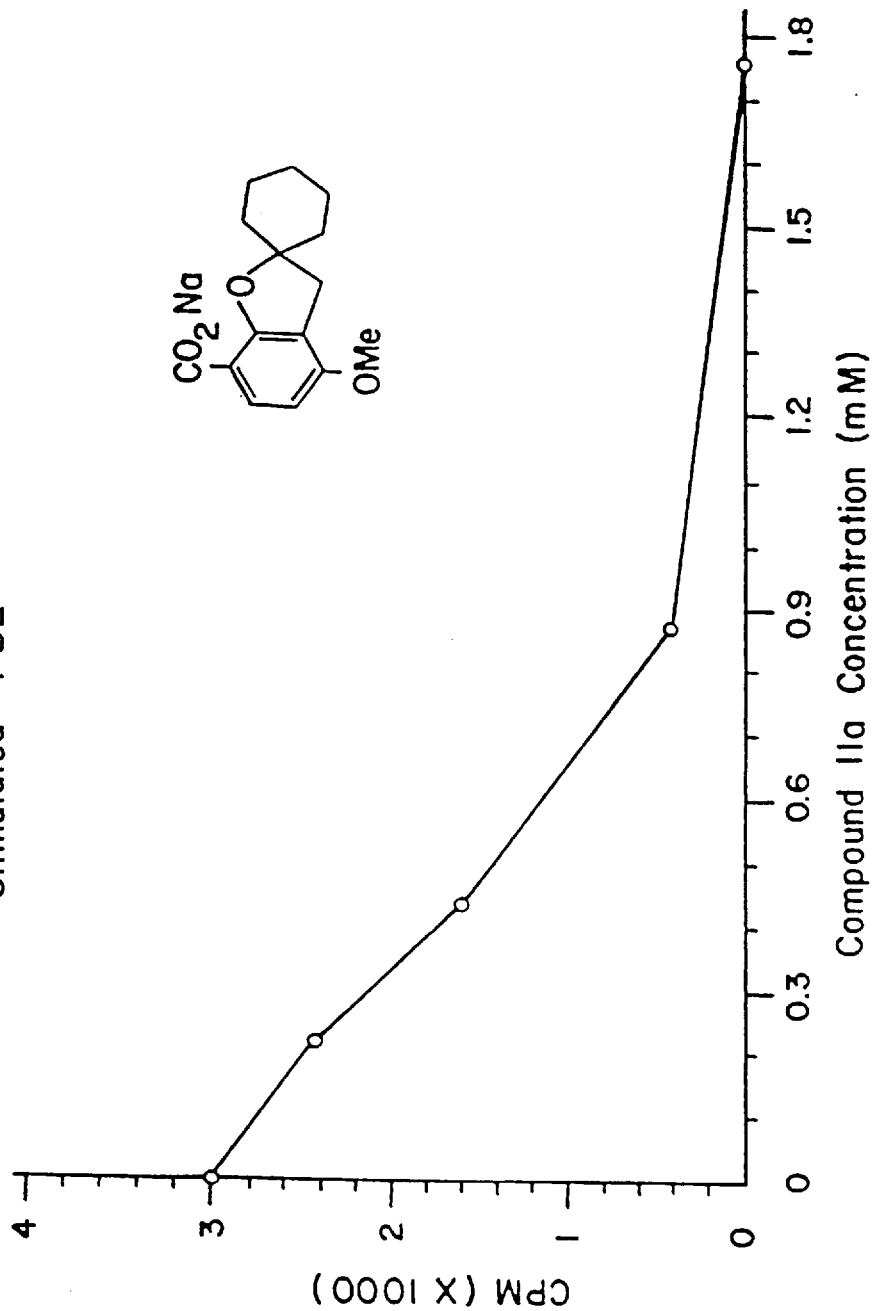

FIG. 5 demonstrates the inhibition of proliferation of PBL by compound 11a. $^3$H-Thymidine incorporation by antiCD3 antibody-stimulated PBL is shown as a function of compound 11a concentration.

Figure 6:
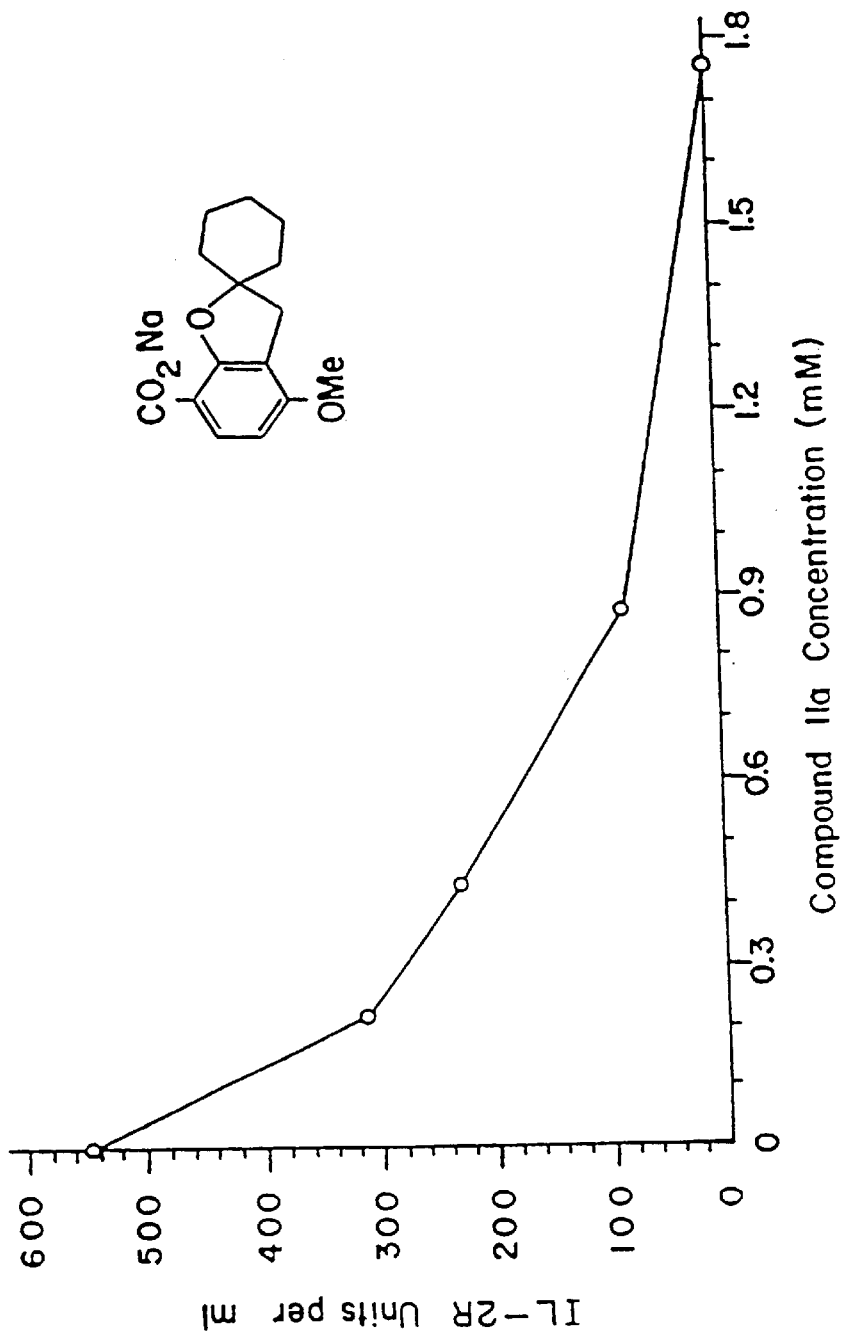

FIG. 6 demonstrates the inhibition of interleukin-2 receptor (IL-2R) release from PBL by compound 11a. The level of IL-2R in the supernatant of PBL cultures stimulated with anti-CD3 antibody, in the presence of compound 11a, was measured by use of an enzyme-linked immunosorbent assay, and is shown as a function of compound 11a concentration.

Figure 7:
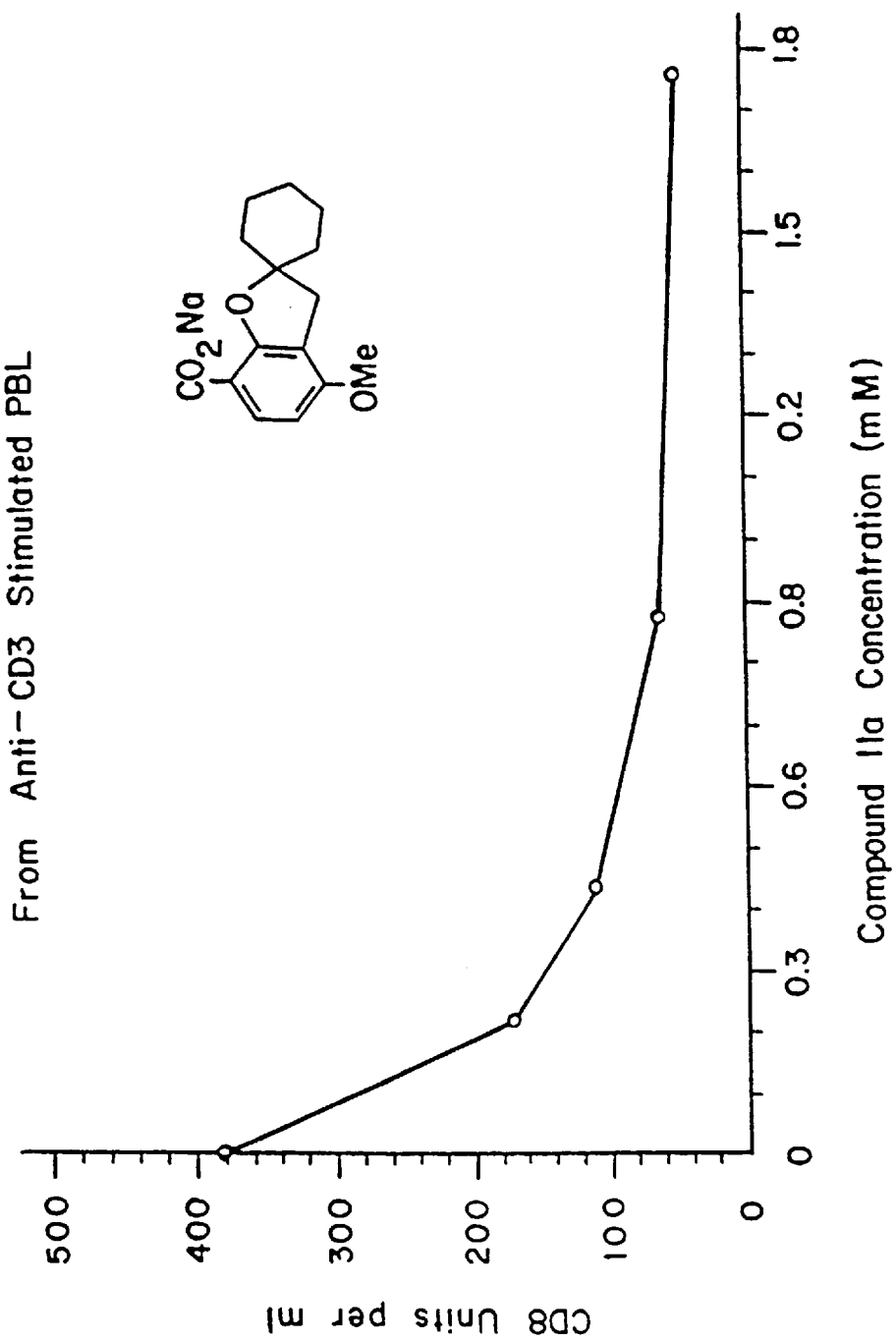

FIG. 7 shows the inhibition of CD8 protein release from PBL by compound 11a. The level of CD8 in the supernatant of PBL cultures stimulated with anti-CD8 antibody, in the presence of compound 11a, was measured by use of an enzyme-linked immunosorbent assay, and is shown as a function of compound 11a concentration.

Figure 8:
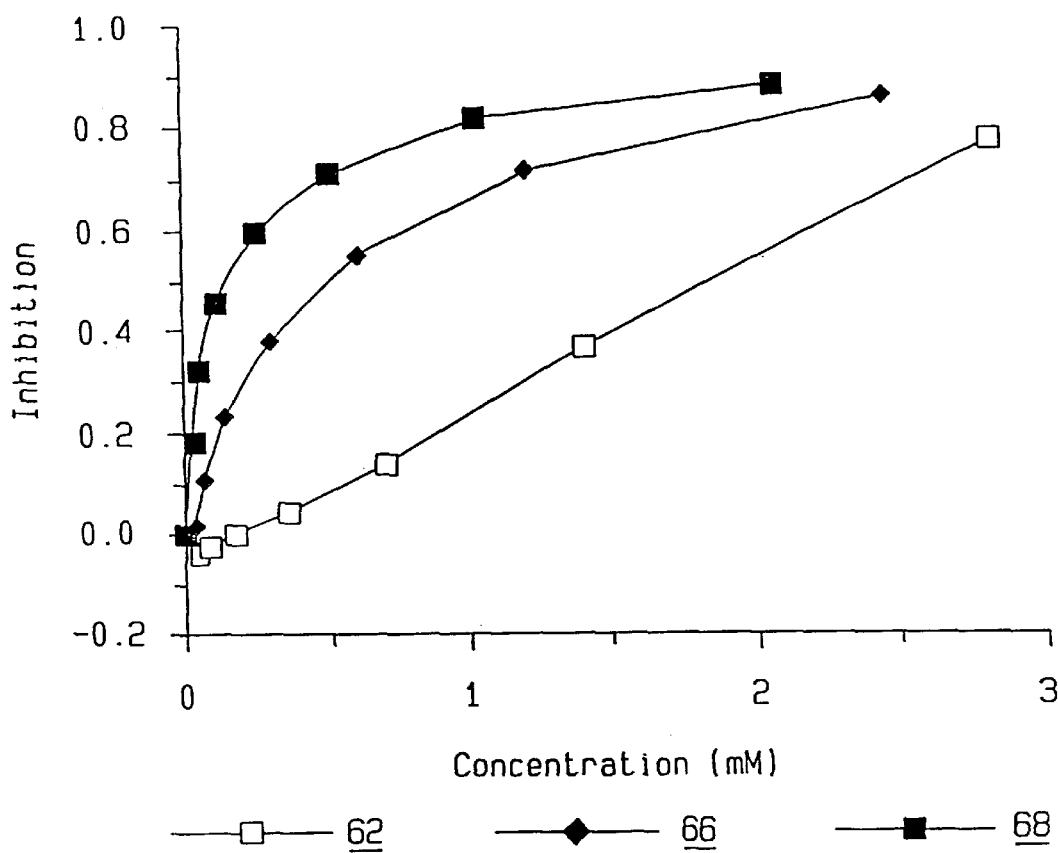

FIG. 8 demonstrates the inhibition of complement-mediated hemolysis by the disubstituted spirobenzofuran compounds 62, 66, and 68. Inhibition is shown as a function of compound concentration.

5. DETAILED DESCRIPTION OF THE INVENTION

The present invention relates to compounds which inhibit complement and/or possess immunosuppressive activity. The compounds of the invention contain an aromatic ring and are substituted dihydrobenzofurans, spirobenzonfuran-2(3H)-cycolakanes, and their open chain intermediates. In particular, such compounds can be partial analogs of the fungal metabolite K-76.

The complement inhibitors of the invention inhibit C5 activation, that is, the proteolytic generation of bioactive complement fragments C5a and C5b from C5. Such compounds have value in the treatment or prevention of diseases or disorders associated with undesirable or inappropriate activation of the complement system. In specific embodiments, the compounds of the invention can be used in the treatment of inflammatory disorders. They may also be used for the treatment of cardiovascular disease.

The present invention also relates to compounds which possess immunosuppressive activity. In particular, such compounds inhibit immune responses. In specific embodiments, the compounds of the invention can inhibit the killing activity of mononuclear cells, lymphocyte proliferation and/or activation. The immunosuppressive compounds of the invention can be valuable in the treatment of various immune disorders.

Furthermore, the compounds of the invention may possess one or more of the K-76-like activities described supra in Section 2.4 and in the references cited therein.

The compounds of the present invention, and the intermediates and methods used in their preparation, are described in detail below.

5.1. COMPOUNDS WHICH INHIBIT COMPLEMENT AND/OR SUPPRESS IMMUNE ACTIVITY

The present invention relates to organic compounds which inhibit complement and/or suppress immune activity. The organic compounds of the invention comprise substituted dihydrobenzofurans of the general formula 3 and substituted spirobenzofuran-2(3H)-cycloalkanes of the general formula 4. The groups represented by R and $R_1$–$R_4$ include, among others, hydrogen and linear or branched lower alkyl groups having 1 to 4 carbon atoms as defined previously in Section 3.1, supra. In addition, $R_1$–$R_4$ may each

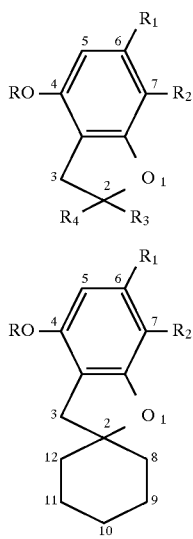

independently represent halogen, amino, amidic, hydroxyl, hydroxyalkyl, alkyloxy, nitro, formyl, acetal, carboxylic acid, trifluoroacetyl, N-substituted lower alkyl carbamoyl, substituted vinyl having up to 10 carbon atoms, an alkylidene group having up to 20 carbon atoms, an aliphatic acyl, a substituted aliphatic acyl, an aromatic acyl, a substituted aromatic acyl, a sulfamoyl, an aminomethyl, N-(lower alkyl) aminomethyl, a N,N-di(lower alkyl) aminomethyl, a heterocyclic ring bearing at least one heteroatom selected from nitrogen, oxygen or sulfur (e.g., a tetrazole or oxazoline group), an N-acylcarbamoyl, an amidino or a hydrazide. Moreover, $R_1$, $R_2$ and the carbon atoms to which they are attached may together form a five-or six-membered ring (e.g., a cyclic anhydride, such as a phthalic anhydride derivative; a lactone; or a hydroxy-substituted lactone).

Other groups which may be represented independently by $R_3$ and $R_4$ include hydrocarbons of 4 to 24 carbon atoms which may be of medium-length, long-chain, linear, branched, cyclic, saturated, unsaturated, unsubstituted, or heteroatom substituted. Moreover $R_3$, $R_4$, and the carbon atom to which they are attached may form a cyclic hydrocarbon group of 5–24 carbon atoms which may include a five-, six-, or seven-membered saturated or unsaturated ring comprised exclusively of carbon and hydrogen, or in combination with a heteroatom. The ring may be unsubstituted or may contain extra-cyclic heteroatom or hydrocarbon substituents.

This invention also relates to synthetic open chain intermediate compounds of the general formula 5 wherein R, $R_1$, and $R_2$ are defined as above for formulae 3 and 4. In addition, $R_5$ represents hydrogen, lower alkyl groups, or suitable hydroxyl protecting groups such as methoxymethyl, tetrahydropyranyl, 2-methoxypropyl, 2-methoxyethoxymethyl, triarylmethyl, benzyl, methylthiomethyl, or tert-butyl-dimethylsilyl group. The $R_6$ group encompasses chemical groups represented by $R_1$–$R_4$ as defined above for formulae 3 and 4 as well as substituent cyclohexenylmethyl (5a), limonenyl (5b), and carvone-derived diol acetonide (5c) groups. Other compounds may also be derived from

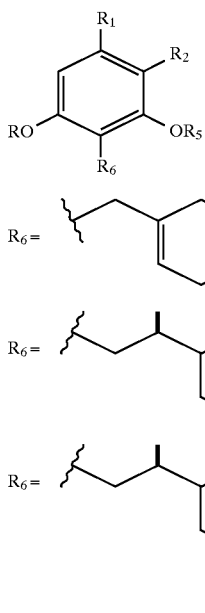
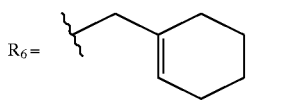
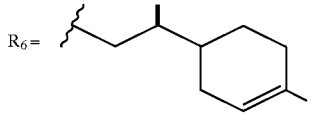
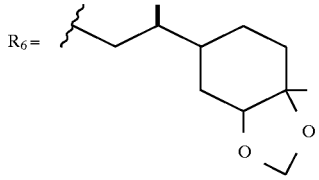

intermediates 5 and 5a–c, which are, in turn, converted to products of general formulae 3 or 4 as discussed in the following sections. Table V lists representative compounds which comprise the general formula 4 of the present invention; this list is not intended to be comprehensive.

TABLE V

COMPLEMENT INHIBITORS OF THE PRESENT INVENTION[a]

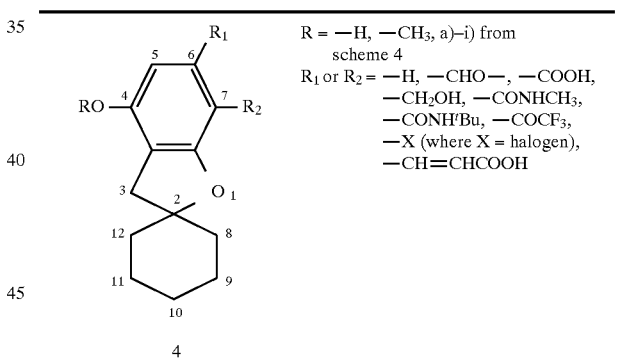

| | R = —H, —CH$_3$, a)–i) from scheme 4 |
|---|---|
| | $R_1$ or $R_2$ = —H, —CHO—, —COOH, —CH$_2$OH, —CONHCH$_3$, —CONH$^t$Bu, —COCF$_3$, —X (where X = halogen), —CH=CHCOOH |

4

[a]Substituents on the spirocyclohexane ring may also be present; e.g., 10-isopropenyl.

The substituted dihydrobenzofuran and spirobenzofuran-2(3H)-cyclohexane compounds of the present invention of the general formulae 3, 4, the synthetic intermediates of the general formula 5, and the salts thereof exhibit complement inhibition, as manifested by inhibition of complement-mediated C5a production and/or inhibition of complement-mediated hemolysis. The complement-inhibitory properties of the compounds of the invention can be evaluated by modification of known techniques, e.g., the assay described in Section 6.6.1, infra.

Treatment of the compounds of the present invention with appropriate basic reagents provides pharmaceutically acceptable salts thereof. When a carboxylic acid group is present in the compounds of the invention, a pharmaceutically acceptable ester can also be prepared by treatment with a suitable esterifying group under appropriate conditions.

5.2. SYNTHETIC PROCESSES

Processes are provided which comprise chemical steps for the synthesis of the compounds of the invention.

Such processes of the invention are diagrammed in detail in Scheme 1 (See infra Section 5.2.2). The synthetic scheme depicted in Scheme 1 provides a shorter and more flexible route than one based on the syntheses of K-76 (Corey and Das J. Am. Chem. Soc. 1982, 104, 5551; McMurray et al. J. Am.Chem. Soc. 1985, 107, 2712). Retrosynthetic evaluation of all the final compounds produced according to Scheme 1 ultimately results in two fragments; an aliphatic and an aromatic portion. These two portions can be joined by using regioselective ortho-lithiation and subsequent alkylation. Two different strategies can then be employed for the production of the final compound of the invention: initial cyclization followed by aromatic functionalization or vice versa.

5.2.1. PREPARATION OF COMPOUNDS OF GENERAL FORMULA 5

The intermediates of the general formula 5 of the invention can be prepared by various methods depending on the types of substituents present therein.

The aliphatic substituent, $R_6$, of compounds of the general formula 5 are derived from suitable alkylating agents. For example, 1-bromomethylcyclohexene, 6a, can be used as the starting material for the preparation of compound 5a. Compound 6a can in turn be prepared from cyclohexanone or directly from alkyl cyclohexenecarboxylate, according to a known precess (Wheeler, O. H. and Lerner, I. J. Am. Chem. Soc. 1956, 78, 63; Adams, R. and Thai, A. F. Org. Synth. 1932, 1, 270; Lythgoe, B. et al. J. Chem. Soc. 1956, 406). In a particular example, cyclohexanone is converted to its cyanohydrin, then dehydrated to the cyanoalkene, followed by alcoholysis to an alkyl cycloalkenecarboxylate. Lithium aluminum hydride reduction of the ester followed by halogenation with phosphorus trihalide provides compound 6a.

Limonenyl chloride, 6b, is obtained readily from limonenyl alcohol by the action of triphenylphosphine in excess halogenated solvent. This conversion provides optically active allylic halide from optically active limonenyl alcohol. A procedure analogous to that developed by Crawford and co-workers (J. Am. Chem. Soc. 1972, 94, 4298) is used to prepare optically active alcohol by the sequential lithiation of commercially available homochiral limonene, oxygenation, and reduction of the resultant hydroperoxide with aqueous sodium sulfite.

A third halointermediate, 6c, is derived from a multistep sequence starting from optically active R-(-)- ) or S-(+)-carvone. The steps of the synthesis involve reduction of the α,β-unsaturated ketone to the allylic alcohol, epoxidation, reduction to the diol, acetonide formation, and treatment of the unsaturated acetonide with calcium hypochlorite to yield the allylic chloride. The coupling reaction is generally carried out immediately after purification of these unstable allylic halides.

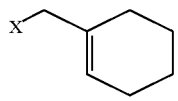

6a

6b

6c

The aromatic segment of the compounds of the general formula 5 is obtained from substituted alkoxyphenols or resorcinols. For example, 3-methoxymethoxyanisole, 7, is obtained from the reaction of 3-methoxyphenol with chloromethyl methyl ether in a stirred suspension of anhydrous potassium carbonate in acetonitrile (Rall, G. J. H. et al. Tet. Lett. 1976, 1033). Anhydrous conditions and the proper ratio of substrate to solvent are critical to the success of this reaction. For reactions employing quantities of reagents above 5 grams, a useful alternative procedure uses the preformed sodium aryloxide, chloromethyl methyl ether, and dimethylformade as solvent (See, Rall, G. J. H. et al. supra).

7

The group R of formulae 5 and 5a–c should be stable to cleavage under the conditions used to hydrolyze or remove the protecting group Rs and the subsequent cyclization of the resulting free phenol according to steps 3 or 4 of Scheme 1. In addition, Rs is preferably a potentially chelating group which can promote the regioselective ortho-metalation required to introduce substituents $R_2$ and $R_6$ of formula 5. Compound 7 embodies the preferred protecting groups for resorcinol (R=methyl and $R_5$=methoxymethyl). The methoxymethyl or MOM ethers can be easily removed in the presence of methyl ethers (Narasimhan, N. S. et al. Synthesis 1979, 906), and the ortho directing power of the MOM group has been shown to be greater than that of a methyl ether (Ronald R. C. Tet. Lett. 1975, 3973).

In an alternative embodiment, the commercially available compound 3,5-dimethoxybenzyl alcohol, 8, can be used as the aromatic segment for coupling to the allylic halide (See Scheme 2, infra).

8

The efficacy of the coupling reaction between the metalated aromatic segment and the aliphatic group is greatly influenced by a number of factors including the degree of aggregation of the metalating species, typically an alkyl-lithium reagent (Gschwend, H. W. and Rodriguez, H. R. Org. React. 1979, 26, 1). The choice of solvent and any additives such as N,N,N',N'-tetramethylethylenediamine (TMEDA) or hexamethylphosphoric triamide (HMPA), in turn, strongly influences this aggregation state. Solvent(s), additive(s), temperature, reaction time, and reagent stoichiometries for coupling the respective substrates should be optimized. Suitable solvents include anhydrous aprotic organic solvents such as tetrahydrofuran (THF), diethyl ether (Et$_2$O), dioxane, and diglyme. Surprisingly, we have discovered that dry hexane is a preferred solvent for selective metalation ortho to a chelating group like OMOM and lithioalkoxymethyl (kinetic conditions), while THF/TMEDA solvent mixtures, generally, provide for metalation at the thermodynamic site, between the two inductively electron-withdrawing methoxy groups in 8, for example. In one particular embodiment, n-butyllithium (n-BuLi) in THF/TMEDA or hexane/TMEDA allows for the coupling of aromatic segment 7 with allylic bromide 6a; however, only THF/TMEDA allows coupling of 6a with aromatic segment 8 at the desired 4-position (thermodynamic). When the coupling between 6a and 8 is carried out in hexane, lithiation and coupling occurs in the 2-position of 8 (the kinetically favored position).

The aromatic substrate is dissolved in the solvent such as dry THF and the like. The TMEDA is then added and is preferably approximately equimolar to the amount of alkyllithium used. In a preferred embodiment, the amount of alkyllithium (RLi) slowly added at 0° C. is approximately 1.1 equivalents per equivalent of a compound of the type such as 7 and is approximately 2.2 equivalents per equivalent of a substrate such as 8 that has an additional acidic hydrogen. Moreover, the addition of approximately 1.2 equivalents of a copper salt per equivalent of the lithiated aromatic substrate is preferred to obtain optimum yields from the coupling reaction. Most sources of copper (I) are suitable including cuprous bromide d imethylsulfide, tetrakis (acetonitrile) copper (I) tetrafluoroborate, and the cuprous halides. The use of cuprous iodide is preferred.

Careful control of temperature is important for the success of the aromatic alkylation. While the lithiation is carried out at zero degree to ambient temperature, the subsequent reactions are carried out at low temperature. In a preferred example, the aryllithium reagent is cooled to −78° C. followed by the addition of copper (I) salt. The resulting mixture is subsequently stirred at −40° C., a temperature at which the corresponding arylcuprate species can form and is relatively stable. The copper reagent is then recooled to −78° C. prior to the addition of the electrophile. Carrying out the the addition at higher temperatures can diminish the yields of coupled products such as 5. It is important that all manipulations discussed supra be performed in the absence of oxygen and moisture, and are preferably carried out under an inert atmosphere such as dry nitrogen or argon.

The product mixture which is obtained from the coupling reaction can then be worked up by washing several times with a moderately basic aqueous solution, e.g., saturated aqueous sodium bicarbonate (NaHCO$_3$). The organic phase can be dried by shaking with a drying agent such as magnesium sulfate, filtered from any solids, and concentrated under a mild vaccum to provide the crude product. Further purification may then be effected by procedures typically employed in the art (e.g., fractional distillation, fractional crystallization, or chromatographic separation).

5.2.2. PREPARATION OF COMPOUNDS OF THE GENERAL FORMULAE (3 AND 4)

Substituted dihydrobenzofuran derivatives of the general formula 3 with substituents OR and R$_1$–R$_4$ as defined supra in Section 5.1 can be obtained by the metalation and subsequent alkylation of coupled intermediates such as those described in the preceding section, followed by hydrolysis of the protecting groups and cyclizaiton of the ene-phenol. This synthetic pathway is illustrated in Scheme 1, infra.

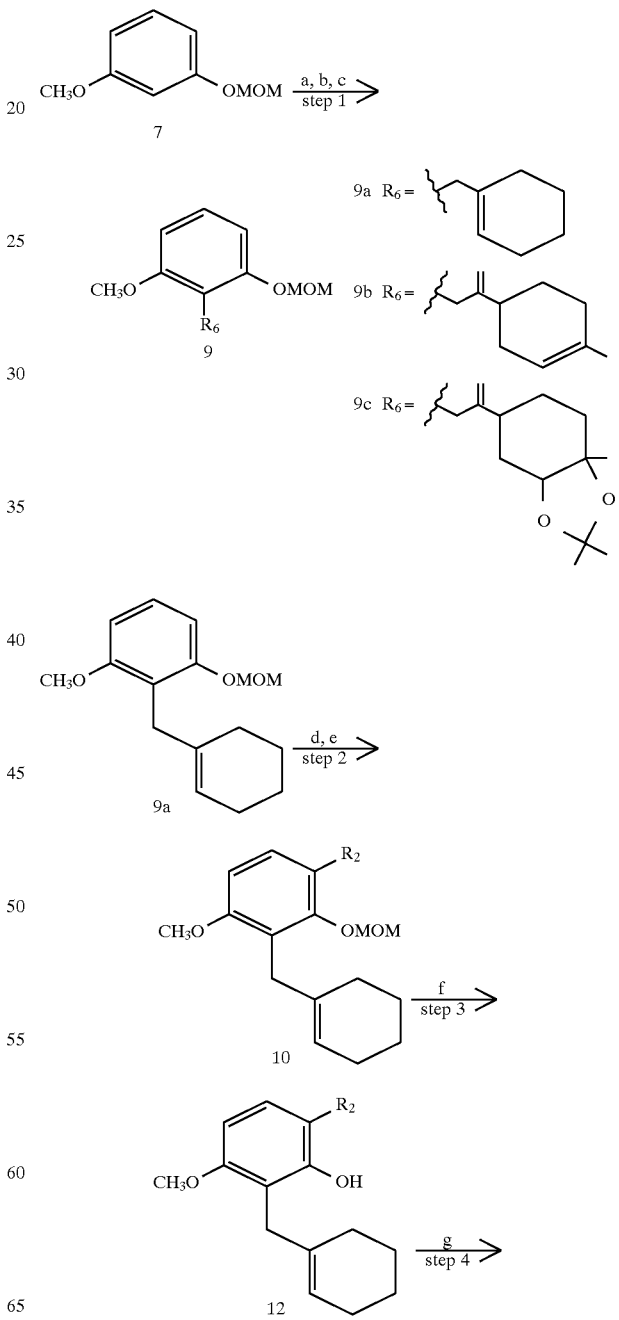

Scheme 1

-continued
Scheme 1

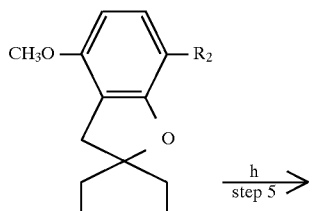

11

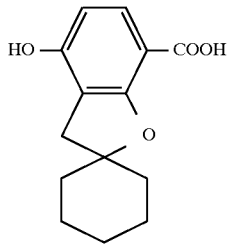

14a
(4, R, R₁ = H, R₂ = COOH)

(a) ⁿBuLi, THF/TMEDA; (b) CuI; (c) R₆X; (d) ⁿBuLi, Hexane/TMEDA;
(e) E⁺(R₂); (f) H⁺, ⁱPrOH; (g) Amberlyst resin;
(h) ⁱBuSLi, HMPA

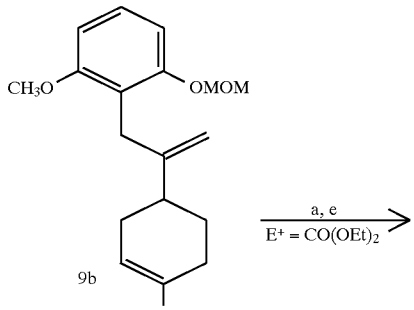

9b

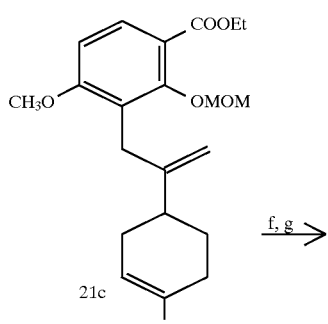

21c

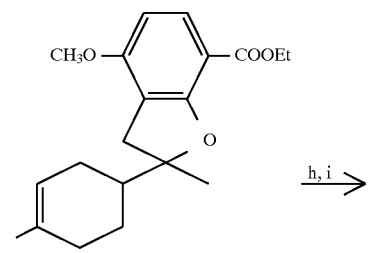

20c

-continued
Scheme 1

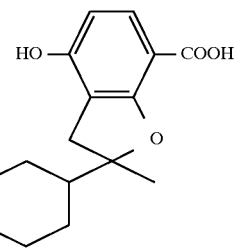

23a (3, R. R₁ = H. R₂ = COOH. R₃ = CH₃.
R₄ = 1-methylcyclohexan-4-v;)
(a) ⁿBuLi, THF/TMEDA; (b) CuI; (c) R₆X; (d) ⁿBuLi, Hexane/TMEDA;
(e) E⁺(R₂); (f) H⁺, ⁱPrOH; (g) Amberlyst resin;
(h) ⁱBuSLi, HMPA; (i) aq 40% KOH In a preferred embodiment, the protected resorcinol is lithiated and alkylated in step 1 of Scheme 1 using the allylic bromide 6a as the electrophile. The resulting coupled product 9a can then be dissolved in dry hexane and treated dropwise with alkyllithium in the presence of TMEDA (step 2) at 0° C. Cooling the reaction mixture to −78° C. and addition of the desired electrophile introduces the $R_2$ substituent at this stage.

Generally, the MOM protecting group of intermediates such as 9, with or without the $R_2$ substituent, may be hydrolyzed by stirring the compound in 5% hydrochloric acid (HCl)/ether mixtures overnight. Deprotection to the free phenol may also be effected by a solvent mixture comprised of 4N HCl/ⁱPrOH, especially for carboxaldehyde containing derivatives, which need to be stirred for several days. The cyclization step can be achieved most conveniently by stirring the substrate in the presence of Amberlyst resin in a non-polar solvent followed by filtration. In this particular process, the resin is washed with fresh solvent, and the filtrates are combined and concentrated to give the desired crude cyclized product in good yield. In the particular case where $R_2$=—COOH in intermediate 10a (Scheme 1, step 2, E⁺=$CO_2$), the cyclization of the phenol (steps 3 and 4) can be achieved by stirring with Amberlyst resin in benzene for 24–72 hours at room temperature. Some difficulty is encountered in the cyclization of intermediates with hydroxymethyl substituents (e.g., $R_2$=−$CH_2OH$). A different route is preferred for synthesis of cyclized products with this substituent (see below).

As discussed supra, a variety of $R_2$ substituents may be introduced before the cyclization step. For example, addition of the following electrophiles to the aryllithium species produces the indicated functional group (these examples serve only to illustrate a possible technique and are not meant to be limiting): carbon dioxide (carboxyl); ethyl chloroformate or diethyl carbonate (carbethoxy); dimethylformide (formyl); methylisocyanate (N-methylcarbamoyl); tert-butylisocyanate (N-tert-butylcarbamoyl); paraformaldehyde (hydroxymethyl); trifluoroacetic anhydride (trifluoroacetyl); bromine (bromide); chlorine (chloride); iodine (iodide); substituted vinyl iodides (substituted vinyl group). Other compounds may, in turn, be obtained by modification of these functional groups by known methods.

The cyclized methyl ether derivatives of the type, 11, can be converted to the free phenols, 14 (Scheme 1, step 5), by known methods. These procedures include but are not limited to treatment of the methyl ether with boron trihalides (McOmie, J. F. W. and West, D. E. Org. Synth. 1973, 5, 412; Grieco, P. A. et al. J. Org. Chem. 1975, 40 1450), boron trifluoride in the presence of thiols (Fujita, E. et al. Ibid.

1979, 44, 1661; Fujita, E. J. Chem. Soc. Perkin Trans. 1 1976, 44, 4444), and lithium tert-butylthiolate salts (t-BuSLi) in hexamethylphosphoric triamide (McMurry, J. E. and Erion, M. D. J. Am. Chem. Soc. 1985, 107, 2712). The use of t-BuSLi is preferred.

Open-chain coupled products such as 9b or 9c (See Scheme 1) give rise to compounds such as 21 or 25, respectively. The latter intermediates, wherein the olefinic bond involved in the cyclization is exocyclic, or other derivatives containing simple unsaturated aliphatic groups, produce dihydrobenzofuran derivatives disubstituted at the 2-position upon deprotection and treatment with Amberlyst ion-exchange resin (See e.g., 20).

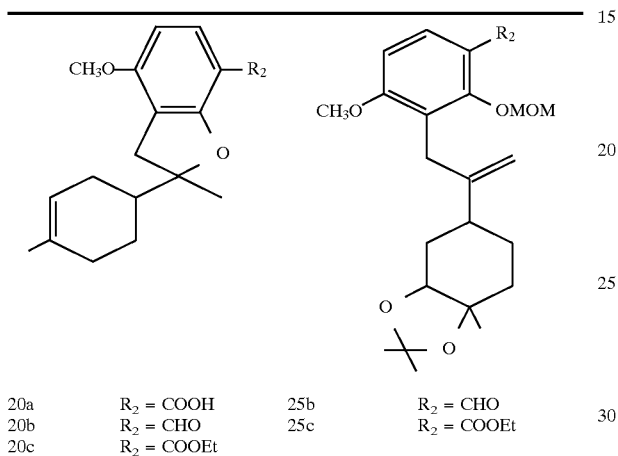

| 20a | $R_2$ = COOH | 25b | $R_2$ = CHO |
| 20b | $R_2$ = CHO | 25c | $R_2$ = COOEt |
| 20c | $R_2$ = COOEt | | |

Slightly more complex analogs containing a diol group, such as 24 or 27, infra, can be obtained in this manner.

The use of 3,5-dimethoxybenzyl alcohol, 8, as the starting aromatic component has the advantage of having the $R_1$ substituent already in place. Compound 8 is dissolved in THF and is treated at 0° C. with 2.0 equivalents of n-butyllithium in the presence of TMEDA (2.0 equiv). The benzyl alcohol is lithiated predominantly at the 4-position after about 2 hours. Formation of the arylcuprate at −40° C. and addition of the alkylating agent completes the synthesis of 13 (Scheme 2, step 1) with a small amount of the isomer 13' also being formed. Fractional crystallizaiton of the product mixture provides pure 13.

As previously alluded to, cyclization of intermediates with hydroxymethyl substituents can be problematic. In one embodiment, a remedy to this problem involves converting the benzyl alcohol 13c to the formyl compound 13b (See Scheme 2, step 2). This procedure can be accomplished by a Swern oxidation or, more preferrably, by using pyridinium chlorochromate in "buffered" methylene chloride. One of the symmetrical methyl ethers is then selectively cleaved (step 3) and cyclized in the normal fashion to yield the 6-substituted formyl analog 30b. Oxidation of the formyl group to the carboxylic acid (e.g., 30a or 31a) can be effected by a number of reagents either before or after the cyclization of step 4. Suitable inorganic oxidizing agents include but are not restricted to permanganate salts, manganese oxide, chromic acid, chromate salts, silver oxide, silver nitrate, nickel peroxide, and cerium salts such as cerium sulfate, cerium oxide and cerium perchlorate. Silver oxide is preferred. The benzyl alcohol, 30c (4, R=CH$_3$, R$_1$=CH$_2$OH, and R$_2$=H), obtained by reduction of 30b using, for example, such reducing agents as lithium aluminum hydride, or diborane, preferably in an appropriate solvent such as ether, e.g., THF, dioxane, or diethyl ether.

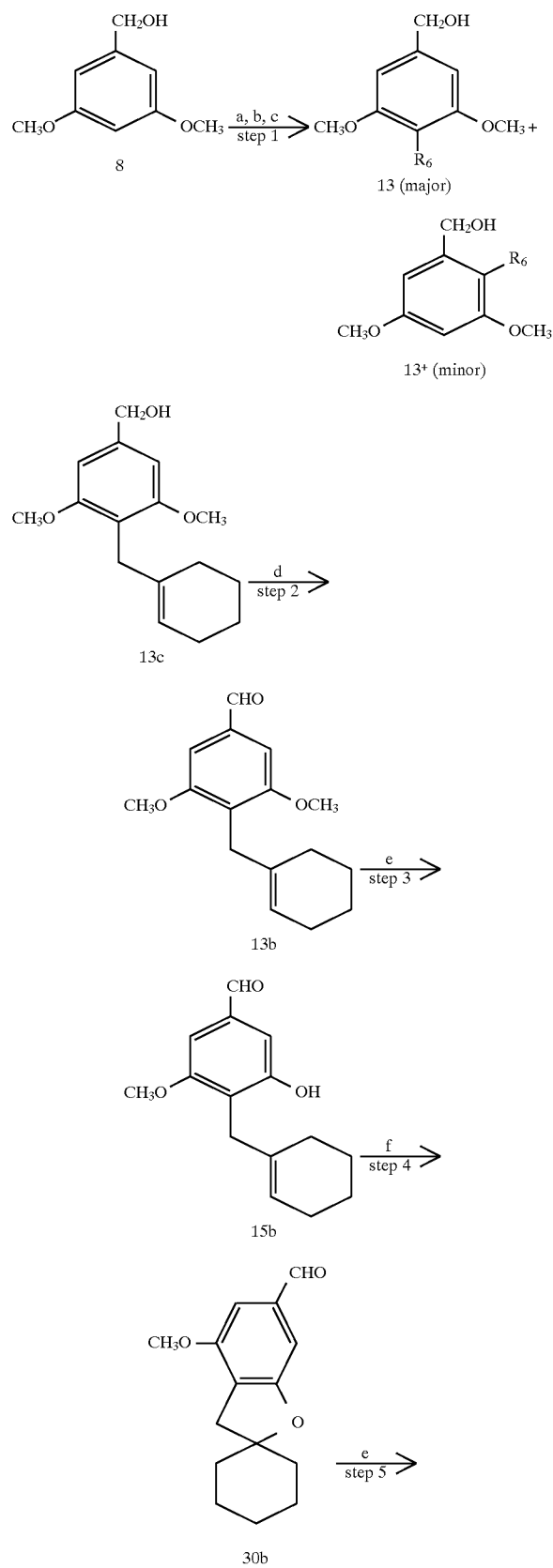

-continued
Scheme 2

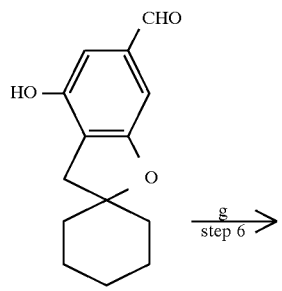

31b

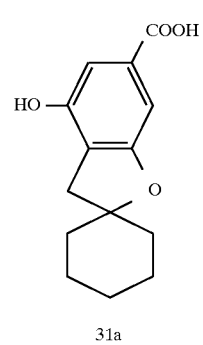

31a (a) nBuLi, THF/TMEDA; (b) CuI; (c) R₆X; (d) PCC, NaOAc, CH₂Cl₂;
(e) ¹BuSLi, HMPA; (f) Amberlyst resin; (g) Ag₂O, aq. 5% NaOH Even more complex dihydrobenzofuran-based compounds can be obtained by further modification of the analogs described above. Any of the compounds containing the methyl ether groups at the 4-position of the dihydrobenzofuran skeleton can be cleaved by one of the boron or thiolate reagents mentioned supra. Sometimes, as in the limonene series, it may be desirable to carry out the demethylation of the methyl ether with the carboxylic acid group at the 7-position protected as its alkyl ester (See, e.g., Scheme 1). Open positions in the phenyl ring may be metalated and functionalized as disclosed previously. The double bond of compound 20a can be hydroxylated by transition metal oxide reagents such as potassium permanganate or osmium tetroxide. The combination of methyl-ether cleaveage and hydroxylation of 20a, for example, would give compound 24a. Alternatively, compound 24a may be obtained by demethylation of intermediate 27c to the free phenol. In those instances, as in here, where an alkyl

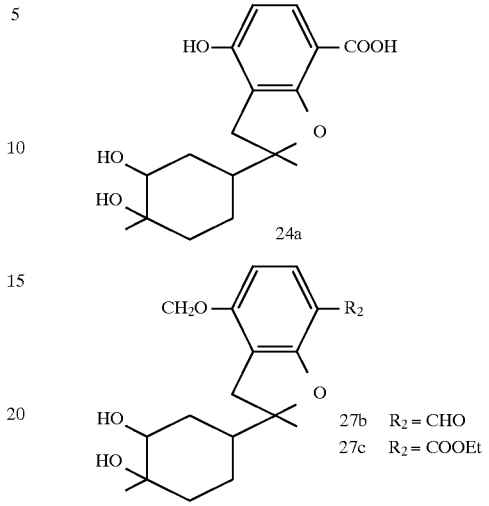

ester is employed to protect the carboxylic acid group at the 7-position, an alkaline, hydrolysis step may be necessary to obtain the free carboxylic acid (Scheme 1, step i). Other modifications can be envisioned which do not depart significantly from the scope and essence of the products of the present invention. Transformations such as epoxidation of the double bond, hydroxylation at the allylic position of the double bond, oxidate cleavage of the double bond, hydroformylations, and modifications of the products obtained therefrom are but a few non-limiting examples.

5.2.3. PREPARATION OF COMPOUNDS OF GENERAL FORMULA 6-CARBOXYL-4-SUBSTITUTED SPIRO[BENZOFURAN -2(3H)-CYCLOHEXANES]

6-carboxyl spiro[benzofuran-2(3H)-cyclohexane] moleules that are also substituted at the 4 position to form a series of ether substituted derivatives can be prepared as shown in Schemes 3 and 4 below and as more fully described in Section 7 infra.

Scheme 3

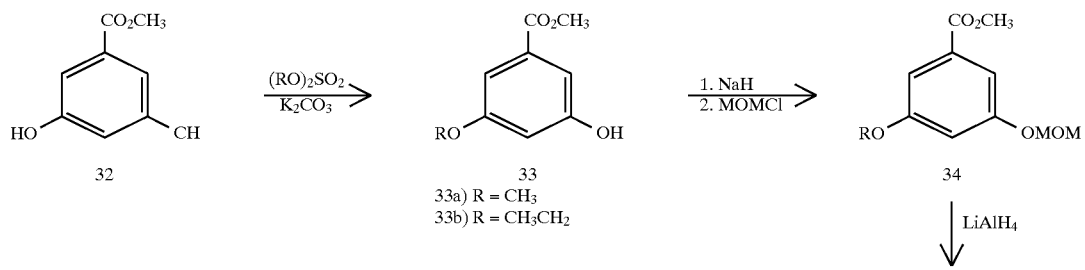

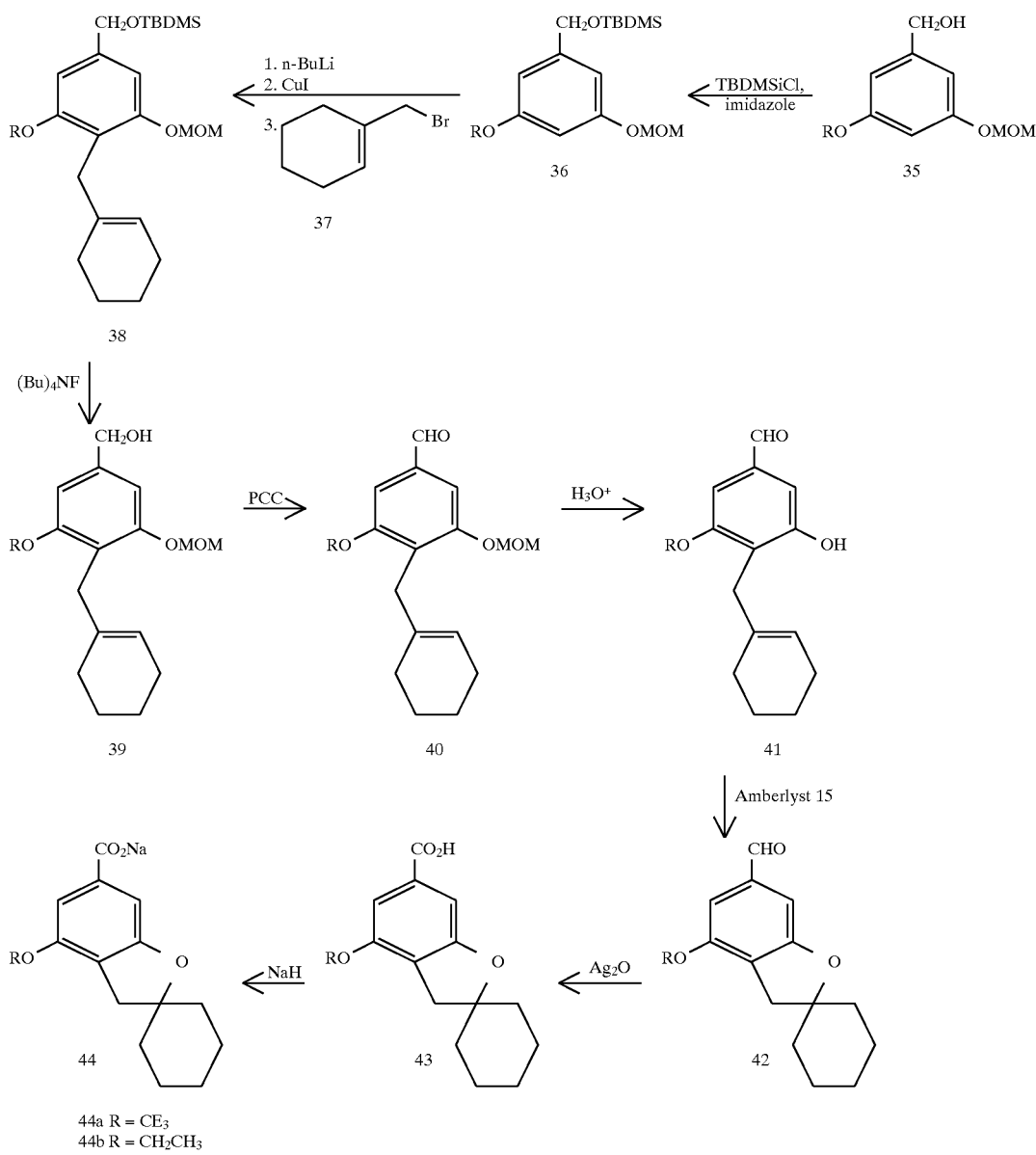
Scheme 4
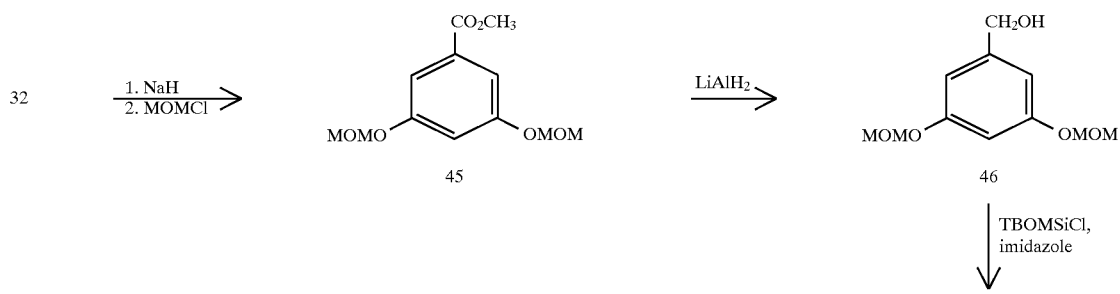

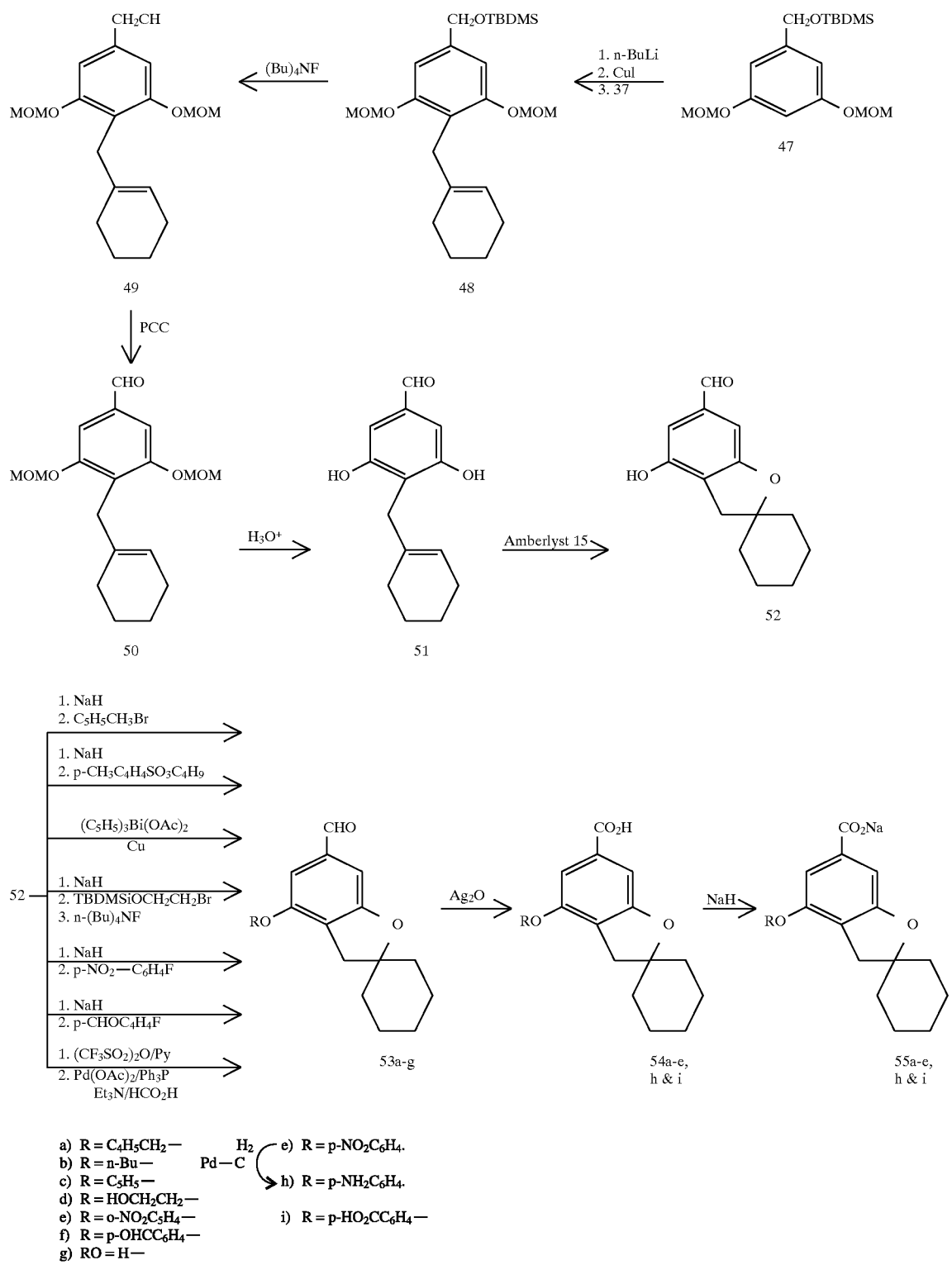

These compounds and the salts thereof exhibit complement inhibition as manifested by inhibition of complement mediated hemolysis. Other complement-inhibitory properties of these compounds can be evaluated by known techniques as described in Sections 6.6.1 and 10.2 to 10.4 and by numerous complement assay techniques that are known in the art. Substituents for R in position 4 of compounds of the general formula 4 include a hydrogen atom or a lower alkyl group (e.g. $CH_3$—, $CH_3CH_2$—, n—Bu—), a functionalized lower alkyl group (e.g. $HOCH_2CH_2$—), a benzyl or substituted benzyl group, a phenyl or substituted phenyl group (e.g. $C_6H_5CH_2$—, $C_6H_5$—, p—$NO_2C_6H_4$—, p-$CHOC_6H_4$—, p—$NO_2C_6$—, and p—$NH_2C_6H_4$—). In addition the OR at position 4 of compounds of the general formula 4 can instead be H—. Preferred substitutions at position 4 are exemplified by compounds 4b, 55c and 55e, which are more effective in inhibiting complement mediated hemolysis than is K76COOH.

5.2.4. PREPARATION OF COMPOUNDS OF GENERAL FORMULA 6,7-DISUBSTITUTED-4-METHOXYSPIRO [BENZOFURAN-2(3H)-CYCLOHEXANES]

6,7-disubstituted spiro[benzofuran-2(3H)-cyclohexane] molecules can be prepared as shown in Schemes 5 and 6 below and as more fully described in Section 8 infra.

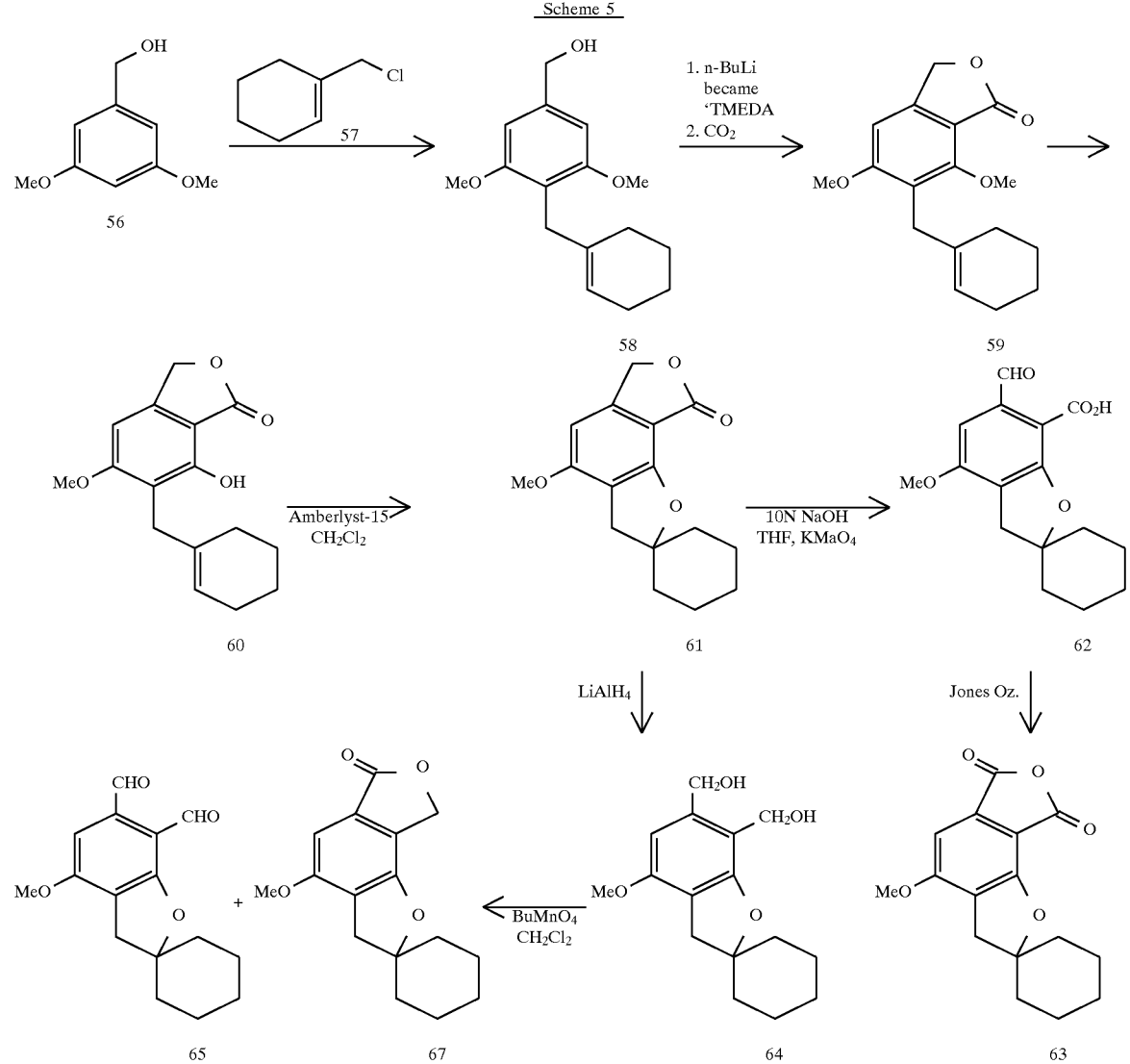

Scheme 5

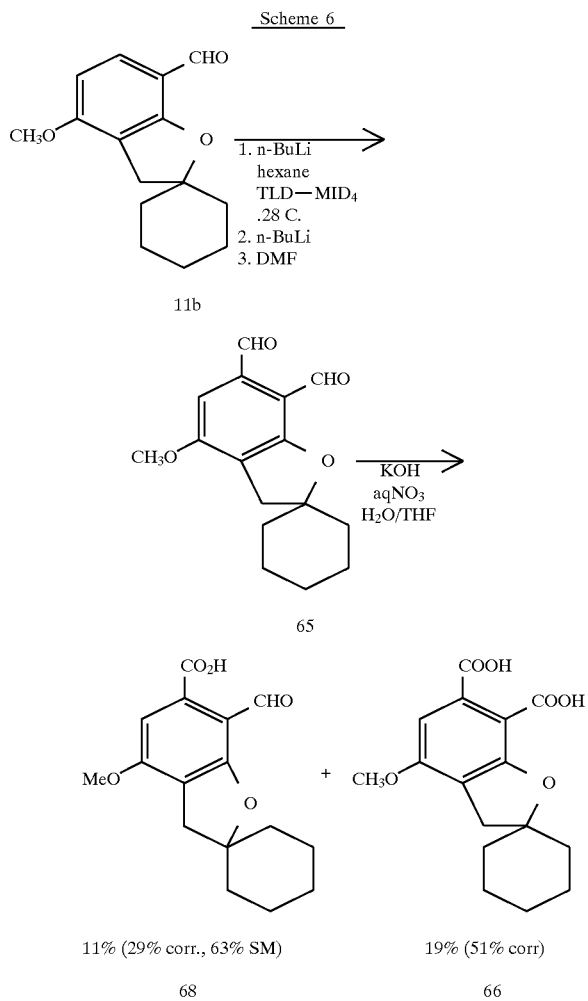

Scheme 6

11b
65
11% (29% corr., 63% SM)
68
19% (51% corr)
66

The naturally occurring compound K76 has disubstituted formyl groups in positions 6 and 7 of the ring D as shown below. Its oxidized derivative K76COOH has a carboxyl group at position 6 and a formyl group at position 7.

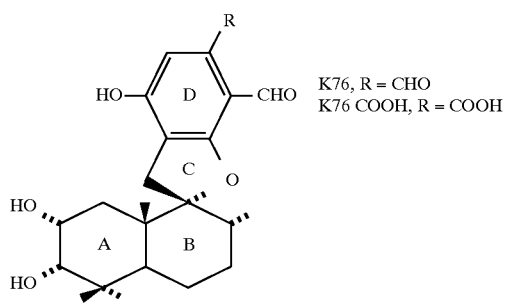

K76, R = CHO
K76 COOH, R = COOH

The compounds of this section differ from K76, since they represent disubstituted BCD analogues lacking the A ring structure of K76. In addition the compounds of this section can also be substituted at position 4 of the D ring to form trisubstituted BCD analogues. These di- and tri-substituted compounds and the salts thereof exhibit complement inhibition as manifested by inhibition of complement mediated hemolysis. other complement-inhibitory properties of these compounds can be evaluated by known techniques as described in Sections 6.6.1 and 10.2 to 10.4 and by numerous complement assay techniques that are known in the art.

The $R_1$ and $R_2$ groups can be any combination of the following: a hydrogen atom, a carboxylic acid group, a formyl group; a hydroxymethyl group, an N-(lower alkyl) carbamoyl group, a trifluoroacetyl group, a carbalkoxy group, a halide group, a vinyl group, a substituted vinyl group having up to 10 carbon atoms, an alkylidene group having up to 20 carbons, an aliphatic acyl group, a substituted aliphatic acyl group, an aromatic group, a substituted aromatic acyl group, a trifluoroacetyl group, a sulfamoyl group, an N-acylcarbamoyl group, a tetrazole group, a tertiary aliphatic amine group, an oxazoline group, an amidine group, or a hydrazone group.

Specific substitutions for R1 and R2 groups include —CHO, —CH$_2$OH, —COOH, COCF$_3$, SO$_2$NH$_2$ and tetrazole, oxazoline, imide or CH$_2$NMe$_2$ derivatives. Substitutions at positions 6 and 7 can be cyclic compounds as exemplified by compounds 62 and 68. The presence of polar groups in the 6 and 7 positions appears to affect complement inhibition activity, perhaps because such polar groups interact with regions of the complement receptors.

Specific compounds include compounds of general formula 4 in which R can vary generally as described above; $R_1$ is a carboxyl group or a bioisosteric acid group (such as sulfonamide, imide, or tetrazole) or a bioisosteric basic group (such as a tertiary aliphatic amine, oxazoline, amidine, or hydrazone), or a bioisosteric neutral group (such as trifluoroacetyl); $R_2$ is a formyl group or a bioisosteric group such as methyl ketone (acetyl), other alkyl ketone, aryl ketone or other similar group.

A preferred organic compound of the compositions of this invention is the 4,6,7 trisubstituted spiro[benzofuran-2(3)H cyclohexane] such as compound 68 (6-carboxy-7-formyl-4-methoxyspiro[benzofuran-2(3H)-cyclohexane]) and 6-carboxy-7-formyl-4-phenoxy-spiro[benzofuran-2(3H)-cyclohexane]. In a specific embodiment, compound 68 exhibits a relatively large amount of complement inhibition in the hemolysis assay. Even more inhibitory compounds can be produced by combining the optimal subsitutions at the 4 position with the 6,7 disubstitutions present in 68. In a preferred embodiment, a phenoxy group is substituted at the 4 position.

5.3. DEMONSTRATION OF COMPLEMENT INHIBITION

The compounds of the invention can be assayed by any techniques known in the art in order to demonstrate their complement inhibiting activity. Such assays include but are not limited to the following in vitro tests for the ability to inhibit complement system activity or to selectively inhibit the generation of complement-derived peptides (See Sections 6.6 and 10.3 for specific examples):

(i) measurement of inhibition of complement-mediated lysis of red blood cells (hemolysis);

(ii) measurement of ability to inhibit formation of C5a and C5a des Arg and/or measurement of ability to-inhibit formation of C3a and C3a des Arg;

(iii) inhibition of alternative pathway mediated hemolysis.

Those compounds which are demonstrated to have significant complement-inhibiting activity can be therapeutically valuable for the treatment or prevention of diseases or such as those described in Section 5.5, infra.

5.4. IMMUNOSUPPRESSIVE ACTIVITY

The compounds of the present invention can inhibit immune activity. In particular, the compounds of the invention inhibit cell-mediated immune function. For example, the compounds can suppress natural killer activity, inhibit the proliferation of peripheral blood lymphocytes, and/or inhibit the activation of T lymphocytes in PBL culture.

Any procedure known in the art may be employed to demonstrate immunosuppressive activity. Such procedures include but are not limited to in vitro assays for inhibition of natural killer lysis of target cells, inhibition of proliferation of peripheral blood lymphocytes or inhibition of cell surface interleukin-2 receptor expression. Specific embodiments of assay procedures which can be used are detailed in the examples sections infra (See Subsections 6.7.1 through 6.7.4).

5.5. THERAPEUTIC USES OF THE COMPOUNDS OF THE INVENTION

The compounds of the invention which exhibit complement and/or immune activity inhibition have therapeutic value in the prevention or treatment of various immune or inflammatory diseases or disorders. The compounds of the invention may be administered to a patient for treatment of an immune disorder involving undesirable or inappropriate complement activity. In particular, an effective dose of an inhibitive compound of the invention may be therapeutically applied to ameliorate or to prevent a detrimental effect caused by the activity of a component of the complement system (e.g., C5a) or an inappropriately reactive immune system. An effective dose of the compound of the invention for the treatment of a disorder involving undesirable or inappropriate complement activity or an immune disorder can be determined by standard means known in the art taking into account routine safety studies, toxicity studies, dose concentration studies and method of delivery, e.g., bolus, continuous or repeated. In a particular embodiment, a dose of about 0.01 to about 500 mg/kg can be administered.

The diseases or disorders which may be treated by the compounds of the invention include but are not limited to those listed in Table III, supra. In particular, those disorders associated with extended zones of tissue destruction due to burn- or myocardial infarct-induced trauma, and adult respiratory distress syndrome (ARDS), also known as shock lung, can be treated by administration of an effective amount of the compounds.

Detrimental nonspecific activation of the complement system, or unfavorable activation by the alternative pathway, can also be prevented or treated by compounds of the invention. In specific embodiments, such compounds can ameliorate the acute pathological changes induced by specific or non-specific proteolytic processing of C5.

The compounds of the invention may also be used to modulate biologic or immune functions directly or indirectly mediated by the complement system, which can include but are not limited to those functions listed in Tables I and II, supra, and the in vivo correlates of the in vitro functions therein.

In particular embodiments, the inhibitive compounds can be used to treat inflammation associated with, for example, kidney stones, systemic lupus erythematosis (SLE), nephrotoxic glomeronephritis, or multiple sclerosis (See, e.g., Experimental Allergic Encephalomyelitis. A Useful Model for Multiple Sclerosis, A Satellite Conference of the International Society of Neurochemists, Jul. 16–19, 1983, University of Washington, Seattle, Wash.; Miyazaki, W. et al. Microbiol. Immunol. 1980, 24, 1091; Konno, S. and Tsurutuji, S. *Sr. J. Pharmacol.* 1983, 80, 269).

In yet another embodiment, the compounds of the invention can be administered for treatment of tissue damage due to myocardial ischemia and reperfusion, resulting from neutrophils attracted by and activated by the complement system.

The compounds of the invention may also be administered for the prevention or treatment of diseases or disorders caused or accompanied by increased lymphocyte or natural killer activity, including but not limited to atrophic gastritus, thyroiditis, allergic encephalomyelitits, gastric mucosa, thyrotoxicosis, autoimmune hemolytic anemia, pemphigus vulgaris, sympathetic opthalmia, delayed-type hypersensitivity, rejection of allografts, graft-host reaction, organ transplant rejection, other autoimmune disorders, and drug allergies. They can also be used to alleviate the adverse effects of complement activation caused by therapeutic intervention such as tissue plasminogen activator therapy or cardiopulmonary bypass.

Pharmaceutical compositions comprising the inhibitive compounds or the salts thereof are provided by the present invention. Such compositions comprise a therapeutically effective amount of the compound and a pharmaceutically acceptable carrier. Such a carrier includes but is not limited to saline, buffered saline, dextrose, and water. A pharmaceutical kit comprising one or more containers filled with one or more of the ingredients of the pharmaceutical composition is also within the scope of the invention.

Various delivery systems (e.g., encapsulation in liposomes, microparticles, or microcapsules, conjugation to specific molecules) are known and can be used for therapeutic delivery of the compounds. Methods of administration include but are not limited to oral, intradermal, transdermal, intravenous, subcutaneous, intramuscular, intraperitoneal, and intranasal routes. Such administration can be done in either bolus or repeat doses or continuously by infusion for instance.

A further embodiment of this invention includes the combined therapy that can be obtained by treating patients with disorders (e.g. myocardial infarction patients) that are routinely treated with thrombolytic agents such as tissue plasminogen activator, streptokinase or urokinase with a combination of the compounds of this invention and the routinely administered thrombolytic compounds or a fibrinolytically active fragment, derivative, or modified version thereof. The usefulness of such a combined therapy derives from the observation that the complement system is activated in disorders such as myocardial infarction or bypass surgery. The efficacy of a combined treatment could be substantially better than the thrombolytic treatment alone due to the ability of the complement inhibitory compounds to modulate the inappropriate and damaging complement activation. The administration of the thrombolytic and complement inhibitory compounds can be simultaneous or sequential or in different dose forms including combinations of oral dose forms with injectables to name just a few.

The invention can be better understood by referring to the following examples which are given for illustrative purposes only and are not meant to limit the invention.

6. EXAMPLES

6.1. 2-(1'-CYCLOHEXENYL)METHYL-3-METHOXYMETHOXYANISOLE (9a)

The 3-methoxymethoxyanisole, 7, was obtained in 96% yield by the following procedure. A mixture of finely powdered anhdryous potassium carbonate ($K_2CO_3$; 2.0 equiv) and 3-methoxyphenol (1.0 equiv) in dry acetonitrile was stirred at 0° C. for 15 minutes under nitrogen. To ensure that the reaction pH remained above six, 100 ml of acetonitrile were used per gram of phenol substrate. A catalytic amount of 18-crown-6 (0.12 equiv) was added, and the mixture was stirred an additional 15 minutes at 0° C. Neat chloromethyl methyl ether (1.5 equiv) was then introduced slowly. The suspension was allowed to warm up to ambient temperature and stirred for 6 hours. After this time, the mixture was recooled to 0° C., and one-half the original quantities of $K_2CO_3$, 18-crown-6, and $CH_3OCH_2Cl$ were added. After another 4 hours of stirring at room temperature, the suspension was filtered and the filtrate was concentrated under reduced pressure. The residue was dissolved in ethyl either ($Et_2O$), washed with 5% sodium hydroxide (3×50 ml), concentrated in vacuo, and distilled under reduced pressure. Compound 7 was obtained as a clear colorless liquid. Bp 45° C. (0.15 mm Hg). $^1H$ NMR (90 MHz, deuteriochloroform) δ 7.16 (1H, m), 6.61 (3H, m), 5.16 (2H, s), 3.79 (3H, s), and 3.49 (3H, s) in ppm downfield from TMS. $^{13}C$ NMR ($CDCl_3$) δ 160.5,m 158.2, 129.7, 108.2, 107.3, 102.5, 94.3, 55.9, and 55.1 in ppm downfield from TMS.

n-BuLi (1.1 equiv) was added slowly to a THF solution of compound 7 (1.0 equiv) and TMEDA (1.1 equiv), at 0° C. under a nitrogen atmosphere. The solution was stirred at room temperature for 2–5 hours and then cooled to –78° C. Cuprous iodide (1.2 equiv.) was added all at once. The light gray suspension was warmed up to –40° C., and after stirring for 1.5 hours, turned into a green-gray color. The copper reagent was cooled to –78° C. and allowed to react with a THF solution of freshly-prepared allylic bromide 6a (1.3 equiv). The reaction mixture was allowed to warm up to ambient temperature gradually and stirred for up to 72 hours. The mixture was quenched and washed with a saturated aqueous solution of sodium bicarbonate until the aqueous layer became colorless. The organic layer was dried by passage through a plug of potassium carbonate and concentrated in vacuo to give a dark orange soil. The crude product was distilled under reduced pressure to provide compound 9a in 69% yield. Bp 105° C. (0.15 mm Hg). Anal. Caqlcd. for $C_{16}H_{22}O_3$: C, 73.25; H, 8.45. Found: C, 73.13; H, 8.50. $^1H$ NMR (90 MHz, $CDCL_3$) δ 7.03 (1H, t, J=8 Hz), 6.71 (1H, d, J=8 Hz), 6.54 (1H, d, J= 8 Hz), 5.23 (1H, broad s), 5.13 (2H, s), 3.77 (3H, s), 3.43 (3H, s) 3,32 (3H, broad s), 1.95 (4H, m), and 1.57 (4H, m) in ppm downfield from TMS. $^{13}C$ NMR (75 MHz, $CDCl_3$) δ 158.5, 155.8, 136.3, 126.7, 120.0, 118.1, 107.0, 104.6, 94.3, 55.8 (2C's), 30.9, 28.8, 25.3, 23.1, and 22.6 ppm downfield from TMS. IR (neat) 2940, 2840, 1595, 1470, 1440, 1260, 1160, 1105, 1070, and 1025 $cm^{-1}$.

6.2. 3-(1'-CYCLOHEXENYL)METHYL-2-HYDROXY-4-METHOXYBENZOIC ACID (12a)

Compound 9a was metalated at the 4-position by the following procedure. A hexane solution of 9a (1.0 equiv) and TMEDA (1.1 equiv) was treated with a hexane solution of n-BuLi (1.1 equiv) added gradually at 0° C. under an atmosphere of nitrogen. The solution was stirred at room temperature for 3 hours and then cooled to –78° C.

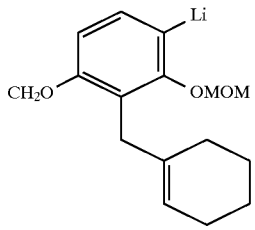

Li-9a

The aryllithium reagent Li-9a prepared by the above route was then exposed to a stream of dried carbon dioxide gas bubbled through the –78° C. solution for 0.5 hour. Carrying out this reaction at 0° C. cuts the resulting yield in half. The mixture was allowed to warm up to room temperature while maintaining a steady stream of gas. The mixture was poured into water and extracted a few times with 5% aqueous sodium hydroxide, then acidified to pH 1 with concentrated hydrochloric acid, and then extracted into ether. The crude product was back-extracted into $Et_2O$ and the combined organic layers dried over magnesium sulfate. The solvent was evaporated and the residue redissolved in a minimum of boiling ether. The warm solution was allowed to cool slightly, and then hexane was added to the point of cloudiness. The mixture was then allowed to stand in the freezer. An off-white solid with a melting point of 161°–163° C. was harvested (66% yield). Anal. Calcd. for $C_{15}H_{18}O_4$: C, 68.69; H, 6.92. Found: C, 68.75; H, 6.95. $^1H$ NMR (90 MHz, acetone-$d_6$) δ 7.81 (1H, d, J=9 Hz), 6.62 (1H, d, J=9 Hz), 5.26 (1H, broad s), 4.26 (2H, broad s), 3.90 (3H, s), 3.29 (2H, broad s), 2.01 (4H, m), and 1.57 (4H, m) in ppm downfield from TMS. $^{13}C$ NMR (acetone-$d_6$) δ 173.0, 164.3, 162.1 (2C's), 136.5, 130.6, 121.0, 115.9, 106.5 (2C's), 103.3, 56.3, 30.0, 29.4, 25.8, 23.8, 23.2 (2C's). IR (KBr) 1650, 1610, 1500, 1455, 1265, 1185, and 1090 $cm^{-1}$.

6.3. 3-(1'-CYCLOHEXENYL)METHYL-2-HYDROXY-4-METHOXYBENZALDEHYDE (12b)

A solution of aryllithium reagent Li-9a, prepared in situ by the procedure described in Section 6.2, was cooled to –12° C. and treated with neat N,N'-dimethylformamide (1.5 equiv) added all at once. The mixture was stirred at room temperature for 3 hours. The mixture was then poured into water, saturated with sodium chloride, and extracted with $Et_2O$. The organic layers were combined, dried ($MgSO_4$), and concentrated in vacuo; the residue was recystallized from ether-hexane (See Section 6.2). The product was purified by column chromatography (silica, ether/hexane eluent). Mp 48°–49° C. Anal. Calcd. for $C_{15}H_{18}O_3$: C, 73.15; H, 7.37. Found: C, 73.22; H, 7.40. $^1H$ NMR ($CDCl_3$) δ 11.42 (1H, broad s), 9.64 (1H, s), 7.33 (1H, d), 6.51 (1H, d), 5.23 (1H, broad s), 3.83 (3H, s), 3.26 (2H, broad s), 1.96 (4H, m), and 1.56 (4H, m) in ppm downfield from TMS. $^{13}C$ NMR ($CDCl_3$) δ 194.7, 164.6, 161.3, 135.5, 133.8, 120.6, 115.9, 115.6, 103.1, 55.9, 29.9, 28.8, 25.2, 23.0, and 22.4 in ppm downfield from TMS. IR (KBr) 2930, 2840, 1625, 1495, 1255, 1100, 800, and 640 $cm^{-1}$.

6.4. 7-CARBOXY-4-METHOXYSPIRO [BENZOFURAN-2(3H) -CYCLOHEXANE] (11a)

A benzene solution of compound 12a (Section 6.2) was treated with dry Amberlyst ion-exchange resin (approximately 3–4 g per gram of substrate, dried at 110° C. under high vacuum) added in one portion. The mixture was stirred for up to 24 hours at room temperature and then filtered. The resin beads were washed thoroughly with fresh benzene and methylene chloride. The filtrates were combined, washed with water, dried over magnesium sulfate, and concentrated in vacuo. The product 11a was purified in 85% yield by column chromatography. Mp 192°–194° C. Anal. Calcd. for $C_{15}H_{18}O_4$: C, 68.69; H, 6.92. Found: C, 68.52; H, 6.99. $^1$H NMR (CDCl$_3$) δ broad roll centered at about 12.0 (1H), 7.85 (1H, d, J=9 Hz), 6.50 (1H, d, J=9 Hz), 3.89 (3H, s), 2.94 (2H, s), and 1.69 (10H, broad m) in ppm downfield from TMS. $^{13}$C NMR (CDCl$_3$) 164.5, 160.6, 158.7, 132.7, 113.6, 106.2, 104.5, 94.2, 55.7, 38.0, 37.1 (2C's), 24.9, and 23.2 (2C's) in ppm downfield from TMS. FIG. 1 shows the infrared (KBr) spectrum. IR (KBr) 1660, 1615, 1445, 1435, 1385, and 1100 cm$^{-1}$. Cyclization was also accomplished by heating the phenol precursor in either a 50/50 4N hydrochloric acid/isopropanol solvent mixture or a boron trifluoride etherate solution in THF. This latter cyclization procedure is not recommended for any phenol precursor other than 12a, however.

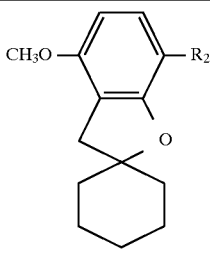

11a  $R_2$= —COOH
11b  $R_2$= —CHO
11c  $R_2$= —CONHCH$_3$
11d  $R_2$= —CONH$^t$Bu
11e  $R_2$= —CH$_2$OH

11

6.5. 7-FORMYL-4-METHOXYSPIRO [BENZOFURAN-2(3H)-CYCLOHEXANE] (11b)

The phenol precursor 12b was treated with Amberlyst resin as described in the previous section. The product 1ib was isolated and purified by column chromatography (83% yield). Mp 62°–63° C. Anal. Calcd. for $C_{15}H_{18}O_3$: C, 73.15; H, 7.37. Found: C, 73.22; H, 7.40. $^1$H NMR (CDCL$_3$) δ 10.16 (1H, s), 7.66 (1H, d, J=9 Hz), 6.46 (1H, d, J=9 Hz), 3.88 (3H, s), 2.88 (2H, s), 1.4–2.0 (10H, broad m).

Compound 11b is easily transformed to lie by a metal hydride reduction step or other means well-known in the art.

6.6. COMPLEMENT INHIBITION

The dihydrobenzofuran and spirobenzofurancyclohexane compounds of the general formulae 3, 4, the synthetic intermediates of the general formula 5, and the salts thereof of the present invention were assayed for their ability to inhibit complement by the methods described infra.

6.6.1. DEMONSTRATION OF INHIBITION OF C3a AND C5a PRODUCTION

The ability to inhibit complement was tested by assaying for specific inhibition of C3a and C5a production. For all experiments, a single human serum pool, to be used as a source of complement, was aliquoted and stored frozen at −70° C. Human IgG was heat-aggregated, aliquoted, and stored frozen at −70° C. For each experiment, serum aliquots were equilibrated at 37° C. with varying concentrations of the compounds tested. The classical complement pathway was initiated by the addition of aggregated human IgG. Control samples containing no IgG were always included. After a fixed reaction time of 10 minutes (determined in an earlier time-course study to provide a convenient time interval during which the production of C5a or C3a is nearly complete, i.e., greater than 90%), the levels of the released complement peptides (C5a or C3a) were determined by radioimmunoassay using commercially available radioimmunoassay (RIA) kits (C5a RIA, UpJohn Cat. No. 3250-02; C3a RIA, UpJohn Cat. No. 3245-01; C5a RIA, Amersham Cat. No. RPA.520; C3a RIA, Amersham RPA.518).

Since a competitive immunoassay was used, complement peptide (C5a and C3a) concentrations varied inversely with the counts. The Counts Bound (CB) for a sample was defined as the total counts (in counts per minute, cpm) measured in the pellet minus the counts measured in a nonspecific binding (NSB) control. The NSB control was a sample containing only tracer peptide ($^{125}$I-labelled) and second precipitating antiserum; it contained no C5a- or C3a-specific antiserum.

The y-axis in FIG. 2 represents the fraction inhibition. The fraction inhibition is equal to the Counts Bound (CB) for a "sample," less the CB in the "sample with no added compound," divided by the CB for the "no IgG control" less the CB in the "sample with no added compound."

$$\text{INHIBITION} = \frac{[(CB \text{ sample}) - (CB \text{ no compound})]}{[(CB \text{ no IgG}) - (CB \text{ no compound})]}$$

When C5a production is inhibited at concentrations of added compound at which C3a production is unaffected, the data suggest that complement inhibition is directed toward the C5 activation step. FIG. 2 is representative of the data plots obtained from the assays described above. The results are summarized in Table VI and demonstrate that the complement inhibition activities exhibited by some of the compounds appear to be directed toward inhibition of C5 activation, and that the inhibitory activities are comparable to that of K-76 COONa itself.

TABLE VI

IN VITRO COMPLEMENT INHIBITION IN HUMAN SERUM

| | $IC_{50}$ (mM)[a] | |
|---|---|---|
| Compound | C3a | C5a |
| (+)-22a | 11 | 6 |
| (+)-20a | >14[b] | 8 |
| (−)-20a | 11 | 6 |
| (+)-23a | >14[b] | >14[b] |
| 12b | 18 | 9 |
| 12a | 13 | 8 |
| 11a | 22 | 5 |
| K-76 COONa | —[c] | 3 |

[a]The concentration of compound required to inhibit C3a or C5a production 50% relative to control samples which contained no test compound.
[b]The inhibition observed at this concentration was less than about 50%.
[c]Only marginal inhibition was observed at a concentration of about 8.5 mM.

6.6.2. DEMONSTRATION OF INHIBITION OF COMPLEMENT-MEDIATED HEMOLYSIS

The ability to inhibit complement was also tested by assaying for inhibition of complement-mediated red cell lysis (hemolysis). The inhibition of hemolysis was determined as a function of compound concentration. The compounds to be tested were diluted in 0.1M Hepes buffer (0.15N NaCl, pH 7.4), and 50 μl were added to each well of a V-bottom microtiter plate. Human serum, used as the complement source, was diluted 1 to 500 in Hepes buffer, and 50 µl were added to each well. Next, commercially available sheep erythrocytes with anti-sheep antibody (Diamedix Cat. No. 789-001) were used as received and added at 100 µl/well to initiate the complement pathway leading to hemolysis. The plate was incubated for 60 minutes at 37° C. and then centrifuged at 500×g for 10 minutes. The supernatants were removed and placed in a flat-bottom microtiter plate. The extent of hemolysis was measured as a function of the sample absorbance at 410 nm. The maximal absorbance (corresponding to maximal hemolysis), $A_{max}$, was obtained from the absorbance value of an erythrocyte sample containing only human serum, $A_S$, less the absorbance of a sample containing only the red cells, $A_0$. Thus, $A_{max}=A_S-A_0$. The difference between the absorbance of an erythrocyte sample containing both human serum and inhibitive compound, and the absorbance of a cell sample containing inhibitive compound only, was defined as $A_{sample}$. The inhibition, IH, was expressed as the fraction $(A_{max}-A_{sample})/A_{max}$, and $IH_{50}$ was defined as the concentration of inhibitive compound required to produce a value of IH=½.

FIG. 3 shows the plot of inhibition, IH, versus the concentration of 11a added to the cell samples. The concentration of 1a corresponding to $IH_{50}$ is approximately 0.9 mM. Table VII summarizes the results of several assays using some of the compounds of the present invention and shows their effectiveness in inhibition of hemolysis.

TABLE VII

INHIBITION OF COMPLEMENT-MEDIATED HEMOLYSIS

| Compound | $IHO_{50}$ | (mM)* | N = |
|---|---|---|---|
| 11a | 1.33 | (±0.49) | 10 |
| 12a | 2.10 | (±0.71) | 2 |
| 14a | 3.0 | | |
| 15a | 0.82 | (±0.16) | 2 |
| (+)-20a | 0.68 | (±0.03) | 2 |
| (−)-20a | 0.38 | (±0.11) | 2 |
| (+)-23a | | 2.1 | |
| (−)-23a | | 2.4 | |
| 30a | 0.53 | (±0.19) | 23 |
| 31a | 1.45 | (±0.21) | 2 |
| K-76 COONa | 0.57 | (±0.17) | 9 |

*The concentration of compound required to produce a value for hemolysis inhibition (IH, as defined supra) of 1/2.

6.7. IMMUNOSUPPRESSIVE ACTIVITIES

The dihydrobenzofuran and spirobenzofurancyclohexane compounds of the general formulae 3, 4, intermediate 5, and the salts thereof of the present invention were tested for their ability to inhibit cell-mediated immune activity. The specific activities demonstrated by the tested compounds included the inhibition of natural killer (NK) activity, the inhibition of peripheral blood lymphocyte (PBL) proliferation, and the inhibition of cell surface interleukin-2 receptor expression as described infra. In addition, the ability of compound 11a to inhibit the proliferation of Chinese hamster ovary (CHO) cells was tested; no inhibition of CHO cells was observed, suggesting that the compounds inhibitory activities were specific to the lymphoid cells of the immune system. The experiments were conducted using in vitro assays for determining dose-dependent effects of the compounds of the invention on immune function.

6.7.1. DEMONSTRATION OF INHIBITION OF NATURAL KILLER ACTIVITY

Compounds were tested for their effects on the ability of peripheral blood mononuclear cells to lyse NK-sensitive target cells, K562. NK activity was determined using $^{51}$Cr-labeled K562 erythromyeloid leukemia cells as targets, and normal peripheral blood mononuclear cells as effector cells, in a four hour cytotoxicity assay. Effector cells were isolated from fresh blood by Ficoll-Hypaque gradient centrifugation, and 100 µl of a 5×10$^5$ cell/well suspension were added to each well of a V-bottom microtiter plate. The compound 11a was diluted in RPMI 1640 medium containing 10% fetal calf serum and dispensed at 100 µl per well. Target cells (K562) were labeled for 30 minutes with 100 µCi of $^{51}$Cr, washed thoroughly and dispensed in a 20 µl volume at 10$^4$ cells/well. These cell concentrations resulted in an effector-to-target cell ratio of 50:1. The microtiter plate was centrifuged at 50×g for 5 minutes and incubated in a humidified chamber with 5% $CO_2$ at 37° C. After 4 hours, 100 µl were removed from each well and the radioactivity was measured with a LKB 1275 gamma counter. The percent specific lysis was calculated as follows:

% specific lysis=[(EXP−SR)/(TOTAL−B)]×100 where EXP (experimental value) was obtained using effector and target cells; SR (the spontaneous release) was obtained from target cells incubated with media alone; TOTAL release was obtained by hypotonic lysis in water; and B represents instrumental background. Means were calculated from quadruplicate wells and the standard deviations never exceeded 10%. Viability of the effector cells incubated with the test compound was determined by trypan blue exclusion.

The results of the inhibition of natural killer activity for 7-carboxy-4-methoxyspiro[benzofuran-2(3H)-cyclohexane] (11a) sodium salt are summarized in Table VIII.

TABLE VIII

INHIBITION OF NATURAL KILLER ACTIVITY BY 7-CARBOXY-4-METHOXYSPIRO[BENZOFURAN-2(3H)-CYCLOHEXANE]
(11a), SODIUM SALT

| (11a) Concentration (mM) | % Specific Lysis | Spont. Release Target Cells Alone (K562) | % Viability of Effector Cells[a] |
|---|---|---|---|
| 0 | 17 | 6 | 95 |
| 0.4 | 7 | 5 | 95 |
| 0.8 | 4 | 5 | 95 |
| 1.6 | 1 | 5 | 95 |
| 3.2 | −1 | 5 | 76 |
| 6.4 | 18 | 23 | 5 |

[a]Viability was determined by trypan blue exclusion.

The data listed in Table VIII indicate that compound 11a can, at appropriate concentrations, effectively inhibit natural killer activity.

6.7.2. DEMONSTRATION OF INHIBITION OF PROLIFERATION OF PERIPHERAL BLOOD LYMPHOCYTES

The proliferation of human peripheral blood lymphocytes (PBL) in response to phytohemagglutinin (PHA, Wellcome) or anti-CD3 monoclonal antibody (OKT-3, Ortho) was assessed by the incorporation of $^3$H-thymidine. Compound 11a was diluted in culture media to the desired concentrations, human PBL were added to a final concentration of 10$^6$ cells/ml, and then either PHA (Wellcome) or anti-CD3 (OKT3, Ortho) antibody (final concentration, 1 mg/ml) was added to initiate proliferation. The final volume per sample was 100 µl. The cells were incubated for 72 hours after stimulation, pulsed with 1 µCi $^3$H-thymidine per sample for 4 hours, harvested, and counted in a scintillation counter. Separate experiments, conducted on samples exposed only to varying amounts of 11a without the stimulant, showed that the PBL were viable, as determined visually by trypan blue exclusion, in the concentration ranges of 11a used above. The results (FIGS. 4, 5) showed that compound 11a inhibited PBL proliferation in a dosedependent manner. Half-maximal inhibition was observed at about 0.5 mM of 11a when cultures were stimulated with either PHA (FIG. 4) or anti-CD3 antibody (FIG. 5). Because cell viability was unaffected by the presence of 11a (see supra), the inhibition apparently was not due to cytotoxic effects. Additional compounds of the invention were tested for their immunosuppressive activities, with the results presented in Table IX.

TABLE IX

INHIBITION OF PROLIFERATION OF
PERIPHERAL BLOOD LYMPHOCYTES

| | $IP_{50}$ (mM)[a] | |
|---|---|---|
| Compound | PHA-stimulated PBL | OKT-3-stimulated PBL |
| 11a | 0.4 | 0.5 |
| 15a | 0.7 | 0.4 |
| (+)-20a | 2.1 | 1.7 |
| (-)-23a | 2.8 | 2.0 |
| K-76 COONa | 0.5 | 0.5 |

[a]The concentration of compound required to inhibit PBL proliferation 50% relative to control samples which contained no test compound.

The results (Table IX) revealed that each of the tested compounds inhibited PBL proliferation.

Release of cell surface interleukin-2 receptor (IL-2R) or CD8 antigen from lymphocytes is a correlate of T cell activation (Rubin et al. J. Immunol. 1985, 135, 3172–77; Rubin et al. Fed. proc. 1985 44, 946; Fujimoto, J. et al. *J. Exp. Med.* 1983, 159, 752–66; Tomkinson, B. et al. 2d Annual Conference on Clinical Immunol. Washington, D.C., Oct. 30, 1987). In some experiments, the level of IL-2R or CD8 protein released into the supernatant of the PBL cultures was assessed by removing aliquots therefrom just prior to pulsing with $^3$H-thymidine. Commercially available enzyme immunoassay kits (CELLFREE™ IL-2R, Cat. No. CK1020, T Cell Sciences, Inc., Cambridge, Mass., or CELL-FREE™ T8/CD8, Cat. No. CK1040, T Cell Sciences) were used to determine the levels of the two analytes. The results using compound 11a showed that 11a was an inhibitor of both IL-2R (FIG. 6) and CD8 (FIG. 7) protein release, in stimulated PBL cultures.

6.7.3. DEMONSTRATION OF INHIBITION OF CELL SURFACE INTERLEUKIN-2 RECEPTOR EXPRESSION

The interleukin-2 receptor (IL-2R) is not detectable on the surface of resting T cells. Upon activation by specific antigens or mitogens, T cell proliferation is mediated by an autocrine mechanism whereby activated cells secrete interleukin-2 and express cell surface IL-2R (Meuer, S. C. et al. Proc. Natl. Acad. Sci. U.S.A. 1984, 81, 1509; Tsudo, M., et al. J. Exp. Med. 1984, 160, 612–617; Waldmann, T. A., et al. J. Exp. Med. 1984, 160, 1450–1466).

Compounds were tested for their ability to inhibit T cell activation, as indicated by inhibition of cell-surface IL-2R expression. PBL cultures (1.5 ml; 24-well plates) were stimulated with PHA (1 µg/ml) for 72 hours in the absence or presence of varying amounts of compound 11a. Subsequently, the cells were stained using fluorescein isothiocyanate (FITC)-labeled anti-IL-2R antibody (Act-T-Set IL-2R, Cat. No. AA2009, T Cell Sciences, Inc., Cambridge, Mass.) and analyzed by flow cytometry (Ortho System 30) (Table X).

TABLE X

INHIBITION OF CELL SURFACE IL-2R EXPRESSION BY
7-CARBOXY-4-METHOXYSPIRO[BENZOFURAN-2(3H)-
CYCLOHEXANE]
(11a), SODIUM SALT

| Concentration of 11a (nM) | Number of Cells Positive for IL-2R | Percentage Positive[a] |
|---|---|---|
| 0 | 4845 | 96.9 |
| 0.44 | 913 | 18.3 |
| 1.76 | 225 | 4.5 |

Based upon a total cell count of 5000.

The results listed in Table X indicate a dramatic reduction in the number of PBL expressing the IL-2R in the presence of 11a. We also observed that the amount of IL-2R cell surface expression was reduced in the presence of 11a. The data thus demonstrate that compound 11a significantly suppresses IL-2R cell-surface expression, indicating that this compound can effectively inhibit T cell activation in PBL cultures.

6.7.4. LACK OF INHIBITION OF CHO CELL PROLIFERATION

The specificity of compound 11a's inhibitory activity upon immune cells was demonstrated by assaying for 11a's ability to inhibit the proliferation of Chinese hamster ovary (CHO) cells. Non-confluent CHO cells were allowed to proliferate for 4 hours in a 96-well plate at a volume of 50 µl per well in the absence or presence of compound 11a at a concentration of 1.8 mM. The cells were pulsed with 0.5 µCi of $^3$H-thymidine per sample for 4 hours, harvested, and the amount of incorporated $^3$H-thymidine was determined by scintillation counting. The CHO cells allowed to proliferate in the absence of added compound yielded a value of 57025 (±7530) CPM. The value for the sample grown in the presence of 11a was 52549 (±6272) CPM. These values revealed no statistical difference in the proliferation rate of the two samples. Because the CHO cell line is of the non-lymphoid type, this result suggests that the compounds of the present invention do not generally inhibit mammalian cell proliferation, but inhibit activation and/or proliferation of PBL cultures.

7. EXAMPLES OF 6-CARBOXYL-4-SUBSTITUTED SPIRO[BENZOFURAN-2(3H)-CYCLOHEXANES]

7.1. 6-CARBOXYL-4-METHOXYSPIRO [BENZOFURAN-2(3H)-CYCLOHEXANE] SODIUM SALT (44a) AND 6-CARBOXYLATE-4-ETHOXY-SPIRO [BENZOFURAN-2(3H)-CYCLOHEXANE] SODIUM SALT (44b)

Preparation of 33a–b

Methyl 3,5-dihydroxybenzoate (10 g, 59.5 mmol) in dry acetone (200 ml) was added to dry $K_2CO_3$ (8.2 g, 59.4 mmol). Dimethysulfate (for 33a; 7.5 g, 59.5 mmol) was added to the mixture, which was refluxed for 24 h. The mixture was filtered. Ether (200 ml) was added to the solution and was extracted with $H_2O$ (100 ml×2). The organic solution was dried over $MgSO_4$; after removal of solvent, a crude product (9.0 g) was purified by chromatography (1:19 EtOAc/CH$_2$Cl$_2$) to afford 33a as a white solid, yield 3.9 g (36%). mp 95°–97° C.; TLC R$_f$ 0.58 (1:9 EtOAc/CH$_2$Cl$_2$). NMR (CDCl$_3$) δ 7.26–7.13 (m,2H), 6.63 (m,1H), 5.90 (s,1H, OH), 3.90 (s,3H), 3.80 (s,3H). For 33b: The procedure of 33a was modified by using diethyl sulfate as alkylating agent. 33b: mp 98°–100° C.; yield, 33%; TLC R$_f$ 0.51 (1:9 EtOAc/CH$_2$Cl$_2$). NMR (CDCl$_3$) δ 7.16–7.14 (m, 2H), 6.62 (m,1H), 5.70 (s,1H, OH), 4.07–4.00 (q, 2H), 3.90 (s,1H), 1.41–1.38 (t,3H).

Preparation of 34a–b

NaH (50% in mineral oil; 2.2 g, 91.7 mmol) was washed with hexane (40 ml×2) under N$_2$. Dry DMF (50 ml) was added and the mixture was cooled to 0° C. A solution of 33a (7.6 g, 41.7 mmol) in dry DMF (40 ml) was added slowly to the mixture, and then stirred for 1 h at 25° C. The mixture was recooled to 0° C., and a solution of MOMCl (3.7 g, 45.8 mmol) in dry pMF (20 ml) was added dropwise. The mixture was stirred at 25° C. for 3 h. Ether (200 ml) was added to the mixture and washed with H$_2$O (100 ml×4). The ether portion was dried (MgSO$_4$) and concentrated to give a pale yellow liquid as 34a; yield 8.2 g (87%). TLC R$_f$ 0.44 (CH$_2$Cl$_2$). IR (neat) 2950, 1740, 1600, 1460, 1430, 1320, 1240, 1150, 1060, 1020 770 cm$^{-1}$. NMR (CDCl$_3$) Δ7.32–7.31 (m, 1H), 7.24–7.23 (m,1H), 5.19 (s,2H), 3.90 (s,2H), 3.83 (s,3H), 3.48 (s,3H). For 34b: Procedure for 34a was modified. Yield, 95%; TLC R$_f$ 0.42 (CH$_2$Cl$_2$). IR (neat) 2980, 1725, 1600, 1450, 1300, 1240, 1150, 1060, 1030, 770 cm$^{-1}$. NMR (CDCl$_3$) δ 7.30–7.29 (m,1H), 7.23–7.22 (m,1H), 6.79–6.78 (m, 1H), 5.19 (s,2H), 4.09–4.02 (q,2H), 3.90 (s,3H), 3.48 (s,3H), 1.44–1.39 (t,3H).

Preparation of 35a–b

LiAlH$_4$ (1.7 g, 44.2 mmol) was suspended in dry THF (150 ml) under N$_2$ and cooled to 0° C. A solution of 34a (10 g, 44.2 mmol) in THF (20 ml) was added dropwise. The mixture was stirred for 3 h at 25° C. Excess LiAlH$_4$ was carefully decomposed by additional ice. The mixture was filtered through silica gel and rinsed with ether (150 ml). The solution was washed with H$_2$O (50 ml×2), dried and concentrated to give a colorless liquid as 35a, yield 6.7 g (76%). TLC R$_f$ 0.38 (1:4 EtOAc/CH$_2$Cl$_2$). IR (neat) 3400, 2920, 1600, 1460, 1290, 1150, 1050, 925, 840 cm$^{-1}$. NMR (CDCl$_3$) Δ6.67–6.50 (m,3H), 5.16 (s,2H), 4.65 (s,2H), s, 3H), 3.50 (s, 3H), 2.56 (s,H,OH). 35b was prepared by the same procedure that used for 35a: yield, 90–92%; TLC R$_f$ 0.52 (1:4 Et$_2$O/CH$_2$Cl$_2$). IR (neat) 3400, 2940, 1600, 1460, 1390, 1280, 1210, 1155, 1140, 1030, 925, 850 cm$^{-1}$. NMR (CDCl$_3$) δ 6.80–6.57 (m, 3H), 5.27 (s,2H), 4.70 (s,2H), 4.20–3.97 (q,2H), 3.50 (s,3H), 2.00 (s,H,OH), 1.50–1.33 (t, 3H).

Preparation of 36a–b

To a solution of 35a (2.2 g, 11.1 mmol) and imidazole (1.51 g, 22.2 mmol) in CH$_2$Cl$_2$ (50 ml), was added slowly TBDMSCl (2.0 g, 13.3 mmol) dissolved in CH$_2$Cl$_2$ (10 ml). The mixture was stirred at 25° C. for 3 h. The mixture was washed with H$_2$O (100 ml×2), dried with (MgSO$_4$) and concentrated to give a colorless liquid, 3.3 g (94%) as 36a. TLC R$_f$ 0.8 (4:6 hexane/CH$_2$Cl$_2$). IR (neat) 152940, 1600, 1460, 1365, 1300, 1250, 1210, 1190, 1150, 1100, 1055, 1025, 925, 835, 765 cm$^{-1}$. NMR (CDCl$_3$) δ 6.62–6.61 (m,1H), 6.58–6.56 (m,1H), 6.49–6.47 (t,1H), 5.15 (s,2H), 4.69 (s,2H), 3.78 (s,3H), 3.47 (s,3H), 0.95 (s,9H), 0.10 (s,6H). For 36b: It was prepared by the procedure that used for 36a; yield, 90–95%. IR (neat) 2940, 1600, 1460, 1390, 1370, 1290, 1250, 1150, 1100, 1030, 940, 840, 775 cm$^{-1}$. NMR (CDCl$_3$) δ 6.61–6.59 (m, 1H), 6.56–6.54 (m,1H), 6.48–6.47 (t,1H), 5.15 (s,2H), 4.67 (s,2H), 4.04–3.97 (q,2H), 3.47 (s,3H), 1.43–1.37 (t,3H), 250.94 (s,9H), 0.10 (s,6H).

Preparation of 38a–b

To a solution of 36a (8.2 g, 26.2 mmol) and TMEDA (4.6 g, 39.4 mmol) in dry THF (200 ml) under N$_2$ at 0° C., n-BuLi (12 ml, 28.8 mmol) was added slowly. The solution was stirred 30 min at 0° C. and then 1.5 h at 25° C. The solution was recooled to –78° C., CuI (7.5 g, 39.4 mmol) was added in one portion under positive N$_2$ stream. The mixture was stirred for 1.5 h at –78° C. to –40° C. The mixture was recooled to –78° C., bromide 37 (5.5 g, 31.5 mmol) in THF (20 ml) was added dropwise, and the mixture was stirred 4 h from –78° C. to 25° C. Ether (200 ml) was added to the solution and washed with 20% NH$_4$OH solution until the aqueous layer was no longer blue, dried and concentrated to give a brown liquid (10.4 g). Purification by chromatography (1:19 EtOAc/hexane) afforded a colorless liquid as product 38a (8.7 g, 82%). TLC R$_f$ 0.70 (1:9 EtOAc/hexane). IR (neat) 2930, 1610, 1590, 1460, 1430, 1260, 1200, 1100, 1080, 1030, 840, 780 cm$^{-1}$. NMR (CDCl$_3$) δ 6.68 (s,1H), 6.61 (s,1H), 5.22–5.18 (m,1H), 5.13 (s,2H), 4.71 (s, 2H), 3.79 (s,3H), 3.44 (s,3H), 3.26 (s,2H), 1.97–1.88 (m,4H), 1.62–1.46 (m,4H), 0.94 (s, 9H), 0.10 (s,6H). For 38b: Preparation was essentially that used for 38a. Yield, 60–62%. TLC R$_f$ 0.66 (1:9 EtOAc/hexane). IR (neat) 2940, 1610, 1590, 1440, 1390, 1370, 1260, 1200, 1150, 1100, 840, 770 cm$^1$. NMR (CDCl$_3$) δ 6.67 (s,1H), 6.58 (s,1H), 5.25–5.22 (m,1H), 5.13 (s,2H), 4.69 (s,2H), 4.03–3.96 (q,2H), 3.44 (s,3H), 3.28 (s,2H), 2.00–1.89 (m,4H), 1.76–1.47 (m,4H), 1.39–1.35 (t,3H), 0.94 (s,9H), 0.10 (s,6H).

Preparation of 39a–b

To the solution of 38a (7.2 g, 14.7 mmol) in THF (100 ml), (Bu)$_4$ NF (1.0M in THF, 21 ml, 21 mmol) was added slowly at 25° C. Solution was stirred at 25° C. for 2 h. Ether (100 ml) was added to the solution, then washed with 5% HCl (20 ml) and H$_2$O (100 ml×2). The organic layer was dried and concentrated to give a colorless liquid as 39a, yield 6.0 g (90%). TLC R$_f$ 0.53 (2:3 EtOAc/hexane). IR (neat) 3380, 3920, 1610, 1590, 1450, 1430, 1400, 1200, 1160, 1110, 1080, 1030, 960, 925, 830 cm$^{-1}$. NMR (CDCl$_3$) δ 6.70 (s,1H), 6.61 (s,1H), 5.21–5.18 (m,1H), 5.14 (s,2H), 4.62 (s,2H), 3.79 (s,3H), 3.44 (s,3H), 3.26 (s,2H), 2.00–1.87 (m,4H), 1.62–1.48 (m,4H). For 39b: Preparation was essentially that used for 39a. Yield, 95%. TLC R$_f$ 0.58 (2:3 EtOAc/hexane). IR (neat) 35 3400, 2940, 1610, 1590, 1440, 1390, 1200, 1150, 1120, 1070, 1030, 925, 820 cm$^{-1}$. NMR (CDCl$_3$) δ 6.69 (s,1H), 6.58 (s,1H), 5.30–5.25 (m,1H), 5.14 (s,2H), 4.59 (s,2H), 4.03–3.96 (q,2H), 3.44 (s,3H), 3.28 (s,2H), 2.00–1.88 (m,4H), 1.60–1.46 (m,4H), 1.39–1.35 (t,3H).

Preparation of 40a–b

To a mixture of PCC (5.5 g, 25.6 mmol) in CH$_2$Cl$_2$ (100 ml) at 25° C. was added 39a (4.6 g, 15.7 mmol) in CH$_2$Cl$_2$ (50 ml) slowly. The mixture was stirred at 25° C. for 4 h more. The mixture was filtered through silica gel and rinsed with EtOAc (40 ml). The solution was washed with H$_2$O (50 ml), dried (MgSO$_4$) and concentrated to give a yellow liquid which then was purified by chromatography (3:7 EtOAc/hexane) to afford a pale yellow liquid as 40a, yield 4.2 g (92%). TLC R$_f$ 0.66 (3:7 EtOAc/hexane). IR (neat) 2920, 1690, 1580, 1450, 1430, 1380, 1300, 1200, 1150, 1110, 1070, 1020, 920, 840, 740, 720 cm$^{-1}$. NMR (CDCl$_3$) δ 9.89 (s,1H), 7.23 (s,1H), 7.10 (s,1H), 5.22 (s,2H), 5.20–5.18 (m,1H), 3.86 (s,3H), 3.46 (s,3H), 3.33 (s,2H), 1.98–1.88 (m,4H), 1.61–1.48 (m,4H).

For 40b

Procedure of preparation was essentially that used for 40a. Yield, 75–81%. TLC R$_f$ 0.56 (1:4 EtOAC/hexane). IR (neat)

2920, 1700, 1585, 1440, 1380, 1310, 1200, 1160, 1110, 1070, 1030, 960, 920, 845, 740, 720 cm$^{-1}$. NMR (CDCl$_3$) δ 9.88 (s,1H), 7.22 (s,1H), 7.08 (s,1H), 5.25–5.22 (m,1H), 5.21 (s,2H), 4.12–4.05 (q,2H), 3.47 (s,3H), 3.36 (s,2H), 2.00–1.89 (m,4H), 1.60–1.38 (m,4H), 1.43–1.39 (t,3H).

Preparation of 41a–b

To a solution of 40a (4.2 g, 14.5 mmol) in 2-propanol (30 ml) and THF (15 ml) at 0° C. was added slowly aq. 4N HCl solution (40 ml, 160 mmol) in 2-propanol (10 ml). The solution was then stirred at 25° C. for 16 h or until disappearance of 40a (by TLC). The solution was extracted with ether (50 ml×3). The ether solution was washed with H$_2$O (30 ml), then dried and concentrated. The crude product was purified by chromatography (3:7 EtOAc/hexane) to afford 41a as white solid, yield 3 g (84%). mp 153°–155° C. TLC R$_f$ 0.60 (3:7 EtOAc/hexane). NMR (CDCl$_3$) δ 9.90 (s,1H), 7.04 (m,2H), 5.78 (s,1H,OH), 5.68–5.65 (m,2H), 3.90 (s,3H), 3.48 (s,2H), 2.09–2.01 (m,4H), 1.96–1.90 (m,4H). For 41b: Procedure of preparation was essentially that used for 41a. Yield, 76%; TLC R$_f$ 0.34 (1:4 EtOAc/hexane). NMR (CDCl$_3$) δ 9.86 (s,1H), 7.00 (m,2H), 5.80 (s,1H,OH), 5.70–5.66 (m,2H), 4.13–4.06 (q,2H), 3.47 (s,2H), 2.05–2.02 (m,2H), 1.92–1.88 (m, 2H), 1.63–1.54 (m,4H), 1.46–1.41 (t,3H).

Preparation of 42a–b

Amberlyst 15 (10 g) was added in one portion to the solution of 41a (3.3 g, 13.4 mmol) in CH$_2$Cl$_2$ (100 ml). The mixture was stirred at 25° C. for 6 h. The mixture was filtered and the solution was washed with H$_2$O (100 ml), dried and concentrated to give a crude product (3 g) which then was purified by chromatography (1:4 EtOAc/hexane) to afford 42a as a white solid (2.5 g, 76%). TLC R$_f$ 0.57 (1:4 EtOAc/hexane). IR (KBr) 2930, 1690, 1600, 1430, 1390, 1350, 1325, 1220, 1120, 1030, 920, 830, 20805, 745 cm$^{-1}$. NMR (CDCl$_3$) δ 9.85 (s,1H), 6.93 (s,1H), 6.89 (s,1H), 3.88 (s,3H), 2.94 (s,2H), 1.86–1.64 (m,6H), 1.55–1.45 (m,4H). $^{13}$C NMR (CDCl$_3$) δ 191.77, 160.53, 156.90, 138.19, 121.25, 105.65, 102.81, 90.36, 55.58, 38.48, 37.23, 25.05, 22.95. For 42b: Procedure of preparation was essentially that used for 42a. mp 105°–106° C. Yield, 82%; TLC R$_f$ 0.55 (1:4 EtOAc/hexane). NMR (CDCl$_3$) δ 9.84 (s,1H), 6.91 (s,1H), 6.87 (s,1H), 4.15–4.08 (q,2H), 2.95 (s,2H), 1.86–1.68 (m,6H), 1.53–1.45 (m,4H), 1.45–1.40 (t,3H).

Preparation of 43a–b

To a mixture of aq. 2N NaOH (30 ml) containing Ag$_2$O (2.4 g, 10.2 mmol) at 50° C., a solution of 42a (1 g, 4.1 mmol) in EtOH (1 ml) and THF (5 ml) was added slowly. The mixture was stirred for 6 h at 50° C. The mixture was filtered and the aq. solution was washed with ether (50 ml). The aq. solution then was cooled to 0° C., and acidified with conc. HCl solution. The white precipitate that resulted was extracted with ether, dried and concentrated to afford a white solid as 43a, yield 0.75g (71%). TLC R$_f$ 0.62 (1:9:10 MeOH/CH$_2$Cl$_2$/EtOAC). NMR (CDCl$_3$) δ 7.16 (s,2H), 3.88 (s,3H), 2.94 (s,2H), 1.87–1.65 (m,6H), 1.55–1.47 (m,4H). For 43b: Procedure for preparation was essentially that used for 43a. mp 190°–192° C. TLC R$_f$ 0.62 (1:9:10 MeOH/CH$_2$Cl$_2$/EtOAC); yield,69%. IR (KBr) 3300–2400, 1675, 1595, 1430, 1350, 1325, 1265, 1210, 1120, 1100, 1030, 955, 860, 770, 740 cm$^{-1}$. NMR (CDCl$_3$) δ 7.14 (s,2H), 4.15–4.08 (q,2H), 2.95 (s,2H), 1.86–1.65 (m,6H), 1.60–1.45 (m,4H), 1.45–1.40 (t,3H). $^{13}$C NMR (CDCl$_3$) δ 172.17, 160.08, 155.61, 130.19, 120.54, 105.39, 104.77, 90.04, 63.80, 38.49, 37.24, 25.09, 22.99, 14.84. Anal. Calcd for C$_{16}$H$_{20}$O$_4$: C, 69.54; H, 7.30. Found: C,69.40; H.7.35.

Preparation of 44a–b

Sodium hydride (50% in mineral oil, 0.58 g, 24.2 mmol) was washed with hexane (30 ml) under N$_2$, then dry ether (50 ml) was added. A solution of 43a (3.2 g, 12.2 mmol) in ether (150 ml) was added to above mixture slowly at 25° C. The mixture was stirred at 25° C. for 6 h and a white precipitate resulted. The mixture was extracted with H$_2$O (50 ml). The aqueous solution was collected and freeze dried to give a white solid (3.2 g, 92%). NMR (D$_2$O) δ 7.10 (s,1H), 6.92 (s,1H), 3.85 (s,3H) 2.82 (s,2H), 1.70–1.54 (m,6H), 1.44–1.33 (m,4H).

For 44b

Procedure for preparation was essentially that used for 44a. Yield, 75%. NMR (D$_2$O) δ 7.09 (s,1H), 6.90 (s,1H), 4.19–4.12 (q,2H), 2.89 (s,2H), 1.77–1.60 (m,6H), 1.50–1.40 (m,4H), 1.40–1.36 (t,3H).

7.2. 6-FORMYL-4-HYDROXYSPIRO[BENZOFURAN-2(3H)-CYCLOHEXANE] (52)

Preparation of 45

The procedure for the preparation of 45 was essentially that used for 34 except that two molar equivalent of NaH and MOMCl were used. Yield was 83%; TLC R$_f$ 0.65 (1:1 ether/hexane).

Preparation of 46

The procedure for preparation of 46 was essentially that used for 35. Yield was 89%; TLC R$_f$ 0.27 (1:1 ether/hexane).

Preparation of 47

The procedure for preparation was essentially that used for 36. 47: colorless liquid; yield, 83–98%; TLC R$_f$ 0.80 (1:1 ether/hexane). IR (neat) 2960, 1600, 1470, 1400, 1370, 1290, 1260, 1140, 1080, 1040, 930, 10840, 780 cm$^{-1}$. NMR (CDCl$_3$) δ 6.92–6.72 (m,3H), 5.26 (s,4H), 4.80 (s,2H), 3.57 (s,6H), 1.00 (s,9H), 0.13 (s,6H).

Preparation of 48

Procedure for preparation of 48 was essentially that used for 38. Crude product was purified by chromatography (1:19 EtOAc/hexane). 48: a clear liquid; yield, 63–79%; TLC R$_f$ 0.46 (1:19 EtOAc/hexane). IR (neat) 2940, 1615, 1590, 1455, 1440, 1400, 1370, 1260, 1160, 1100, 1050, 930, 840, 780 cm$^{-1}$. NMR (CDCl$_3$) δ 6.76 (s,2H), 5.25–5.22 (m,1H), 5.15 (s,4H), 4.70 (s,2H), 3.45 (s,6H), 3.30 (s,2H), 2.10–1.96 (m,4H), 1.95–1.88 (m,4H), 0.95 (s,9H), 0.11 (s,6H).

Preparation of 49

Procedure for preparation 49 was essentially used for 39. Yield, 95–100%; TLC R$_f$ 0.45 (3:7 EtOAc/CH$_2$Cl$_2$). IR (neat) 3400, 2930, 1620, 1590, 1440, 1290, 1190, 1155, 1110, 1040, 950, 920, 840 cm$^{-1}$. NMR (CDCl$_3$) δ 6.78 (s,2H), 5.24–5.20 (m,1H), 5.17 (s,4H), 4.63 (s,2H), 3.45 (s,6H), 3.30 (s,2H), 2.10–1.88 (m,4H), 1.73 (s,1H,OH), 1.63–1.48 (m,4H).

Preparation of 50

Procedure for preparation 50 was essentially that used for 40. Crude product was purified by chromatography (3:7 ether/hexane). Yield, 70–76%; TLC R$_f$ 0.43 (3:7 ether/hexane). IR (neat) 2930, 1700, 1585, 1435, 1380, 1290, 1155, 1105, 1050, 950, 925 cm$^{-1}$. NMR (CDCl$_3$) δ 9.89 (s,1H), 7.29 (s,2H), 5.23–5.18 (m,5H), 3.46 (s,6H), 3.37 (s,2H), 2.00–1.95 (m,4H), 1.94–1.87 (m,4H). $^{13}$C NMR (CDCl$_3$) δ 191.65, 156.49, 135.74, 135.54, 126.38, 121.11, 108.79, 94.39, 51.15, 31.61, 28.95, 25.30, 23.10, 22.46.

Preparation of 51

Procedure for preparation 51 was essentially that used for 41. Crude product was purified by chromatography (3:7 EtOAc/hexane). It should be mentioned that a large amount of expected product decomposed or was trapped on silica gel to give a low yield (28%). For 51: mp 130°–132° C. TLC R$_f$ 0.41 (3:7 EtOAc/hexane). IR (KBr) 3460, 3420, 2940, 1690, 1670, 1595, 1450, 1410, 1340, 1200, 1170, 1140, 1080, 1050, 1035, 1010, 840, 790, 740 cm$^{-1}$. NMR (CDCl$_3$) δ 9.83 (s,1H), 6.96 (s,2H), 5.72–5.68 (m,1H), 5.67 (s,2H,OH), 3.47 (s,2H), 2.08–2.01 (m,2H), 2.00–1.92 (m,2H), 1.67–1.53 (m,4H).

Preparation of 52

Procedure of preparation 52 was essentially that used for 42. Crude product was purified by chromatography with 3:7 (EtOAc/hexane) as eluent. For 52: TLC $R_f$ 0.53(3:7 EtOAc/hexane). IR (KBr) 3260, 2940, 1680, 1590, 1460, 1400, 1310, 1280, 1250, 1210, 1175, 1110, 1060, 1000, 930, 920, 840, 800, 740 cm$^{-1}$. NMR (CDCl$_3$) δ 9.81 (s, 1H), 6.88 (s,1H), 6.86 (s,1H), 2.97 (s,2H), 1.89–1.65 (m,6H), 1.58–1.45 (m,4H).

7.3. 4-BENZYLOXY-6-FORMYL-SPIRO [BENZOFURAN-2(3H)-CYCLOHEXANE] (53a)

Preparation of 53a

Sodium hydride (50% in mineral oil, 62 mg, 2.58 mmol) was washed with hexane (20 ml) under N$_2$. Dry DMF (5 ml) was added and a solution of 52 (0.30 g, 1.29 mmol) in DMF (10 ml) was added slowly at 25° C. After stirring for 30 min, a solution of benzyl bromide (0.22 g, 1.29 mmol) in DMF (5 ml) was added dropwise. The mixture was warmed to 50° C. and stirred for 2 h more. Ether (50 ml) was added to the mixture which was then washed with H$_2$O (50 ml×3), dried and concentrated to afford a crude product (0.4 g). Purification by chromatography (1:4 Et$_2$O/hexane) gave a pale yellow liquid as 53a, yield 0.3 g (71%). TLC $R_f$ 0.45 (1:4 Et$_2$O/hexane). IR (neat) 2940, 2870, 1695, 1600, 1440, 1390, 1355, 1330, 1220, 1210, 1150, 1100, 1045, 920, 830, 805, 750, 700 cm$^{-1}$. NMR (CDCl$_3$) δ 9.85 (s,1H), 7.46–7.34 (m,5H), 7.01 (s,1H), 6.91 (s,1H), 5.14 (s,2H), 2.98 (s,2H), 1.87–1.64 (m,6H), 1.56–1.42 (m,4H).

7.4. 4-N-BUTYLOXY-6-FORMYL-(NBU-]SPIRO [BENZOFURAN-2(3H)-CYCLOHEXANE] (53b)

Preparation of 53b

Sodium hydride (50% in mineral oil, 62 mg, 2.58 mmol) was washed with hexane (30 ml) under N$_2$, then dry DMF (5 ml) was added. To the mixture, a solution of 52 (0.3 g, 1.29 mmol) in dry DMF (10 ml) was added dropwise. The mixture was stirred for 30 min. A solution of n-butyl p-toluenesulfonate (0.29 g, 1.29 mmol) in DMF (5 ml) was added dropwise. The mixture was warmed to 50° C. and stirred for 2 h. Ether (50 ml) was added to the mixture which was washed with H$_2$O (50 ml×2), dried and concentrated to give a crude product. Purification by chromatography (1:4 ether/hexane) afforded a pale yellow liquid as 53b, yield 0.27 g (73%). TLC $R_f$ 0.58 (ether/hexane). IR (neat) 2940, 2860, 1690, 1600, 1430, 1380, 1320, 1210, 1100, 1030, 920, 825, 800, 745 cm$^{-1}$. NMR (CDCl$_3$) δ 9.84 (s,2H), 6.92 (s,1H), 6.87 (s,1H), 4.07–4.03 (t,2H), 2.94 (s,2H), 1.87–1.64 (m,8H), 1.58–1.43 (m,6H), 1.01–0.96 (t,3H).

7.5. 6-FORMYL-4-PHENOXYSPIRO [BENZOFURAN-2(3H)-CYCLOHEXANE] (53c)

Preparation of 53c

Under N$_2$ condition, a solution of 52 (0.4 g, 1.72 mmol) in CH$_2$Cl$_2$ was added to a mixture of triphenylbismuth diacetate (1.16 g, 2.08 mmol) and copper powder (11 mg, 0.17 mmol) in CH$_2$Cl$_2$ (50 ml). The mixture was stirred at 25° C. for 24 h, then filtered through silica gel and rinsed with 10% EtOAc in CH$_2$Cl$_2$ solution (20 ml). The solution was washed with H$_2$O (50 ml), dried and concentrated to give the crude product (0.65 g), which then was purified by chromatograhy (1:4 ether/hexane) to afford a colorless liquid as 53c; yield 0.4 g (75%). TLC $R_f$ 0.59 (1:4 ether/hexane). IR (neat) 3060, 2940, 2860, 1695, 1580, 1485, 1430, 1310, 1215, 1050, 1020, 850, 800, 755, 690 cm$^{-1}$. NMR (CDCl$_3$) δ 7.40–6.89 (m,7H), 2.93 (s,2H), 1.90–1.63 (m,6H), 1.55–1.42 (m,4H).

7.6. 6-FORMYL-4-(2'-HYDROXYETHYLOXY) SPIRO[BENZOFURAN-2(3H)-CYCLOHEXANE] (53d)

Preparation of 53d

Sodium hydride (50% in mineral oil, 0.10 g, 2.15 mmol) was washed with hexane (50 ml) under N$_2$. Dry DMF (15 ml) was added and a solution of 52 (0.50 g, 1.29 mmol) in DMF (10 ml) was added slowly at 25° C. After stirring for 30 min, a solution of 2-[(tertbutyldimethylsilyl)oxy]ethyl bromide in DMF (5 ml) was added dropwise. The mixture was warmed to 50° C. and stirred for 3 h more. Ether (50 ml) was added to the mixture, which was then washed with water (50 ml×3). The ether layer was collected, dried and concentrated to give a crude product (0.9 g). Purification by chromatography (1.5:8.5 ether/hexane) gave a pale yellow solid 0.70 g (83%). TLC $R_f$ 0.50 (1:4 ether/hexane). mp 74°–75° C. IR (KBR) 2940, 2860, 1695, 1600, 1440, 1390, 1330, 1220, 1140, 1110, 1095, 960, 830, 780 cm$^{-1}$. NMR (CDCl$_3$) δ 9.84 (s,1H), 6.93 (s,1H), 6.89 (s,1H), 4.13 (t,2H), 3.98 (t,2H), 2.95 (s,2H), 1.87–1.45 (m,10H), 0.91 (s,9H), 0.10(s,6H).

The above product (0.31 g, 0.79 mmol) was dissolved in THF (5 ml), then tetrabutylammonium fluoride (1 ml, 1.0 mmol, 1.0M in THF solution) was added, solution was stirred at 25° C. for 2 h. Ether (30 ml) was added, and the solution was washed with water (50 ml). The ether layer was collected, dried and concentrated to afford a pale yellow liquid. Purification by chromatography (1:4 hexane/ether) gave a pale yellow liquid as 53d. Yield, 0.17g (77%). TLC $R_f$ 0.34 (1:4 hexane/ether). IR (neat) 3450(b), 2940, 2870, 1690, 1600, 1440, 1390, 1325, 1220, 1130–1070(b), 1035, 925, 830, 810, 755 cm$^{-1}$. NMR (CDCl$_3$) δ 89.84 (s,1H), 6.93 (s,1H), 6.91 (s,1H), 4.18 (t,2H), 4.00 (t,2H), 2.97 (s,2H), 1.87–1.64 (m,6H), 1.49 (s,b,4H).

7.7. 6-FORMYL-4-P-NITROPHENOXYSPIRO [BENZOFURAN-2(3H)-CYCLOHEXANE] (53e)

Preparation of 53e

Sodium hydride (50% in mineral oil, 0.10 g, 4.58 mmol) was washed with hexane (20 ml) under nitrogen, and dry DMF (50 ml) was added. To the mixture, a solution of 52 (0.50 g, 2.15 mmol) in DMF (15 ml) was added slowly at 25° C. The mixture was stirred for 30 min. A solution of 1-fluoro-4-nitrobenzene in DMF (10 ml) was added slowly. The mixture was then warmed to 35° C. and stirred for 3 h. Ether (100 ml) was added to the mixture after cooling to 25° C. which was washed with water (50 ml×3). Ether layer was collected, dried and concentrated to give a crude product (0.79 g). Purification by chromatography (1:9 EtOAc/hexane) afforded a yellow sticky oil as expected product 53e. Yield, 0.41 g (54%). TLC $R_f$ 0.32 (1:4 EtOAc/hexane). IR (neat) 2940, 2860, 1695, 1570, 1515, 1490, 1430, 1345, 1310, 1240, 1165, 1110, 1065, 1050, 1025, 920, 865, 850, 800, 750, 745 cm$^{-1}$. NMR (CDCl$_3$) δ 9.86(s,1H), 8.26–8.23 (d,1H), 7.06 (s,1H), 7.06–7.03 (m,3H), 2.86 (s,2H), 1.90–1.40 (m,10H).

7.8. 6-FORMYL-4-P-FORMYLPHENOXYSPIRO [BENZOFURAN-2(3H)-CYCLOHEXANE] (53f)

Preparation of 53f

Sodium hydride (50% in mineral oil, 103 mg, 4.31 mmol) was washed with hexane (20 ml) under N$_2$. Dry DMF (30 ml) was added and a solution of 52 (0.40 g, 1.72 mmol) in DMF (5 ml) was added slowly at 25° C., and a solution of p-fluorobenzaldehyde in DMF (5 ml) was added. The mixture was warmed to 50° C. and stirred for 24 h. After cooling to 25° C., ether (100 ml) was added, the solution was washed with water (30 ml×3). The ether layer was collected, dried and concentrated to give a crude product. Purification by chromatography (1:9 EtOAc/hexane) gave a pale yellow solid as expected product 53f. Yield, 0.31 g (53%). 53f: mp 127°–129° C. TLC $R_f$ 0.53 (1:4 EtOAc/hexane). IR (KBR) 2940, 2840, 1680, 1560, 1500, 1440, 1390, 1320, 1220, 1170, 1050, 840, 800 cm$^{-1}$. NMR (CDCl$_3$) δ 9.95 (s,1H), 9.85 (s,1H), 7.90–7.87 (d,2H), 7.12 (s,1H), 7.10–7.07 (d,2H), 7.04 (s,1H), 2.87 (s,2H), 1.90–1.40 (m, 10H).

7.9. 6-FORMYLSPIRO[BENZOFURAN-2(3H) - CYCLOHEXANE] (53g)

Preparation of 53g

Pyridine (0.34 g, 4.31 mmol) and 52 (0.50 g, 2.15 mmol) were dissolved in methylene chloride (50 ml) and cooled at 0° C. under N$_2$. Triflic (trifluoromethanesulfonic) anhydride (0.40 ml, 2.37 mmol) was introduced dropwise by syringe. The solution was stirred for 1 h at 0° C. The solution was then washed with 5% aq. HCl (10 ml) and water (30 ml×3), dried and concentrated to give a crude product, which was purified by chromatography (1:9 EtOAc/hexane) to afford the expected product phenol triflate 52. Yield, 0.70 g (90%). Phenol triflate 52: TLC $R_f$ 0.74 (1:4 EtoAc/hexane). IR (neat) 2940, 2860, 1710, 1625, 1590, 1430, 1300, 1250–1200(b), 1140, 1010, 980, 920, 850, 830, 800, 770 cm$^{-1}$. NMR ((CDCl$_3$) δ 9.89 (s,1H), 7.25 (s,2H), 3.12 (s,2H), 1.92–1.44 (m,–10H).

Phenol triflate 52 (1.00 g, 2.74 mmol), triphenylphosphine (58 mg, 0.22 mmol), palladium acetate (25 mg, 0.11 mmol) and triethylamine (1.66 g, 16.4 mmol) were dissolved in DMF (10 ml) and 96% formic acid (0.50 g, 10.8 mmol) in DMF (2 ml) was added. The mixture was stirred at 60° C. for 2 h under N$_2$. The mixture was diluted with water (50 ml) and extracted with ether (50 ml×3). The ether layer was collected, dried and concentrated to give a brown residue. The crude product was purified by chromatagraphy (1:9 EtOAc/hexane) to give the expected product 53g as a pale yellow oil. Yield, 0.29 g (49%). 53g: TLC $R_f$ 0.69 (1:9 EtOAc/hexane). IR (neat) 2940, 2860, 1690, 1585, 1490, 1440, 1340, 1310, 1270, 1250, 1150, 1030, 950, 920, 870, 800, 785 cm$^{-1}$. NMR (CDCl$_3$) δ 9.90 (s,1H), 7.36–7.33 (d,1H), 7.28–7.26 (d,1H), 7.22 (s,1H), 3.02 (s,1H), 1.89–1.43(m, 10H).

7.10. 4-BENZYLOXY-6-CARBOXYLSPIRO [BENZOFURAN-2(3H)-CYCLOHEXANE] (54a); 4-N-BUTYLOXY-6-CARBOXYLSPIRO [BENZOFURAN-2(3H)-CYCLOHEXANE] (54b); 6-CARBOXYL-4-PHENOXYSPIRO [BENZOFURAN-2(3H)-CYCLO HEXANE] (54c); 6-CARBOXYL-4-(2'-HYDROXYETHYLOXYSPIRO[BENZOFURAN-2 (3H)-CYCLOHEXANE] (54d); AND 6-CARBOXYL-4-P-NITROPHENOXYSPIRO [BENZOFURAN-2(3H)-CYCLOHEXANE] (54e)

Preparation of 54a–e

Procedure for preparation of these compounds was essentially that used for 43. For 54a: mp 173°–175° C.; yield, 74–83%; TLC $R_f$ 0.56 (1:4 hexane/ether). IR (KBr) 3100–2500, 1680, 1600, 1420, 1320, 1215, 1095, 950, 735cm$^{-1}$. NMR (CDCl$_3$) δ 7.46–7.34 (m,5H), 7.26 (s,1H), 7.18 (s,1H), 5.13 (s,2H), 2.97 (s,2H), 1.86–1.65 (m,6H), 1.48 (s,br,4H). Anal. Calcd for C$_{21}$H$_{22}$O$_4$: C, 74.53; H, 6.55. Found: C,74.44; H, 6.57.

For 54b: mp 145°–147° C.; yield, 81%; TLC $R_f$ 0.62 (1:4 hexane/ether). IR (KBr) 3100–2500, 1670, 1600, 1425, 1320, 1275, 1210, 1100, 1030, 940, 865, 765, 745cm$^{-1}$. NMR (CDCl$_3$) δ 7.14 (s,2H), 4.06–4.02 (t,2H), 2.94 (s,2H), 1.86–1.65 (m,8H), 1.56–1.44 (m,6H), 1.01–0.97 (t,3H).

Anal. Calcd for C$_{18}$H$_{24}$O$_4$: C, 71.01; H, 7.95. Found C, 71.01; H, 7.97.

For 54c mp 173°–175° C.; yield, 71%; TLC $R_f$ 0.69 (1:4 hexane/ether). IR (KBr) 3100–2500, 1680, 1580, 1480, 1420, 1310, 1205, 1050, 950, 865, 765, 685 cm$^{-1}$. NMR (CDCl$_3$) δ 7.37–6.97 (m,7h), 2.90 (s,2H), 1.90–1.60 (m,6H), 1.50–1.40 (m,4H). $^{13}$C NMR (CDCl$_3$) δ 171.45, 160.88, 156.32, 153.39, 130.62, 129.86, 123.74, 123.56, 118.44, 112.37, 106.59, 90.34, 38.70, 37.11, 25.02, 22.90. Anal. Calcd for C$_{20}$H$_{20}$O$_4$: C,74.05; H, 6.22. Found: C, 73.97; H, 6.25.

For 54d

Reaction was stirred for 8 h at 50° C. 54d: mp 163°–164° C.; TLC $R_f$ 0.72 (1:19 MeOH/ether); yield, 94%. IR (KBr) 3600–3300(b), 2940, 2860, 1690, 1600, 1430, 1325, 1320, 1115, 1070, 960, 755, 725 cm$^{-1}$. NMR (CDCl$_3$) δ 57.15 (s,1H), 7.14 (s,1H), 4.18 (t,2H), 3.99 (t,2H), 2.96 (s,2H) 1.87–1.65 (m,6H), 1.49 (s,b, 4H). $^{13}$C NMR (CDCl$_3$) δ 171.24, 160.26, 155.23, 130.28, 120.61, 105.44, 105.36, 90.21, 69.46, 61.43, 38.48, 37.23, 25.05, 22.96. Anal. Calcd for C$_{16}$H$_{20}$O$_5$: C,65.74; H,6.90. Found: C,65.58; H,6.96.

For 54e

Mixture was stirred for 24 h at 50° C. Yield, 56%. 54e: mp 190°–191° C.; TLC $R_f$ 0.80 (ether). IR (KBr) 3100–2500(b), 1690, 1585, 1525, 1490, 1425, 1390, 1310, 1230, 1170, 1115, 1070, 1025, 960, 860, 850, 770, 755 cm$^{-1}$ NMR ((CDCl$_3$) δ 8.25–8.22 (d,2H), 7.36 (s,1H), 7.29 (s,1H), 7.04–7.01 (d,2H), 2.84 (s,2H), 1.90–1.40 (m,10H). $^{13}$C NMR (CDCl$_3$) δ 170.45, 161.92, 161.35, 150.96, 143.03, 131.22, 126.12, 124.98, 116.93, 113.98, 108.45, 90.76, 38.66, 37.05, 25.04, 24.91, 22.81. Anal. Calcd. for C$_{20}$H$_{19}$NO$_6$: C, 65.03; H, 5.18; N,3.79. Found: C, 64.96; H, 5.23; N, 3.71.

7.11. 6-CARBOXYLSPIRO[BENZOFURAN-2(3H) -CYCLOHEXANE] (54g); AND 4-P-AMINOPHENOXY-6-CARBOXYLSPIRO [BENZOFURAN-2(3H)-CYCLOHEXANE] (54h); 6-CARBOXYL-4-P-CARBOXYLPHENOXYSPIRO[BENZOFURAN-2 (3H)-CYCLOHEXANE] (54i)

54g

Mixture was stirred at 60° C. for 4 h. Yield, 84%. mp 154°–155° C. TLC $R_f$ 0.82 (ether). IR (KBR) 3200–2500(b), 1680(b), 1590, 1440, 1390(b), 1090, 1030, 950, 780, 770 cm$^{-1}$. NMR (CDCl$_3$) δ 7.62–7.60 (d,1H), 7.44 (s,1H), 7.21–7.19 (d,1H), 3.01 (s,1H), 1.89–1.43 (m,10H). Anal. Calcd for C$_{14}$H$_{16}$O$_3$: C, 72.39; H,6.94. Found: C, 72.31; H, 6.95.

54h 54e (30 mg, 0.81 mmol) dissolved in MeOH (10 ml) and 10% Pd-C (20 mg) was added. H$_2$ gas was bubbled through the mixture for 5 h at 25° C. The mixture was filtered and MeOH was removed to give a brown oil. The crude product was purified by preparative TLC plate (1:19 MeOH/CH$_2$Cl$_2$) to afford a pale yellow solid as product 54h. Yield, 10 mg (36%). 54h: mp 193°–195° C. TLC $R_f$ 0.49 (1:9 MeOH/CH$_2$Cl$_2$). IR (KBr) 3380, 3320, 2940. 2860, 1700, 1600, 1510, 1420, 1320, 1290, 1270, 1210, 1200, 1050, 950, 920, 770 cm$^{-1}$. NMR (CDCl$_3$) δ 7.15 (s,1H), 7.00 (s,1H), 6.87–6.84 (d,2H), 6.87–6.84 (d,2H), 2.94 (s,2H), 1.88–1.43 (m,10H). MS m/z (relative intensity) 339(100), 322(2), 296(5), 282(7), 258(29), 217(61), 196(11), 167(15), 156(7), 130(9), 108(29), 93(95).

54i

Procedure for preparation of these compounds was essentially that used for 43. Mixture was stirred for 24 h at 60° C. The crude product was treated with CH$_2$N$_2$ which then was purified by chromatography (1:4 EtOAc/hexane) to give the dimethyl ester of 54i. Yield, 0.18 g (51%). Dimethyl ester of 54i: IR (neat) 2940, 2860, 1750, 1590, 1500, 1430, 1350, 1310, 1280, 1250, 1220, 1160, 1110, 1080, 1070, 1050, 1030, 1000, 920, 880, 850, 770, 690 cm$^{-1}$. NMR (CDCl$_3$) δ 8.03–8.00 (d,2H), 7.26 (s,1H), 7.21 (s,1H), 6.98–6.95 (d,2H), 3.91 (s,3H), 3.86 (s,3H), 2.82 (s,2H), 1.88–1.39 (m,10H).

The dimethyl ester of 54i (0.15 g, 0.38 mmol) was dissolved in THF (10 ml), then a solution of 2N NaOH (5 ml) was added. The solution was warmed to 50° C. and stirred for 3 h. After cooling to 25° C., the aq. solution was rinsed with ether (20 ml) and the aq. solution was acidified with conc. HCl. A white precipitate resulted, which was extracted with ether (50 ml×2). After the precipitate was dried and concentrated, a white solid was resulted as product 54i. Yield, 0.13 g (93%). 54i mp 278°–280° C. TLC R$_f$ 0.29 (1:9 MeOH/CH$_2$Cl$_2$). IR (KBr) 3200–2400(b), 1690, 1605, 1590, 1505, 1425, 1315, 1280, 1220, 1170, 1050, 950, 915, 880, 850, 770, 740, 720cm$^{-1}$. NMR (MEOH-d$_4$) δ 8.05–8.02 (d,2H), 7.18 (s,1H), 7.15 (s,1H), 7.03–7.00 (d,2H), 2.84 (s,2H), 1.86–1.43 (m,10H). $^{13}$C NMR (MeOH-d$_4$) δ 169.21, 168.97, 162.48, 162.13, 153.28, 133.91, 133.13, 126.71, 124.86, 118.09, 114.23, 108.04, 91.47, 39.76, 37.98, 26.09, 23.90. Anal. Calcd for C$_{21}$H$_{20}$O$_6$: C, 68.47; H, 5.47. Found: C, 68.22; H, 5.48.

7.12. SODIUM SALTS OF 4-BENZYLOXY-6-CARBOXYLSPIRO[BENZOFURAN-2(3H)-CYCLOHEXANE] (55a); 4-N-BUTYLOXY-6-CARBOXYLSPIRO[BENZOFURAN-2(3H)-CYCLOHEXANE] (55b); 6-CARBOXYL-4-PHENOXYSPIRO[BENZOFURAN-2(3H)-CYCLOHEXANE] (55c); 6-CARBOXYL-4-(2'-HYDROXYETHYLOXYSPIRO[BENZOFURAN-2 (3H)-CYCLOHEXANE] (55d); 6-CARBOXYL-4-P-NITROPHENOXYSPIRO [BENZOFURAN-2 (3H)-CYCLOHEXANE] (55e); 6-CARBOXYLSPIRO[BENZOFURAN-2(3H)-CYCLOHEXANE] (55g); AND 6-CARBOXYL-4-P-CARBOXYLPHENOXYSPIRO [BENZOFURAN-2(3H)-CYCLOHEXANE] (55i)

Preparation of 55a–e,g,i

Procedure for preparation of these compounds was essentially that used for 44. NMR spectra for 55a–g are listed as below. 55a: NMR (D$_2$O) δ 7.21–6.88 (s,7H), 4.85 (s,2H), 2.56 (s,2H), 1.43–1.06 (m,10H). 55b: NMR (D$_2$O) δ 7.10 (s,1H), 6.90 (s,1H), 4.13 (t,2H), 2.93 (s,2H), 1.79–1.67 (m,8H), 1.50–1.41 (m,6H), 0.93 (t,3H). 55c: NMR (D$_2$O) δ 7.20–6.80 (m,7H), 2.61 (s,2H), 1.60–1.12 (m,10H). 55d: NMR (D$_2$O) δ 7.07 (s,1H), 6.92 (s,1H), 4.18 (t,2H), 3.93 (t,2H), 2.96 (s,2H), 1.68 (s, b, 6H), 1.44(s, b, 4H). 55e: NMR (D$_2$O) δ 8.10–8.07 (d,2H), 7.13 (s,1H), 7.11 (s,1H), 6.98–6.95 (d,2H), 2.68 (s,2H), 1.70–1.23 (m,10H). 55i: NMR (D$_2$O) 7.90–7.87 (d,2H), 7.14 (s,1H), 7.12 (s, 1H), 7.00–6.97 (d,2H), 2.76 (s,2H), 1.70–1.27 (m,10H). 55g: NMR (D$_2$O) δ 7.45–7.42 (d,1H), 7.23–7.20 (m,2H), 2.93 (s,2H), 1.65 (s, b, 6H), 1.41 (s,b, 4H). $^{13}$C NMR (D$_2$O) δ 177.63, 160.05, 139.25, 133.68, 127.83, 124.60, 112.09, 93.64, 42.45, 38.96, 27.15, 25.37.

8. EXAMPLES OF 6,7-DISUBSTITUTED-4-METHOXYSPIRO[BENZOFURAN-2 (3H)-CYCLOHEXANES]

The melting points were measured with a Thomas Hoover apparatus, and are uncorrected; the infrared spectra were obtained with the aid of a Perkin Elmer 281B spectrophotometer, the $^1$H NMR spectra were recorded in deuteriochloroform, unless another solvent is specified, either at 90 MHz, in a Varian EM 390 apparatus, or at 300 MHz in a Varian VXR 300 spectrometer. The $^{13}$C NMR were recorded at 75.4 MHz in a Varian VXR 300 spectrometer. All the signals are reported in ppm, downfield from tetramethylsilane, used as internal reference. The multiplicities of the signals are abbreviated as: s=singlet, d=doublet, t=triplet, q=quartet, m=multiplet, b=broad signal. The low resolution mass spectra were obtained from a Finnigan 3221-F200 spectrograph, at 70 eV. The elemental analyses were done by Atlantic Mirolab, Inc. (Norcross, Ga.). The HRMS was obtained at Massachusetts Institute of Technology.

All the solvents and chemicals used were of good quality. In several cases, some of them were purified and/or dried following preestablished procedures. All the reactions were carried out under a dry nitrogen atmosphere. The column chromatographies were done using MN Silica gel 60, under atmospheric pressure, using different solvent systems (hexane-ether, hexane-ethyl acetate), in which increasing quantities of the second solvent were periodically added to the first solvent, or on a chromatotron. One percent acetic acid was added during the chromatographies of carboxylic acids.

8.1. SYNTHESIS OF 7-CARBOXY-6-FORMYL-4-METHOXY PIRO[BENXOFURAN-2 (DH)-CYCLOHEXANE (62)

Preparation of 58

A solution of n-butyllithium in hexane (32.67 ml, 65.34 mmol) was added dropwise to a cold solution (0° C.) of 3,5-dimethoxybenzyl alcohol (56, 5 g, 29.7 mmol) and TMEDA (5.67 ml, 35.64 mmol) in THF (300 ml). After stirring at 0° C. for 15 min and at room temperature for 90 min, the reaction was cooled to −45° C. and copper (I) iodide was added (7054 mg, 37.13 mmol). One hour later, the electrophile 57 (prepared as described in J. Heterocyclic. Chem. 26, 879–891 (1989)] was added via syringe. After stirring overnight at room temperature, concentrated ammonium hydroxide (100 ml) was added, and the reaction products were extracted with ethyl acetate (4×150 ml). The combined organic phases were dried over MgSO$_4$, the solvent was evaporated in vacuo and the remaining oil was chromatographed yielding 58 (6678 mg, 25.49 mmol, 86%) as a viscous oil, which crystalized on standing. This was recrystallized (hexane ether) giving a white solid mp. 61°–63° C.; IR (KBr): 3290, 2930, 1590, 1460, 1425, 1210, 1140, y 1120 cm$^{-1}$; $^1$H NMR: 1.56 (m, 4H), 1.93 (m, 4H), 2.62 (bs, 1H, exc), 3.26 (bs, 2H), 3.79 (s, 6H), 4.59 (s,2H), 5.20 (bs, 1H), and 6.54 (s, 1H); $^{13}$C NMR: 22.5, 23.1, 25.3, 28.8, 30.6, 55.8, 65.7, 102.5, 116.6, 119.9, 136.3, 139.8, and 158.5; Elemental analysis: calcd. C=73.25, H=8.45; obsd. C=73.21, H=8.52.

Preparation of 59

A solution of n-butyllithium in hexane (4.2 ml, 8.4 mmol) was added to compound 58 (1000 mg, 3.82 mmol) in hexane (50 ml) and TMEDA (0.69 ml, 4.58 mmol). After stirring at 0° C. for 15 min and at room temperature for 90 min, the resulting suspension was cooled to −78° C. and dry carbon dioxide was bubbled for 1 hr at −78° C. and during 1 hr at room temperature. After adding 2N NaOH (25 ml), the unreacted material was extracted with ether and the extracts were discarded. The aqueous phase was acidified with 6N HCl and the reaction products were extraced with ether (4×50 ml). After drying (MgSO$^4$) and concentration in vacuo of the organic phase, 59 (727 mg, 2.52 mmol, 66%) was recovered as a solid mp. 103°–104.5° C. (recrystallized from hexane-ether); IR (KBr): 3000–2820, 1740, 1600, 1460, 1420, 1340, 1240, 1200, 1090, 1015, and 940 cm$^{-1}$; $^1$NMR: 1.48–2.00 (m, 8H), 3.30 (s, 2H), 3.88 (s, 3H), 4.03 (s, 3H), 5.19 (bs, 1H), 5.19 (s, 2H), and 6.64 (s, 1H); $^3$C NMR: 22.5, 23.1, 25.3, 28.9, 31.0, 56.2, 62.6, 68.8, 98.7, 109.8, 121.0, 123.0, 136.2, 148.8, 158.4 and 164.3; Elemental analysis: calcd. C=70.83, H=6.94; C=70.77, H=6.97.

Preparation of 60

A solution of 59 (470 mg, 1.63 mmol) was demethylated until no more starting material was left, according to the TLC. The reaction products were extracted with ethyl acetate (4×40 ml), then dried (MgSO4), concentrated in vacuo and purified to yield 60 (332 mg, 1.21 mmol, 74%) as a white solid mp. 150°–151.5° C. (recrystallized from hexane-ether); IR (KBr): 3420, 3000–2800, 1720, 1600, 1465, 1345, 1280, 1250, 1195 and 1075; $^1$H NMR: 1.45–2.00 (m, 8H), 3.27 (s, 2H), 3.88 (s, 3H), 5.2 (s, 2H), 6.5 (s, 1H) and 7.71 (s, 1H); $^{13}$C NMR: 22.4, 23.0, 25.2, 28.7, 30.2, 56.2, 70.4, 96.1, 104.2, 115.5, 120.9, 135.4, 146.2, 155.0, 165.2 and 172.8.

Preparation of 61

Amberlyst 15 (290 mg, 2 g/mmol) was added to a solution of 60 (40 mg, 0.146 mmol) in dry methylene chloride (2.9 ml, 20 ml/mmol) after stirring overnight at room temperature, the solvent was filtered through a short column of silica gel, the solids were washed with ethyl acetate and the filtrate was filtered through silica gel. The combined filtrates were concentrated in vacuo and chromatographed, affording 61 (38 mg, 0.139 mmol, 95%) as a solid mp. 132°–134° C. (recrystallized from hexane-ether); IR (KBr): 2980–2820, 1740, 1610, 1440, 1330, 1280, 1260, 1235, 1205, 1145, 1080, 1010, 930 and 780 cm$^{-1}$, $^1$NMR: 1.35–2.00 (m, 10H), 2.89 (s, 2H), 3.91 (s, 3H), 5.20 (s, 2H) and 6.46 (s, 1H); $^{13}$C NMR: 23.1, 25.0, 37.1, 55.9, 69.8, 93.7, 96.0, 102.0, 114.8, 150.2, 157.8, 162.1 and 169.6; Elemental analysis: calcd. C=70.04, H=6.62; obsd. C=70.11, H=6.62.

Preparation of 62

Compound 61 (211 mg, 0.77 mmol) was dissolved in THF (4 ml) and the resulting solution was added to a solution of 10N NaOH (6 ml, 60 mmol) and FTBA (1 ml, 1 mmol). Potassium permanganate was (KMnO$_4$) added to the system until no more starting material was observed by TLC. The excess of KMnO$_4$ was destroyed with sodium sulfite and the reaction was acidified with 6N H$_2$SO$_4$. The organic material was extracted with ethyl acetate (4×50 ml), the extracts were dried (MgSO$_4$), concentrated in vacuo and chromatographed yielding 62 (120 mg, 0.41 mmol, 53%) as a white solid mp. 128°–130° C. (recrystallized from hexane-ether); IR (KBr): 2950, 2850, 1830, 1770, 1625, 1455, 1340, 1270, 1210, 1145, 990, 985 and 745 cm$^{-1}$; $^1$NMR: 1.35–1.95 (m, 10H), 2.86 (s, 2H), 3.91 (s, 3H), 5.90 (bs, 1H), 6.53 (s,1H) and 6.61 (s, 1H); $^{13}$C NMR: 23.1, 24.9, 37.0, 37.1, 56.0, 93.9, 97.3, 98.0, 102.6, 116.4, 150.1, 157.3, and 162.1 and 167.6; Elemental analysis: calcd. C=66.20, H=6.25; obsd. C=66.03, H=6.18.

8.2. SYNTHESIS OF 6-CARBOXY-7-FORMYL-4-METHOXYSPIRO[BENZOFURAN-2(3H)-CYCLOHEXANE (68) AND 6,7-DICARBOXYL-4-METHOXYSPIRO [BENZOFURAN-2(3H)-CYCLOHEXANE] (66)

Preparation of 65

A solution of n-butyllithium in hexane (2.20 ml, 4.95 mmol) was added to a solution of N,N,N' trimethylethyl-enediamine (0.65 ml, 5.09 mmol) in THF (6 ml) at −20° C. (CCl$_4$/CO$_2$). After 30 min, 11b (1170 mg, 4.76 mmol, prepared as described in section 6.8 supra) in THF (4 ml) was added dropwise, followed 30 min later by n-BuLi (6.35 ml, 14.28 mmol). The resulting system was kept at −20° C. for 24 h, and DMF was added (02.20 ml, 28.56 mmol). After 24 h reaction period, the reaction products were partitioned between ether (4×50 ml) and brine (50 ml), chromatography of the extracts gave 65 (1135 mg, 4.14 mmol, 87%) as a solid mp. 129°–131° C. (recrystallized from hexane-ether); IR (KBr): 3000–2840, 1670, 1600, 1470, 1425, 1390, 1320, 1280, 1260, 1210, 1130, 1030, 890, 850, 770, 700 and 620 cm$^{-1}$; $^1$H NMR: 1.40–1.93 (s, 10H), 2.93 (s, 2H), 3.94 (s, 3H) 7.04 (s, 1H), 10.35 (s, 1H) and 10.70 (s, 1H); $^{13}$C NMR: 22.9, 24.9, 37.2, 37.7, 56.0, 93.0, 103.6, 113.7, 120.2, 138.7, 160.3, 164.7, 188.6 and 192.6; Elemental analysis: calcd. C=70.06, H=6.61; obsd. C=69.84, H=6.65.

Preparation of 68

A 4N solution of potassium hydroxide (52.92 mmol) was added dropwise to a stirred solution of compound 65 (2900 mg, 1058 mmol) in THF (10 ml) and water (7 ml) containing dissolved silver nitrate (3777 mg, 22.22 mmol, 1.05 eq.) at room temperature. The reaction system was protected from direct light. After stirring for 2 h at room temperature, the solids were filtered and extensively washed with distilled water. 2N H$_2$SO$_4$ was added until pH 3, and the reaction products were extracted with ether (3×150 ml), washed with brine (2×25 ml) and dried (MgSO$_4$). Chromatography of the reaction products allowed the recovery of the starting material (1823 mg, 63%), compound 68 (326 mg, 1.12 mmol, 11%, 29% corrected yield) and compound 66 (614 mg, 2.01 mmol, 19%, 51%). Compound 68: mp: 148°–150° C. (rec. from hexane-ether); IR (KBr): 3440, 3000–2840, 1740, 1630, 1450, 1345, 1290, 1270, 1150, 1105, 1010, 910, 860, 770, 690, cm$^{-1}$; $^1$H NMR (DMSO d$_6$): 1.30–1.52 (m, 4H), 1.62–1.81 (m, 6H), 2.91 (s, 2H), 3.87 (s, 3H), 6.55 (bs, 1H), 6.85 (s, 1H), and 7.95 (bs, 1H); $^{13}$C NMR (DMSO d$_6$): 22.52, 24.47, 36.57, 37.56, 55.86, 91.90, 96.33, 98.34, 120.60, 121.48, 128.99, 154.0–3, 158.28, 168.42; MS (e/m, %): 290 (M+, 89), 289 (72), 272 (100), 271 (88), 244 (65), 215 (78), 192 (98), 191 (95), 190 (65), 165 (93), 164 (82), 79 (89). Elemental analysis: calcd. C=66.20, H=6.25; obsd. C=66.19, H=6.26.

Direct Preparation of 66

To a solution 65 (153 mg, 0.56 mmol) in ethanol (5 ml), was added a solution of silver nitrate (222 mg, 1.30 mmol) in distilled water (1 ml), followed by KOH (3 ml, 2.99 mmol). The system was stirred overnight at room temperature, shielded from the light, then it was filtered and the residue was carefully washed with water. The combined aqueous phases were extracted with ether, the aqueous phase was then acidified and extracted with ether (3×25 ml); the combined organic phases were dried and chromatographed to afford 66 (156 mg, 0.51 mmol, 91%) as a white solid mp. 188°–190° C. (recrystallized from acetone); IR (KBr): 3500–2400, 3000–2850, 1700, 1610, 1410, 1330, 1290, 1130, 1040, 1000, 930, 855, 750 and 660 cm$^{-1}$: $^1$H NMR: (acetone d$_6$): 1.40–1.90 (m, 10H), 2.93 (s, 2H), 3.91 (s, 3H) and 6.95 (s, 2H); $^{13}$C NMR: (acetone d$_6$): 23.5, 25.6, 37.6, 38.7, 56.1, 91.7, 105.1, 111.6, 118.8, 133.0, 157.8, 158.8, 167.2 and 186.1; Elemental analysis: calcd. C=62.74, H=5.92; obsd. C=62.66, H=6.01.

8.3. SYNTHESIS OF 4-METHOXY-5a,6,8,8a-TETRAHYDROSPIRO[BENZO(2,1-b:3,4-C'] DIFURAN-2(8H)CYCLOHEXAN]-6,8-DIONE; 6, 7-DIHYDROXYMETHYL-4-METHOXYSPIRO [BENZOFURAN-2(3H)CYCLOHEXANE]; AND 4-METHOXYSPIRO[BENZO[2,1-B:3,4-C'] DIFURAN-2(3H)-CYCLOHEXAN]-6(8H)-ONE

Preparation of 63

A cold and stirred solution of 62 (150 mg, 0.52 mmol) in acetone (10 ml) was treated with excess of Jones reagent (Bowden et al., 1946, J. Chem. Soc. 39; Bowers et al., 1953, J. Chem. Soc., 2548) until the starting material was completely converted (TLC). The excess reagent was destroyed with isopropanol, brine was added (30 ml) and the reaction products were extracted with ethyl acetate (4×50 ml) the extracts were dried (MgSO$_4$), concentrated in vacuo and chromatograhphed yielding 63 (134 mg, 0.46 mmol, 89%) as a white solid mp. 197°–198.5° C. (recrystallized from acetone); IR (KBr): 3400, 2940, 2860, 1740, 1620, 1450, 1330, 1235, 1140, 1090, 1020, 930 and 760 cm$^{-1}$; $^1$H NMR (acetone d$_6$): 1.45–1.95 (m, 10H), 3.03 (s, 2H), 4.08 (s, 3H), 7.15 (s, 1H); $^{13}$C NMR (acetone d$_6$): 23.5, 25.5, 37.7, 38.3, 57.2, 95.6, 102.1, 123.9, 134.9, 158.4, 161.2, 163.8 and 164.2; MS (m/z, %): 288 (M+, 40), 287 (32), 231 (40), 208 (49), 207 (52), 85 (27), 81 (100), 77 (36), 71 (28), 69 (42), 57 (67) and 55 (61); HRMS: expected 288.0998 for C$_{16}$H$_{16}$O$_5$, obsd.: 288.0999.

Preparation of 64

A solution of 61 (300 mg, 1.09 mmol) in THF (15 ml) was treated for 3 h with LAH (slight excess). After adding Na$_2$SO$_4$.10H$_2$O and ether, the reaction products were filtered, affording the diol 64 (260 mg, 0.94 mmol, 86%); $^1$H NMR: 1.40–1.90 (m, 10H), 2.93 (s, 2H), 3.83 (s, 3H), 4.66 (s, 2H), 4.70 (s, 2H) and 6.47 (s, 1H).

Preparation of 67

To a solution of 64 (260 mg, 0.935 mmol) in dry methylene chloride (15 ml) BaMno$_4$ (1197 mg, 4.68 mmol) was added and the resulting suspension was stirred for 3 days at room temperature. After recovering the reaction products by partition between brine (30 ml) and ethyl acetate (3×50 ml) it was observed that this was an equimolecular mixture of 67 and 65.

9. COMPLEMENT INHIBITION BY DI- AND TRI-SUBSTITUTED SPIRO[BENZOFURAN-2 (3H)-CYCLOHEXANES]

The 4 substituted spirobenzofuran compounds of example 7 and the disubstituted spirobenzofuran compounds of example 8 were tested for their capacity to inhibit complement-mediated lysis of sheep red blood cells (SRBC) as described in Section 6.6.2 supra with the modification that the human serum used as the complement source was diluted to 1 to 100 in Hepes buffer, instead of 1 to 125. The results of the hemolysis assays are shown in FIG. 8 and Tables XI and XII.

Table XI

Inhibition of Hemolysis by 6,7-disubstituted-4-methoxy spiro[benzofuran-2(3H)-cyclohexanes]

| Compound | Mean | IH$_{50}$ (±SD)* nM | n = |
|---|---|---|---|
| 11a | 1.330 | (±0.490) | 10 |
| 44a | 0.530 | (±0.190) | 23 |
| 62 | 1.670 | (±0.153) | 3 |
| 66 | 0.800 | (±0.356) | 3 |
| 68 | 0.164 | (±0.076) | 7 |
| K76COOH | 0.570 | (±0.170) | 9 |

*The concentration of compound (± standard deviation) required to produce a value for hemolysis inhibition of 0.5 as described in Section 6.36.2 supra.

Table XII

Inhibition of Hemolysis by 6-carboxyl-4-substituted spiro[benzofuran-2(3H)-cyclohexanes]

| Compound | Mean | IH$_{50}$ (± SD)* mM | n = |
|---|---|---|---|
| 31a | 1.45 | (±0.21) | 2 |
| 44a | 0.532 | (±0.193) | 29 |

Table XII-continued

Inhibition of Hemolysis by 6-carboxyl-4-substituted spiro[benzofuran-2(3H)-cyclohexanes]

| Compound | Mean | IH$_{50}$ (± SD)* mM | n = |
|---|---|---|---|
| 44b | 0.580 | (±0.216) | 3 |
| 55a | 2.53 | (±1.00) | 2 |
| 55b | 0.430 | | 1 |
| 55c | 0.280 | (±0.014) | 2 |
| 55d | >2.8 | | 1 |
| 55e | 0.305 | (±0.049) | 2 |
| 55g | 2.320 | (±0.099) | 2 |
| 55h** | 0.320 | (±0.056) | 2 |
| 55i | 1.45 | (±0.44) | 2 |
| K76COOH | 0.570 | (±0.170) | 9 |

*The concentration of compound (± standard deviation) required to produce a value for hemolysis inhibition of 0.5 as described in Section 6.36.2 supra.
**The sodium salt of 4-p-aminophenoxy-carboxyspiro[benzofuran-2(3H)-cyclohexane]

By comparing the inhibition of hemolysis by compounds 62, 66 and 68 as shown in FIG. 8 and Table XI, it can be seen that the particular arrangement of substitutents at positions 6 and 7 of the benzofuran ring is important for antihemolytic activity. By comparing IH$_{50}$ values for the position 4-substituted series as shown in Table XII (for example, the values for 55c, 55e, and 55h), improvements in antihemolytic activity can also be obtained through the optimal choice of the R substituent at position 4. In addition, several of the compounds (see for example, compounds 55c, 55e, 55h and 68 in particular) are more effective in inhibiting complement-mediated hemolysis than is K76COOH. It is anticipated that optimal substituents at position 4, combined with an optimal pair of substituents at position 6 and 7, will result in even more potent complement inhibitors.

10. IN VITRO AND IN VIVO INHIBITION OF COMPLEMENT BY DI- AND TRI-SUBSTITUTED SPIRO[BENZOFURAN-2(3H)-CYCLOHEXANES]

10.1. INTRODUCTION

The role of complement in hyperacute graft rejection has been demonstrated in animal models of both sensitized allograft (Knechtle et al., *J. Heart Transplant.*, 1983, 4:541; Pruitt and Bollinger, *J. Surg. Res.*, 1991, 50:350–355; as well as xenograft transplantation (Adachi et al., *Transplant Proc.*, 1987, 119:1145–1148; Migagawa et al., *Transplantation*, 1988, 46:825; Prewitt et al., 1991, Transplantation 52:868–873). We have chosen an established discordant xenograft model, a guinea pig-to-rat cardiac transplant, to assess the effects of the substituted dihydrobenzofurans on hyperacute rejection in vivo.

10.2. INHIBITION IN VITRO OF RAT AND HUMAN COMPLEMENT

Compounds 68 and 44a were prepared and characterized as described in sections 8.2 and 7.1, respectively. These compounds were demonstrated to inhibit complement-mediated hemolysis using human serum as a complement source, as described in section 6.6.2 and Section 9, supra. Compounds 68 and 44a were also demonstrated to inhibit rat complement using the methods of section 6.6.2, except that rat serum was substituted for human serum as the complement source. A soluble human recombinant complement receptor type 1 (sCR1) was prepared as described (Weisman et al., Science, 1990, 249:146–151; Yeh et al., J. Immunol, 1991; and International Patent Publications No. WO 89/09220 and WO 9/05047, both entitled "The human C3b/C4b receptor (CR1)" Fearon et al.) and used as a positive control the in vitro assays. The results of these studies are summarized in Table XIII.

Table XIII

Inhibition of rat or human complement-mediated hemolysis by substituted spiro[benzofuran-2(3H)-cyclohexanes] and by sCR1

| Compound | $IH_{50}$* for Human Complement | $IH_{50}$ for Rat Complement |
|---|---|---|
| sCR1 | 0.9 nM | 1.5 nM |
| 68 | 100 μM | 2500 μM |
|  | 164 μM | 11,000 μM |
| 44a | 538 μM | 17,300 μM |

*The concentration of compound required to produce a value for hemolysis inhibition of 0.5 as described in Section 6.6.2, supra.

As seen in Table XIII, the human sCR1 protein inhibits rat and human complement with similar potency in this assay. The compounds, on the other hand, more effectively inhibit human than rat complement. Twenty-five- to 70-fold higher concentrations of compound 68 were required to inhibit rat complement-mediated lysis than were required to inhibit human complement-mediated lysis to similar levels.

10.3. INHIBITION OF ALTERNATIVE PATHWAY MEDIATED HEMOLYSIS

The inhibition of sheep red blood cell lysis as described in section 6.6.2 predominantly reflects on classical complement pathway activation since it is initiated by the antigen-antibody complexes on the surface of the sensitized erythrocytes. The assay probably includes a minor contribution from alternative pathway activation as well.

The capacity of the substituted dihydrobenzofurans to inhibit the alternative complement pathway was assessed using the modified method of Platts-Mills and Ishizaka, 1974, J. Immunol., 113:348–358. Essentially, rabbit erythrocytes were lysed using human serum as complement in gelatin veronal buffer (GVB, Sigma, St. Louis, Mo.) with added EGTA (ethylene glycol-bis[β-aminoethyl ether]N,N,$N^1,N^1$-tetraacetic acid) and $Mg^{2+}$ to 8 mM and 2 mM, respectively. Rabbit erythrocytes ($4.5 \times 10^6$ cells/ml), human serum (1 in 24 dilution), and the compounds to be tested were incubated one hour at 37° C. in a V-bottom microtiter plate, cells pelleted by centrifugation, the supernatants transferred to a flat-bottom microtiter plate, and the absorbance at 410 nm determined. Samples were paired with identical controls lacking human serum (complement-independent lysis). Both samples and controls were run in triplicate. Control values were subtracted from sample values and the fractional inhibition was determined relative to the uninhibited (no added compound) sample. Results are reported as the concentration of compound yielding fifty per cent (50%) inhibition, $AH_{50}$. The $AH_{50}$ values for several of the compounds are included along with the results of other in vitro assays in Table XIV. As seen in Table XIV, compound 68 inhibited the classical pathway more effectively than K76COOH, but was somewhat less potent than K76COOH in inhibiting alternative complement pathway. Compound 44a inhibited the classical pathways as well as K76COOH, but was clearly less potent than K76COOH or 68 in inhibiting the alternative pathway.

10.4. INHIBITION OF C3b PROTEOLYSIS BY FACTOR I

K76COOH has been shown to inhibit the proteolysis of C3b by factor I and the cofactor protein H (Hong et al., 1981, J. Immunol., 127:104–108. The capacity of the substituted dihydrobenzofurans to inhibit the specific degradation of the C3b a-chain by factor I was assessed on sodium dodecylsulfate-polyacrylamide gel electrophoresis (SDS-PAGE; Wong et al., 1985, J. Immunol. Methods, 82:303–313; Weisman et al., 1990, Science, 249:146–151) using either factor H or sCR1 as cofactor. Purified C3b at 1.2 μM, factor I (Cytotech, San Diego, Calif.) at 0.1 μM, sCR1 at 8 nM as a cofactor, and test compound at varying concentrations, were incubated for 60 minutes at 37° C. The reactions were stopped by the addition of reducing SDS-PAGE sample buffer (Laemmli, 1970, Nature, 227:680–685) subjected to electrophoresis on 4–20% polyacrylamide gradient gels, visualized with Coomassie Blue stain, and quantitated by densitometry. Controls lacking factor I and controls with factor I but lacking test compounds were included. Results are reported as the concentration of test compound which inhibited approximately fifty percent (50%) of the C3b a-chain degradation, $IC_{50}$.

The results for several compounds are included in Table XIV.

TABLE XIV

In vitro assays of complement inhibition by substituted spiro[benzofuran-2(3H)-cyclohexanes]. Concentration* (μM) yielding 50% inhibition.

| Compound | Classical pathway $IH_{50}$ (μM) | Alternative pathway $AH_{50}$ (μM) | C3b cleavage by Factor I (μM) |
|---|---|---|---|
| K76COOH | 570 (±170; n = 9) | 850 (n = 1) | 110 |
| 68 | 160(±69; n = 9) | 1360 (±320; n = 3) | 150 |
| 44a | 530(±190; n = 23) | >5030 | 2740 |

*Values reported are the mean (± standard deviation; sample number, n)
Compound 68 and K76COOH were equally effective in inhibiting proteolysis of C3b by factor I using sCR1 as a cofactor.

10.5. GUINEA PIG-TO-RAT CARDIAC TRANSPLANT

The effects of compounds 68 and 44a on hyperacute graft rejection were tested in a model of discordant xenografting. The methods were the same as described previously (Prewitt et al., 1991, Transplantation 52:868–873) except that the test compounds were substituted for the active agent (sCR1) of the earlier study. As indicated in the earlier study, male Lewis rats, 12–16 weeks of age, and male Hartley guinea pigs, 4–10 weeks of age (Charles River, Wilmington, Mass.) served as cardiac xenograft recipients and donors, respectively. Under Halothane anesthesia, heterotopic cardiac xenotransplantation was performed by a modification of the microvascular technique of Ono and Lindsey, 1990, J. Thorac. Cardiovas.

Surg., 57:225, with anastomosis of the donor aorta to the recipient infrarenal aorta and the donor pulmonary artery to the recipient inferior vena cava. Cardiac xenografts were evaluated visually over the first 30 minutes following reperfusion and then, following abdominal closure, every 10 minutes by palpation until rejection. Rejection was defined as total cessation of cardiac xenograft contraction and was confirmed by direct visualization and histological examination. The compounds 68 and 44a were prepared as 14 mg/ml solutions in phosphate buffered saline (PBS) and were administered as a 2.0 ml intravenous bolus into the recipient inferior vena cava, superior to the caval cross clamp, immediately prior to cardiac xenograft reperfusion. Control animals received similar volumes of PBS. Three (n=3) control animals were tested concurrent with the animals receiving compound 68; data from historic controls (n=13) subjected to the same procedure and previously reported (Pruitt et al., 1991, Transplantation 52:868–873) are also included for comparison. Table XV includes the xenograft survival times (minutes) for individual animals and the means and standard errors of the mean (SEM) for the various groups. As can be seen in the table, compound 68 treatment resulted in prolonged graft survival times in 2 of the 3 animals tested relative to controls.

TABLE XV

Guinea pig-to-rat cardiac transplant

| Treatment | Graft survival time (minutes) | Mean ± SEM (minutes) |
|---|---|---|
| Historic controls (PBS) | 5, 7, 7, 9, 9, 10, 10, 11, 16, 17, 24, 40, 60 | 17 ± 4 |
| Concurrent controls (PBS) | 5, 7, 19 | 10 ± 4 |
| 68 at 28 mg/rat | 7, 150, 270 | 142 ± 76 |
| 44a at 28 mg/rat | 7, 9 | 8 |

The present invention is not to be limited in scope by the foregoing examples, which are intended as purely illustrative of specific aspects of the invention and any compounds that are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entireties.

What is claimed is:

1. A compound of the general formula 4:

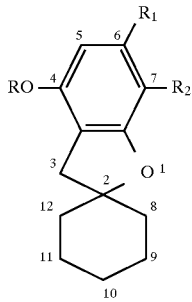

in which R represents a hydrogen atom, a lower alkyl group, a substituted lower alkyl group, a benzyl group, a substituted benzyl group; $R_2$ represents a hydrogen atom; $R_1$ represents a formyl group, carboxylic acid group; or a pharmaceutically acceptable acid or base addition salt or ester thereof.

2. The compound of claim 8 which is selected from the group consisting of 6-carboxy-4-ethoxyspiro[benzofuran-2(3H)-cyclohexane], 6-formyl-4-hydroxyspiro[benzofuran-2(3H)-cyclohexane], 4-benzyloxy-6-formylspiro[benzofuran-2(3H)-cyclohexane], 4-butyloxy-6-formylspiro[benzofuran-2(3H)-cyclohexane], 6-formyl-4-(2-hydroxyethyloxy)spiro[benzofuran-2(3H)-cyclohexane], 6-formylspiro[benzofuran-2(3H)-cyclohexane], 4-benzyloxy-6-carboxyspiro[benzofuran-2(3H)-cyclohexane], 4-butyloxy-6-carboxyspiro[benzofuran-2(3H)-cyclohexane], 6-carboxy-4-(2-hydroxyethyloxy)spiro[benzofuran-2(3H)-cyclohexane], and 6-carboxyspiro[benzofuran-2(3H)-cyclohexane].

3. The compound which is 6-carboxy-4-methoxyspiro[benzofuran-2(3H)-cyclohexane].

* * * * *